US012210017B2

(12) United States Patent
Khurana

(10) Patent No.: US 12,210,017 B2
(45) Date of Patent: Jan. 28, 2025

(54) PEPTIDES REPRESENTING EPITOPES FROM FILOVIRUSES

(71) Applicant: The U.S.A., as represented by the Secretary, Department of Health and Human Services, Silver Spring, MD (US)

(72) Inventor: Surender Khurana, Clarksburg, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 748 days.

(21) Appl. No.: 17/144,843

(22) Filed: Jan. 8, 2021

(65) Prior Publication Data

US 2021/0208160 A1    Jul. 8, 2021

Related U.S. Application Data

(60) Provisional application No. 62/958,612, filed on Jan. 8, 2020.

(51) Int. Cl.
*G01N 33/569*    (2006.01)
*A61K 39/12*    (2006.01)
(Continued)

(52) U.S. Cl.
CPC ....... *G01N 33/56983* (2013.01); *A61K 39/12* (2013.01); *C07K 16/10* (2013.01); *G01N 33/6857* (2013.01); *G01N 2800/26* (2013.01)

(58) Field of Classification Search
CPC ........... G01N 33/6857; G01N 2800/26; A61K 39/12; C07K 16/10
See application file for complete search history.

(56) References Cited

U.S. PATENT DOCUMENTS 4,428,931 A    1/1984    Tolman et al.
4,488,991 A    12/1984    Tolman et al.
(Continued)

FOREIGN PATENT DOCUMENTS

EP          2944321 A1 * 11/2015    ............ A61K 39/12
WO    WO-2017060662 A1 *  4/2017

OTHER PUBLICATIONS

Qiu et al. (Antibody therapy for Ebola, 2014) (Year: 2014).*
(Continued)

*Primary Examiner* — Ann Montgomery
*Assistant Examiner* — Chau N. B. Tran
(74) *Attorney, Agent, or Firm* — Klarquist Sparkman, LLP

(57) ABSTRACT

Methods of identifying a subject with a Filovirus infection are provided herein. In some embodiments, the method comprises contacting a biological sample containing antibodies from the subject with one or more peptides comprising amino acid sequences of selected Filovirus epitopes, detecting the presence or absence of an immune complex of antibodies from the biological sample with the one or more peptides; and wherein the presence of the immune complex identifies the subject as having Filovirus infection and the absence of the immune complex identifies the subject as not having Filovirus infection. Further provided are isolated peptides for use in such methods, as well as a solid support linked to one or more of the disclosed peptides.

26 Claims, 40 Drawing Sheets

Specification includes a Sequence Listing.

(51) Int. Cl.
*C07K 16/10* (2006.01)
*G01N 33/68* (2006.01)

(56) References Cited

U.S. PATENT DOCUMENTS

| | | | |
|---|---|---|---|
| 4,547,367 A | 10/1985 | Tabor et al. | |
| 4,547,368 A | 10/1985 | Tabor et al. | |
| 4,709,017 A | 11/1987 | Collier et al. | |
| 4,722,848 A | 2/1988 | Paoletti et al. | |
| 4,997,915 A | 3/1991 | Tan et al. | |
| 5,151,023 A | 9/1992 | Kuzuhara et al. | |
| 5,589,466 A | 12/1996 | Felgner et al. | |
| 5,593,972 A | 1/1997 | Weiner et al. | |
| 5,601,826 A | 2/1997 | Halpern | |
| 5,602,095 A | 2/1997 | Pastan et al. | |
| 5,643,578 A | 7/1997 | Robinson et al. | |
| 5,817,317 A | 10/1998 | Titball et al. | |
| 5,817,637 A | 10/1998 | Weiner et al. | |
| 5,880,103 A | 3/1999 | Urban et al. | |
| 6,013,264 A | 1/2000 | Petre et al. | |
| 6,399,076 B2 | 6/2002 | Vose et al. | |
| 6,403,094 B1 | 6/2002 | Titball et al. | |
| 6,696,065 B1 | 2/2004 | Fahim et al. | |
| 10,160,795 B2 | 12/2018 | Sullivan et al. | |
| 2003/0224015 A1* | 12/2003 | Hart | C07K 14/005 435/235.1 |
| 2017/0183396 A1* | 6/2017 | Berry | C07K 16/10 |
| 2017/0326225 A1* | 11/2017 | Rauch | C07K 14/005 |
| 2018/0244758 A1* | 8/2018 | Bornholdt | A61P 31/14 |
| 2020/0132685 A1* | 4/2020 | Anderson | G01N 33/54393 |

OTHER PUBLICATIONS

Krahling et al. (Development of an antibody capture ELISA using inactivated Ebola Zaire Makona virus, Med Microbiol Immunol (2016) 205:173-183) (Year: 2016).*
Paweska et al. (Evaluation of Diagnostic Performance of Three Indirect Enzyme-Linked Immunosorbent Assays for the Detection of IgG Antibodies to Ebola Virus in Human Sera, Viruses 2019, 11, 678; doi:10.3390/v11080678) (Year: 2019).*
Becquart et al. (Identification of Continuous Human B-Cell Epitopes in the VP35, VP40, Nucleoprotein and Glycoprotein of Ebola Virus, 2014) (Year: 2014).*
Spencer et al. (Recombinant viral proteins for use in diagnostic ELISAs to detect virus infection, 2007) (Year: 2007).*
Janeway et al. (Immunobiology: the Immune System in Health and Disease (2001), Elsevier Science Ltd/Garland Publishing, New York, NY, Fifth Edition, see sections 3-6 and 3-7) (Year: 2001).*
Almagro et al. ("Humanization of Antibodies", Frontiers in Bioscience 13, 1619-1633, 2008) (Year: 2008).*
Goel et al. ("Plasticity within the Antigen Combining Site May Manifest as Molecular Mimicry in the Humoral Immune Response", The Journal of Immunology 173(12):7358-7367, 2004) (Year: 2004).*
Edwards et al. ("The remarkable flexibility of the human antibody repertoire; isolation of over one thousand different antibodies to a single protein, BLyS" J. Mol. Biol. (2003) 334, 103-118, DOI: 10.1016/j.jmb.2003.09.054) (Year: 2003).*
Lloyd et al. ("Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058) (Year: 2009).*
Brown et al. ("Tolerance of single, but not multiple, amino acid replacements in antibody VH CDR 2: a means of minimizing B cell wastage from somatic hypermutation?", J Immunol. May 1996; 156(9):3285-91) (Year: 1996).*
Vajdos et al. ("Comprehensive functional maps of the antigen-binding site of an anti-ErbB2 antibody obtained with shotgun scanning mutagenesis" J Mol Biol. Jul. 5, 2002;320(2):415-28, Doi: 10.1016/S0022-2836(02)00264-4) (Year: 2002).*
Verma (Biotin-tagged proteins: Reagents for efficient ELISA-based serodiagnosis and phage display based affinity selection, Plos One, 2018). (Year: 2018).*
Saijo et al. (Enzyme-Linked Immunosorbent Assays for Detection of Antibodies to Ebola and Marburg Viruses Using Recombinant Nucleoproteins, Journal Of Clinical Microbiology, Jan. 2001, p. 1-7). (Year: 2001).*
Barnes et al., "Evidence of Ebola Virus Replication and High Concentration in Semen of a Patient During Recovery," *Clin. Infect. Dis.*, vol. 65:1400-1403, 2017.
Brito et al., "Self-Amplifying mRNA Vaccines," *Adv Genet.*, vol. 89:179-233, 2015.
Chertow et al., "Severe Meningoencephalitis in a Case of Ebola Virus Disease: A Case Report," *Ann. Intern. Med.*, vol. 165: 301-304, 2016.
ClinicalTrials.gov Identifier: NCT02363322; NIH IRB Protocol #15-I-0083 https://clinicaltrials.gov/ct2/show/NCT02363322.
Cohen et al., "Clinical Trials. Ebola Vaccines Face Daunting Path to Approval," Science, vol. 349: 1272-1273, 2015.
Davis et al., "Longitudinal Analysis of the Human B Cell Response to Ebola Virus Infection," Cell, vol. 177:1566-1582, 2019.
Deen et al., "Ebola RNA Persistence in Semen of Ebola Virus Disease Survivors—Final Report," N. Engl. J. Med., vol. 377:1428-1437, 2017.
Fuentes et al., "Antigenic Fingerprinting Following Primary RSV Infection in Young Children Identifies Novel Antigenic Sites and Reveals Unlinked Evolution of Human Antibody Repertoires to Fusion and Attachment Glycoproteins," *PLoS Pathog.*, vol. 12:e1005554, 2016.
Fuentes et al., "Human Antibody Repertoire following Ebola virus Infection and Vaccination," *iScience*, 23:100920, 2020.
Geall et al., "Nonviral Delivery of Self-Amplifying RNA Vaccines," *Proc. Natl. Acad. Sci. USA*, vol. 109:14604-14609, 2012.
GenBank Accession No. NC007322, "Bacillus anthracis str. 'Ames Ancestor' plasmid pXO1, complete sequence", downloaded Jan. 9, 2020.
Groen et al., "Serological Reactivity of Baculovirus-Expressed Ebola Virus VP35 and Nucleoproteins," *Microbes Infect.*, vol. 5:379-385, 2003.
World Health Organization, Ebola in the Democratic Republic of the Congo, North Kivu, Ituri 2018-2020, https://www.who.int/emergencies/diseases/ebola/drc-2019, downloaded Jan. 5, 2021.
Kash et al., "Longitudinal Peripheral Blood Transcription Analysis of a Patient with Severe Ebola Virus Disease," *Sci. Transl. Med.*, vol. 9, pp. 1-30, 2017.
Khurana et al., "Antigenic Fingerprinting of H5N1 Avian Influenza Using Convalescent Sera and Monoclonal Antibodies Reveals Potential Vaccine and Diagnostic Targets," *PLoS Med.*, vol. 6: e1000049, Apr. 2009.
Khurana et al., "Vaccines with MF59 Adjuvant Expand the Antibody Repertoire to Target Protective Sites of Pandemic Avian H5N1 Influenza Virus," *Sci. Transl. Med.*, vol. 2, pp. 1-8, 2010.
Khurana et al., "H5N1-SeroDetect EIA and Rapid Test: A Novel Differential Diagnostic Assay for Serodiagnosis of H5N1 Infections and Surveillance," *J. Virol.*, vol. 85:12455-12463, 2011.
Khurana et al., "MF59 Adjuvant Enhances Diversity and Affinity of Antibody-Mediated Immune Response to Pandemic Influenza Vaccines," *Sci. Transl. Med.*, vol. 3: pp. 1-25, 2011.
Khurana et al., "Human Antibody Repertoire After VSV-Ebola Vaccination Identifies Novel Targets and Virus-Neutralizing IgM Antibodies," *Nat. Med.*, vol. 22:1439-1447, 2016.
Khurana et al., "Repeat Vaccination Reduces Antibody Affinity Maturation Across Different Influenza Vaccine Platforms in Humans," *Nat. Commun.*, vol. 10.3338-3353, 2019.
Khurana et al., "Longitudinal Human Antibody Repertoire Against Complete Viral Proteome Following Acute Ebola Virus Infection Reveals Protective Sites for Vaccine Design," *Cell Host Microbe*, vol. 27:262-276, 2020.
Krause, "Interim Results from a Phase 3 Ebola Vaccine Study in Guinea," *Lancet*, vol. 386:831-833, 2015.
Lehrer et al., "Recombinant Subunit Vaccines Protect Guinea Pigs from Lethal Ebola Virus Challenge," *Vaccine*, vol. 37: 6942-6950, 2019.

(56) References Cited

OTHER PUBLICATIONS

Lu et al., "Beyond Binding: Antibody Effector Functions in Infectious Diseases," Nat. Rev. Immunol., vol. 18: 46-61, 2018.
Madara et al., "The Multifunctional Ebola Virus VP40 Matrix Protein is a Promising Therapeutic Target," Future Virol., vol. 10:537-546, 2015.
Magini et al., "Self-Amplifying mRNA Vaccines Expressing Multiple Conserved Influenza Antigens Confer Protection Against Homologous and Heterosubtypic Viral Challenge," PLoS One, vol. 11:e0161193, 2016.
Matassov et al., "Vaccination with a Highly Attenuated Recombinant Vesicular Stomatitis Virus Vector Protects Against Challenge with a Lethal Dose of Ebola Virus," J. Infect. Dis., vol. 212: S443-S451, 2015.
McElroy et al., "Kinetic Analysis of Biomarkers in a Cohort of US Patients with Ebola Virus Disease," Clin. Infect. Dis., vol. 63:460-467, 2016.
Meredith et al., "The Conundrum of the Glasgow Coma Scale in Intubated Patients: A Linear Regression Prediction of the Glasgow Verbal Score from the Glasgow Eye and Motor Scores," J Trauma, vol. 44:839-845, 1998.
Mowat et al., "ISCOMS—A Novel Strategy for Mucosal Immunization?" Immunol Today, vol. 12:383-385, 1991.
Murin et al., "Structural Basis of Pan-Ebolavirus Neutralization by an Antibody Targeting the Glycoprotein Fusion Loop," Cell Rep., vol. 24:2723-2732, 2018.
Newman et al., "Use of Nonionic Block Copolymers in Vaccines and Therapeutics," Crit. Rev. Ther. Drug Carrier Syst., vol. 15:98-142, 1998.
Paweska et al., "Evaluation of Diagnostic Performance of Three Indirect Enzyme-Linked Immunosorbent Assays for the Detection of IgG Antibodies to Ebola Virus in Human Sera," Viruses, vol. 11, pp. 1-18, 2019.
Petsch et al., "Protective Efficacy of In Vitro Synthesized, Specific Mrna Vaccines Against Influenza A Virus Infection," Nat. Biotechnol., vol. 30.12: 1210-1216, Dec. 2012.
Pichichero, "Protein Carriers of Conjugate Vaccines: Characteristics, Development, and Clinical Trials," Hum. Vaccin. Immunother., vol. 9:2505-2523, 2013.
Prevail III Study Group et al., "A Longitudinal Study of Ebola Sequelae in Liberia," N. Engl. J. Med., vol. 380:924-934, 2019.
Ravichandran et al., "Differential Human Antibody Repertoires Following Zika Infection and the Implications for Serodiagnostics and Disease Outcome," Nat. Commun., vol. 10: 1943-1957, 2019.
Saphire et al., "Systematic Analysis of Monoclonal Antibodies Against Ebola Virus GP Defines Features that Contribute to Protection," Cell, vol. 174: 938-952, 2018.
Stover et al., "New Use of BCG for Recombinant Vaccines," Nature, vol. 351:456-460, 1991.
Takahashi et al., "Induction of CD8+ Cytotoxic T Cells by Immunization with Purified HIV-1 Envelope Protein in ISCOMs," Nature, vol. 344: 873-875, 1990.
Wang et al., "Expression and Immunogenicity of VP40 Protein of ZEBOV," Arch. Iran Med., vol. 20:246-250, 2017.
Wilkinson et al., "Comparison of Platform Technologies for Assaying Antibody to Ebola Virus," Vaccine, vol. 35:1347-1352, 2012.
Wilson et al., "Vaccine Potential of Ebola Virus VP24, VP30, VP35 and VP40 Proteins," Virol., vol. 286:384-390, 2001.
Wong et al., "Immune Parameters Correlate with Protection Against Ebola Virus Infection in Rodents and Nonhuman Primates," Sci. Transl. Med., vol. 4: pp. 1-18, 2012.
Yamayoshi et al., "Mapping of a Region of Ebola Virus VP40 that is Important in the Production of Virus-Like Particles," J. Infect. Dis., vol. 196: S291-S295, 2007.

\* cited by examiner

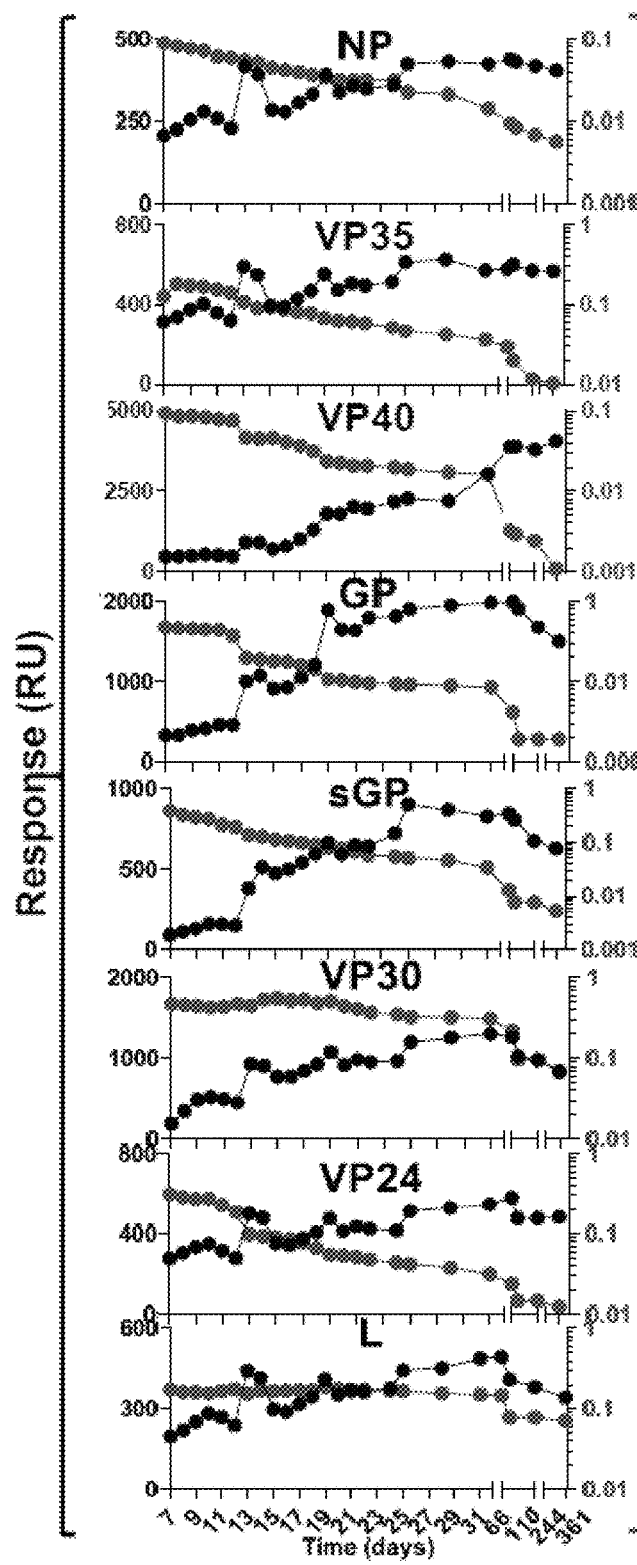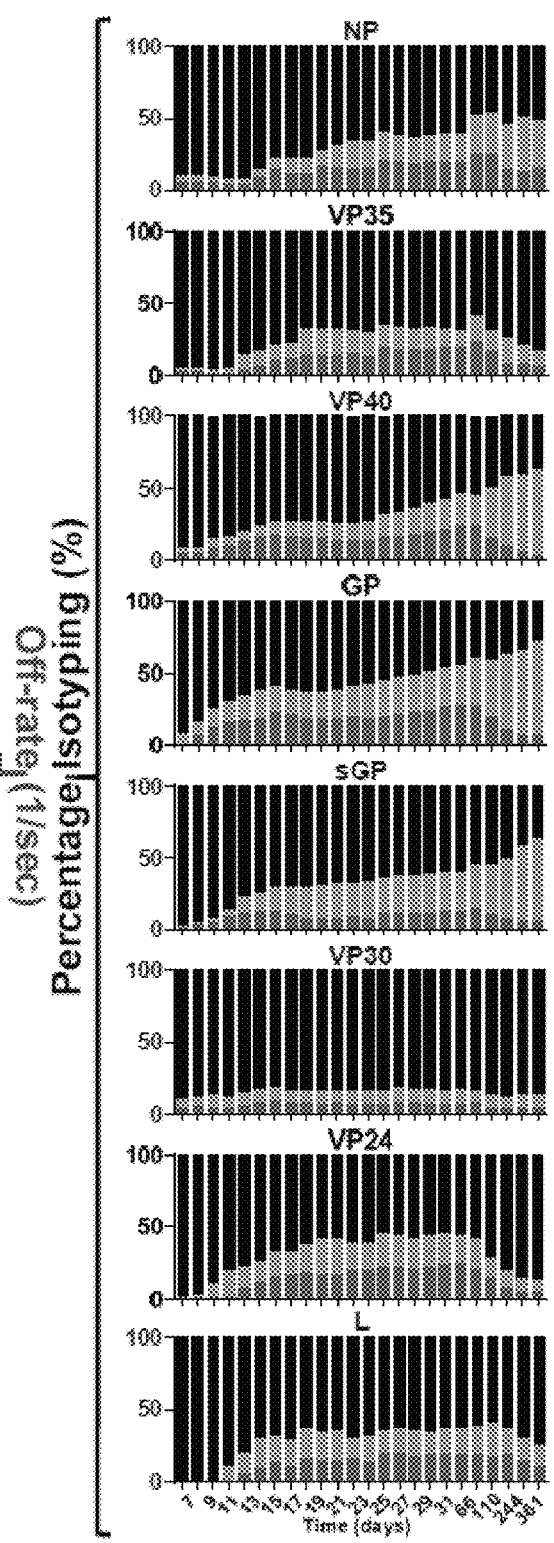

FIG. 4C Ebola GP

TM Domain

FIG. 4D

Site IV.1 (282-305)
3CSY    Model

Site V.1 (343-368)
Model

Site V.7 (469-498)
Model

Site V.9 (520-547)
6DZL    Model

Site VI (617-645)
Model

FIG. 5A

| Group | Dose | Emulsigen (1:1) | N |
|---|---|---|---|
| IV.1 (GP 282-305) | 20 ug | + | 10 |
| V.1 (GP 343-368) | 20 ug | + | 10 |
| V.7 (GP 469-498) | 20 ug | + | 10 |
| V.9 (GP 520-547) | 20 ug | + | 10 |
| VI (GP 617-645) | 20 ug | + | 10 |
| Mix peptide | 20 ug | + | 10 |
| KLH | 20 ug | + | 10 |
| EBOV GP - VEEV replicon particle (VRP) | | - | 10 |
| Naive | | - | 10 |

FIG. 5B Makona GP

FIG. 5C Mayinga GP

Serum analyses of EVD patient during first month post-symptom onset

| Time (Days since symptom onset) | RT-qPCR (Ct values) | Clinical SOFA Score | EBOV IgM ELISA (A405nm) | EBOV IgG ELISA (Units/ml) | EBOV GP IgG ELISA (Units/ml) | PRNT80 Titers |
|---|---|---|---|---|---|---|
| 7 | 23.99 | 4 | 0.18965 | 0.094 | 0.00005 | 5 |
| 8 | 23.21 | 4 | 0.2663 | 0.103 | 0.00522 | 5 |
| 9 | 24.68 | 5 | 0.3532 | 0.197 | 0.0022 | 5 |
| 10 | 25.88 | 8 | 0.4487 | 0.263 | 0.02211 | 5 |
| 11 | 29.38 | 11 | 0.4116 | 0.258 | 0.02998 | 5 |
| 12 | 31.21 | 11 | 0.4123 | 0.315 | 0.08751 | 5 |
| 13 | 32.81 | 12 | 0.4925 | 0.64 | 0.18832 | 5 |
| 14 | 34.54 | 14 | 0.49745 | 0.962 | 0.69702 | 5 |
| 15 | 33.58 | 10 | 0.60705 | 1.212 | 1.08969 | 5 |
| 16 | 36.4 | 10 | 0.74235 | 1.437 | 1.19694 | 5 |
| 17 | 37.46 | 9 | 0.78795 | 1.83 | 0.92019 | 10 |
| 18 | 37.87 | 5 | 0.7008 | 2.48 | 1.6483 | 10 |
| 19 | 39.1 | 3 | 0.64455 | 8.58 | 1.1595 | 20 |
| 20 | 37.71 | 1 | 0.5974 | 12.5 | 2.36959 | |
| 21 | BLD | | 0.5167 | 13.88 | 3.23573 | 80 |
| 22 | 37.49 | | 0.591 | 14.5 | 2.35441 | 20 |
| 24 | BLD | | 0.54905 | 12.13 | 1.80012 | |
| 25 | BLD | | 0.52425 | 19.05 | 1.01298 | 40 |
| 26 | | | 0.53665 | 16.5 | 1.87949 | 40 |
| 27 | | | 0.56935 | 13.9 | 3.98523 | 40 |
| 28 | | | 0.8649 | 20.34 | 4.74795 | 40 |
| 29 | | | 0.6724 | 19.14 | 2.63623 | 80 |
| 30 | | | 0.7893 | 16.72 | 4.21387 | |
| 31 | | | | | | 80 |

FIG. 7A

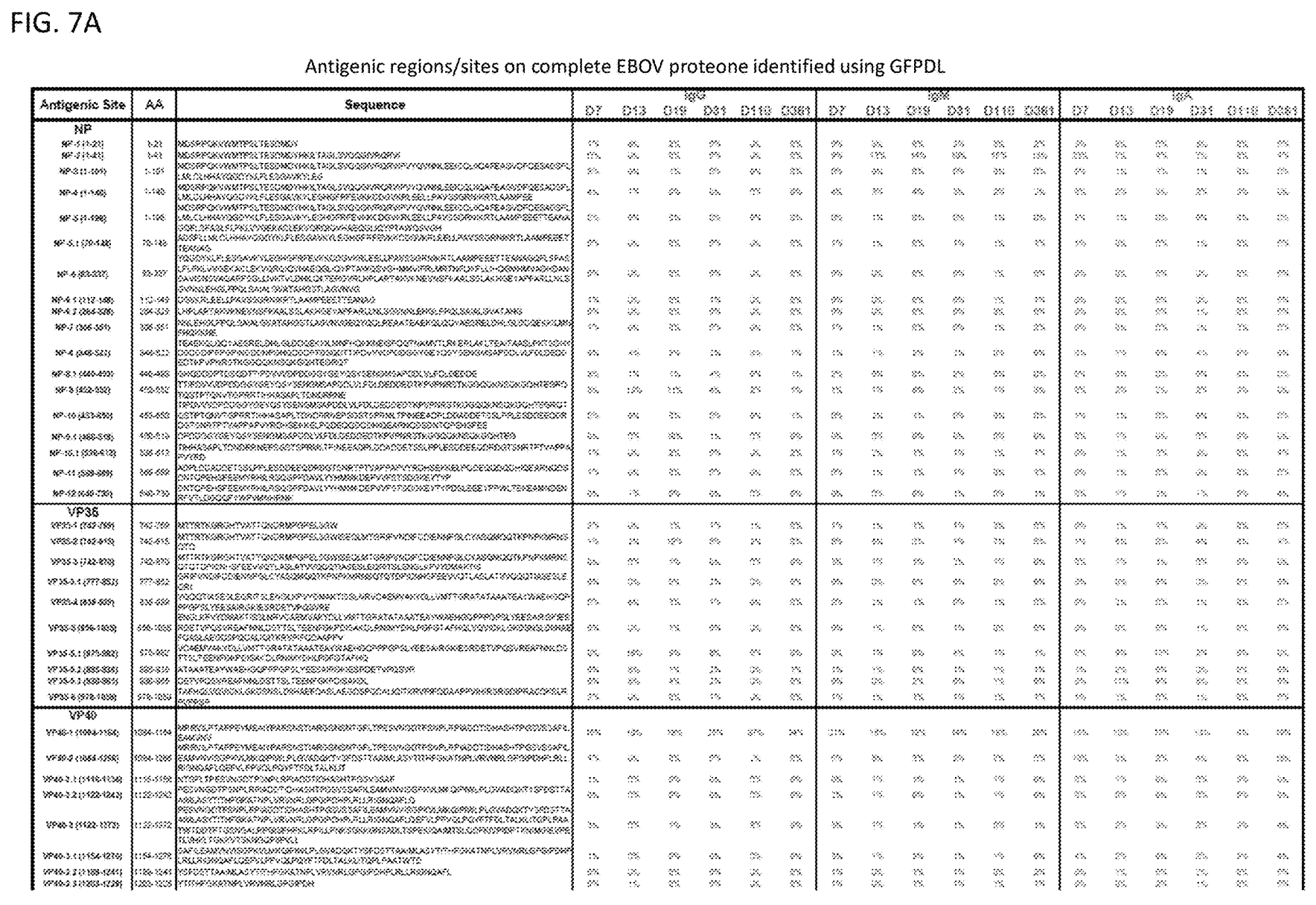

Antigenic regions/sites on complete EBOV proteone identified using GFPDL

Sequence similarity of GP antigenic sites with other Ebolaviruses

| Antigenic Site | AA | Sequence | Makona (%) | Mayinga (%) | Sudan (%) | Bundibugyo (%) | Reston (%) |
|---|---|---|---|---|---|---|---|
| I (1-36) | 1412-1427 | MGVTGILQLPRDRFKRTSFFLWVIILFQRTFSIPLG | 100 | 100 | 66.6 | 69.4 | 100 |
| II (32-273) | 1443-1674 | SIPLGVIHNSTLQVSDVDKLVCRDKLSSTNQLRSVGLNL EGNGVATDVPSATKRWGFRSGVPPKVVNYEAGEWAE NCYNLEIKKPDGSECLPAAPDGIRGFPRCRYVHKVSGT GPCAGDFAFHKEGAFFLYDRLASTVIYRGTTFAEGVVA FLLPQAKKDFFSSHPLREPVNATEDPSSGYYSTTIRYQ ATGFGTNETEYLFEVDNLTYVQLESRFTPQFLLQLNETI YASGKRSNTTGKL | 100 | 99.1 | 68.1 | 80.1 | 99.1 |
| II.1 (152-220) | 1563-1631 | AFHKEGAFFLYDRLASTVIYRGTTFAEGVVAFLLPQAK KDFFSSHPLREPVNATEDPSSGYYSTTIRY | 100 | 100 | 65.2 | 75.3 | 100 |
| II.2 (195-226) | 1607-1637 | SSHPLREPVNATEDPSSGYYSTTIRYQATGFG | 100 | 100 | 43.7 | 53.1 | 100 |
| II.3 (61-104) | 1473-1515 | NQLRSVGLNLEGNGVATDVPSATKRWGFRSGVPPKV VNYEAGEW | 100 | 97.7 | 84 | 88.6 | 97.7 |
| III (205-364) | 1616-1775 | ATEDPSSGYYSTTIRYQATGFGTNETEYLFEVDNLTYV QLESRFTPQFLLQLNETIYASGKRSNTTGKLIWKVNPEI DTTIGEWAFWETKKNLTRKIRSEELSFTAVSNGPKNISG QSPARTSSDPETNTTNEDHKIMASENSSAMVQVHSQG RKAAVSH | 100 | 86.6 | 39.7 | 53.6 | 96.6 |
| III.2 (232-291) | 1643-1702 | YLFEVDNLTYVQLESRFTPQFLLQLNETIYASGKRSNTT GKLIWKVNPEIDTTIGEWAFW | 100 | 98.3 | 55 | 78.3 | 98.3 |
| IV (267-434) | 1678-1845 | SNTTGKLIWKVNPEIDTTIGEWAFWETKKNLTRKIRSEE LSFTAVSNGPKNISGQSPARTSSDPETNTTNEDHKIMA SENSSAMVQVHSQGRKAAVSHLTTLATISTSPQPPTTK TGPDNSTHNTPVYKLDISEATQVGQHHRRADNDSTAS DTPPATTAAGPLKAEN | 100 | 93.4 | 28.7 | 30 | 94.7 |
| IV.1 (282-305) | 1693-1716 | DTTIGEWAFWETKKNLTRKIRSEE | 100 | 100 | 62.5 | 66.6 | 100 |
| IV.3 (288-364) | 1697-1775 | GEWAFWETKKNLTRKIRSEELSFTAVSNGPKNISGQSP ARTSSDPETNTTNEDHKIMASENSSAMVQVHSQGRKA AVSH | 100 | 94.3 | 35.7 | 37.1 | 94.2 |
| IV.6 (326-358) | 1737-1762 | TSSDPETNTTNEDHKIMASENSSAMV | 100 | 92.3 | 15.3 | 19.2 | 92.3 |
| IV.8 (326-403) | 1737-1814 | TSSDPETNTTNEDHKIMASENSSAMVQVHSQGRKAAV SHLTTLATISTSPQPPTTKTGPDNSTHNTPVYKLDISEA TQ | 100 | 92.3 | 12.6 | 14.1 | 94.8 |
| V (336-582) | 1747-1993 | NEDHKIMASENSSAMVQVHSQGRKAAVSHLTTLATIST SPQPPTTKTGPDNSTHNTPVYKLDISEATQVGQHHRR ADNDSTASDTPPATTAAGPLKAENTNTSKSADSLDLAT TTSPQNYSETAGNNNTHHQDTGEESASSGKLGLITNTI AGVAGLITGGRRTRREVIVNAQPKCNPNLHYWTTQDE GAAIGLAWIPYFGPAAEGIYTEGLMHNQNGLICGLRQL ANETTQALQLFLRATTELRTF | 100 | 93.9 | 35.6 | 42.5 | 95.1 |
| V.1 (343-368) | 1754-1779 | ASENSSAMVQVHSQGRKAAVSHLTTL | 100 | 96.1 | 19.2 | 19.2 | 96.1 |
| V.2 (372-430) | 1779-1853 | LATISTSPQPPTTKTGPDNSTHNTPVYKLDISEATQVGQ HHRRADNDSTASDTPPATTAAGPLKAENTNTSKSAD | 100 | 89.3 | 12 | 9.3 | 93.3 |
| V.3 (380-491) | 1791-1902 | TKTGPDNSTHNTPVYKLDISEATQVGQHHRRADNDST ASDTPPATTAAGPLKAENTNTSKSADSLDLATTTSPQN YSETAGNNNTHHQDTGEESASSGKLGLITNTIAGVAG | 100 | 92 | 15.9 | 15 | 92.9 |
| V.4 (434-447) | 1835-1858 | TTAAGPLKAENTNTSKSADSLDLA | 100 | 83.3 | 4.1 | 8 | 83.3 |
| V.5 (436-491) | 1833-1902 | DTPPATTAAGPLKAENTNTSKSADSLDLATTTSPQNYS ETAGNNNTHHQDTGEESASSGKLGLITNTIAGVAG | 100 | 91.7 | 16.4 | 19.1 | 93.1 |
| V.6 (456-484) | 1867-1895 | SETAGNNNTHHQDTGEESASSGKLGLITN | 100 | 100 | 28.6 | 17.2 | 100 |
| V.7 (469-496) | 1880-1909 | TGEESASSGKLGLITNTIAGVAGLITGGRR | 100 | 100 | 30 | 50 | 100 |
| V.10 (520-547) | 1931-1958 | TQDEGAAIGLAWIPYFGPAAEGIYTEGL | 100 | 96.4 | 71.4 | 96.4 | 100 |
| VI (617-645) | 2018-2056 | DCCIEPHDWTKNITDKIDQIIHDFVDKTLPDQGDNDNW W | 100 | 100 | 79.4 | 92.3 | 100 |
| VII (430-667) | 1841-2078 | LKAENTNTSKSADSLDLATTTSPQNYSETAGNNNTHHQ DTGEESASSGKLGLITNTIAGVAGLITGGRRTRREVIVN AQPKCNPNLHYWTTQDEGAAIGLAWIPYFGPAAEGIYT EGLMHNQNGLICGLRQLANETTQALQLFLRATTELRTF SILNRKAIDFLLQRWGGTCHILGPDCCIEPHDWTKNITD KIDQIIHDFVDKTLPDQGDNDNWWTGWRQWIPAGIGVT GVIIAVIA | 100 | 97 | 68.9 | 72.2 | 97 |
| VII.1 (569-617) | 1980-2028 | LQLFLRATTELRTFSILNRKAIDFLLQRWGGTCHILGPD CCIEPHDWTK | 100 | 100 | 91.8 | 100 | 100 |
| VII.2 (635-667) | 2046-2078 | LPDQGDNDNWWTGWRQWIPAGIGVTGVIIAVIA | 100 | 100 | 78.7 | 90.9 | 100 |

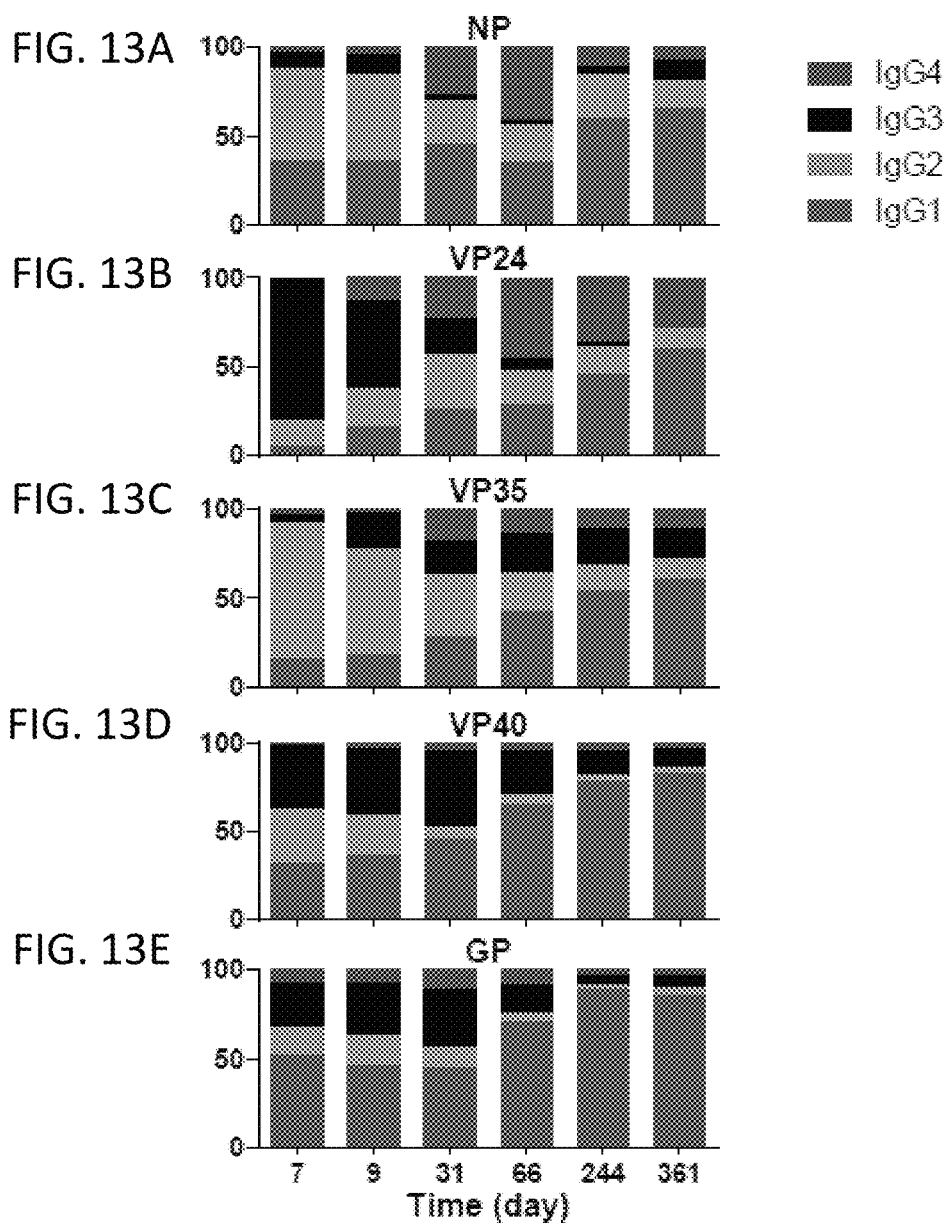

FIG. 14A

```
          10        20        30        40        50        60        70
MDSRPQKVWMTPSLTESDMDTRKILTAGLSVQQGIVRQRVIPVYQVNNLEEICQLIIQAFEAGVDFQESA
                              NP                                       >

80        90       100       110       120       130       140
DSFLLMLCLHHAYQGDYKLPLESGAVKYLEGHGFRFEVKKCDGVKRLEELLPAVSSGRNIKRTLAAMPEE
                              NP                                       >

150       160       170       180       190       200       210
ETTEANAGQFLSFASLFLPKLVVGEKACLEKVQRQIQVHAEQGLIQYPTAWQSVGHMMVIFRLMRTNFLI
                              NP                                       >

220       230       240       250       260       270       280
KFLLIHQGMHMVAGHDANDAVISNSVAQARFSGLLIVKTVLDHILQKTERGVRLHPLARTAKVKNEVNSF
                              NP                                       >

290       300       310       320       330       340       350
KAALSSLAKHGEYAPFARLLNLSGVNNLEHGLFPQLSAIALGVATAHGSTLAGVNVGEQYQQLREAATEA
                              NP                                       >

360       370       380       390       400       410       420
EKQLQQYAESRELDHLGLDDQEKKILMNFHQKKNEISFQQTNAMVTLRKERLAKLTEAITAASLPKTSGH
                              NP                                       >

430       440       450       460       470       480       490
YDDDDDIPFPGPINDDDNPGHQDDDPTDSQDTYIPDVVVDPDDGGYGEYQSYSENGMSAPDDLVLFDLDE
                              NP                                       >

500       510       520       530       540       550       560
DDEDTKPVPNRSTKGGQQKNSQKGQHIEGRQTQSTPTQNVTGPRRTIHHASAPLTDNDRRNEPSGSTSPR
                              NP                                       >

570       580       590       600       610       620       630
MLTPINERADPLDDADDETSSLPPLESDDEEQDRDGTSNRTPTVAPPAPVYRDHSEKKELPQDEQQDQDH
                              NP                                       >

640       650       660       670       680       690       700
IQEARNQDSDNTQPEHSFEEMYRHILRSQGPFDAVLYYHMKKDEPVVFSTSDGKEYTYPDSLEEEYPPWL
                              NP                                       >

710       720       730       740       750       760       770
TEKEAMNDENRFVTLDGQQFYWPVMNHRNKFMAILQHHQ*-MTTRTKGRGHTVATTQNDRMPGPELSGWI
                       NP                 >              VP35          >

780       790       800       810       820       830       840
SEQLMTGRIPVNDIFCDIENNPGLCYASQMQQTKFNPKMRNSQTQTDPICNHSFEEVVQTLASLATVVQQ
                                         VP35                          >

850       860       870       880       890       900       910
QTIASESLEQRITSLENGLKFVYIMAKTISSLNKVCAEMVAKYDLLVMTTGRATATAAATEAYWAEHGQP
                                         VP35                          >

920       930       940       950       960       970       980
PPGPSLYEESAIRGKIESRDETVPQSVRRAFNNLDSTTSLTEENFGKPDISAKDLRNIMYDHLPGFGTAF
                                         VP35                          >

990      1000      1010      1020      1030      1040      1050
HQLVQVICKLGKDSNSLDIIHAEFQASLAEGDSPQCALIQITKRVPIFQDAAPPVIHIRSRGDIPRACQK
                                         VP35                          >

1060      1070      1080      1090      1100      1110      1120
SLRFVPPSPKIDRGWVCVFQLQDGKTLGLKI*-MRRVILPTAFPEYMEAIYPARSNSTIARGGNSNTGFL
               VP35              >                                     _>

```
TPESVNGDTPSNPLRFIADDTIDHASHTPGSVSSAFILEARVRVISGFKVLRKQIPIWLPLGVADQKIYS
                                VP40                                   >
    1280      1290      1300      1310      1320      1330      1340
                                   *
FDGTTAAIMLASYTITHPGKATNPLVRVNRLGPGIPDHPLRLLRIGNQAFLQEPVLFPVQLPQYFTFDLT
                                VP40                                   >
    1270      1280      1290      1300      1310      1320      1330

ALKLITQPLPAATWTDDTPTGSNGALRPGISFHPKLRPILLPNKSGKKGNSADLTSPEKIQAIMTSLQDF
                                VP40                                   >
    1340      1350      1360      1370      1380      1390      1400
                                                                   *
KIVPIDPTKNIMGIEVPETLVHKLTGKKVTSKNGQPIIPVLLPKYIGLDPVAPGDLTNVITQDCDTCHSP
                                VP40                                   >
    1410      1420      1430      1440      1450      1460      1470

ASLPAVVEK*-MGVTGILQLPRDRFKRTSFFLWVIILFQRTFSIPLGVIHNSTLQVSDVDKLVCRDKLSS
         >
                                   GP                                  >
    1480      1490      1500      1510      1520      1530      1540
                                   *
TNQLRSVGLNLEGNGVATDVPSATKRWGFRSGVPPKVVNYEAGEWAENCYNLEIKKPDGSECLPAAPDGI
                                   GP                                  >
    1550      1560      1570      1580      1590      1600      1610
                                                                   *
RGFPRCRYVHKVSGTGPCAGDFAFHKEGAFFLYDRLASTVIYRGTTFAEGVVAFLILPQAKKDFFSSHPL
                                   GP                                  >
    1620      1630      1640      1650      1660      1670      1680

REPVNATEDPSSGYYSTTIRYQATGFGTNETEYLFEVDNLTYVQLESRFTPQFLLQLNETIYASGKRSNT
                                   GP                                  >
    1690      1700      1710      1720      1730      1740      1750
                      *
TGKLIWKVNPEIDTTIGEWAFWETKKNLTRKIRSEELSFTAVSNGPKNISGQSPARTSSDPETNTTNEDH
                                   GP                                  >
    1760      1770      1780      1790      1800      1810      1820
                                                         *
KIKASENSSAMVQVHSQGRKAAVSHLTTLATISTSPQPPTTKTGPDNSTHNTPVYKLDISEATQVGQHHR
                                   GP                                  >
    1830      1840      1850      1860      1870      1880      1890

RAINDSTASDTPPATTAAGPLKAENTNTSKSADSLDLATTTSPQNYSETAGNNNTHHQDTGEESASSSKL
                                   GP                                  >
    1900      1910      1920      1930      1940      1950      1960
      *
GLITNTIASVAGLITGGRRTRREVIVNAQPKCNPNLHYWTTQDEGAAIGLAWIPYFGPAAEGIYTEGLMH
                                   GP                                  >
    1970      1980      1990      2000      2010      2020      2030
                                   *
NQNGLICGLRQLANETTQALQLFLRATTELRTFSILNRKAIDFLLQRWGGTCHILGPDCCIEPHDWTKNI
                                   GP                                  >
    2040      2050      2060      2070      2080      2090      2100
                                                                   *
TDKIDQIIHDFVDKTLPDQGDNDNWWTGWRQWIPAGIGVTGVIIAVIARLCKFVF*-MEASYERGRPRAA
                                   GP                                  >
    2110      2120      2130      2140      2150      2160      2170
RQHSRIQHDHHVRARSSSRENYRGEYRQSRSASQVRVPTVFHKKRVEPLTVPPAPKDICPTLKKGFLCDS
                                VP30                                   >
    2180      2190      2200      2210      2220      2230      2240
                         *
SFCKKDHQLESLTDRELLLLIARKTCGSVEQQLNITAPKDSRLANFTADDFQQEEGPKITLLTLIKTAEH
                                VP30                                   >
    2250      2260      2270      2280      2290      2300      2310
                                                         *
WARQDIRTIEDSKLRALLTLCAVMTRKFSKSQLSLLCETHLRREGLGQDQAEPVLEVYQRLHSDKGGSFE
                                VP30                                   >
```

FIG. 14C

```
             2320        2330        2340        2350        2360        2370        2380
     AALWQQWDRQSLIMFITAFLNIALQLPCESSAVVVSGLRTLVPQSDNEEASTNPGTCSWSDEGTP*-MAK
                            VP30
                                                                                     >
             2390        2400        2410        2420        2430        2440        2450
                            *
     ATGRYNLISPKEDLEKGVVLSDLCNFLVSQTIQGWKVYWAGIEFDVTHKGMALLHRLKTNDPAPAWSMTR
                                        VP24
                                                                                     >
             2460        2470        2480        2490        2500        2510        2520
                                                            *
     NLFPHLFQNFNSTIESPLWALRVILAASIQDQLIDQSLIEPLAGALGLISDWLLTTNTNHPNMRTQRVKE
                                        VP24
                                                                                     >
             2530        2540        2550        2560        2570        2580        2590
     QLSLKMLSLIRSNILKFINKLDALHVVNYNGLLSSIEIGTQNHTIIITRTNMGPLVELQEPDKSAMNRKK
                            VP24
                                                                                     >
             2600        2610        2620        2630        2640        2650        2660
                *
     PGPAKFSLLHESTLKAFTQGSSTRMQSLILEFNSSLAI*-MATQHTQYPDARLSSPIVLDQCDLVTRACG
                            VP24                  >
                                                                                     >
             2670        2680        2690        2700        2710        2720        2730
                                                *
     LYSSYSLNPQLSNCKLPKHIYRLKYDVTVTKPLSDVPVATLPIDPIVPVLLKALSGNGPCPVEPRCQQFL
                                            L
                                                                                     >
             2740        2750        2760        2770        2780        2790        2800
                                                                                *
     DEIIKYTMQDALFLKYYLKNVGAQEDCVDEHFQEKILSSIQGNEFLHQMFFWYDLAILTRRGRLNRGNSR
                                                                L
                                                                                     >
             2810        2820        2830        2840        2850        2860        2870
     STWFVHDDLIDILGYSDYVFWEIPISMLPLNTQGIPHAAMDWYQASVFKEAVQGHTHIVSVSTADVLIMC
                                                                L
                                                                                     >
             2880        2890        2900        2910        2920        2930        2940
                                        *
     KDLITCRPNTTLISRIAEIEDPVCSDYPNFKIVSMLYQSGDYLLSILGSDGYKIIRFLEPLCLAKIQLCS
                                            L
                                                                                     >
             2950        2960        2970        2980        2990        3000        3010
                                                                                *
     KYTERKGRPLTQMSLAVNHTLEEITEMRALKPSQAQKIREFHRTLIRIEMTPQQLCELPSIQKHWGHPVL
                                            L
                                                                                     >
             3020        3030        3040        3050        3060        3070        3080
     HSETAIQKVKKHATVLKALRPIVIFETYCVFKYSIARHYFDSQGSWYSVTSDRNLTPGLNSYIKRNQFPP
                                            L
                                                                                     >
             3090        3100        3110        3120        3130        3140        3150
                    *
     LPMIKELLWEFYHLDHPPLFSTKIISDLSIFIKDRATAVERTCWDAVFEPNVLGYNPPHKFSTKRVPEQF
                                            L
                                                                                     >
             3160        3170        3180        3190        3200        3210        3220
                                                            *
     LEQENFSIENVLSYAQKLEYLLPQYRNFSFSLKEKELNVGRTFGKLPYPTRNVQTLCEALLADGLAKAFP
                                            L
                                                                                     >
             3230        3240        3250        3260        3270        3280        3290
     SNMMVVTEREQKESLLHQASWHHTSDDFGEHATVRGSSPVTDLEKYNLAFRYEFTAPFIEYCNRCYGVKN
                                            L
                                                                                     >
             3300        3310        3320        3330        3340        3350        3360
                *
     VFNWMHYTIPQCYMHVSDYYNPPHNLTLENRDNPPEGPSSYRGHMGGIEGLQQKLWTSISCAQISLVEIK
                                            L
                                                                                     >
             3370        3380        3390        3400        3410        3420        3430
                                                *
     TGFKLRSAVMGDNQCITVLSVFPLETDADEQEQSAEDNAARVAASLAKVTSACGIFLKPDETFVHSGFIY
                                            L
                                                                                     >
             3440        3450        3460        3470        3480        3490        3500
                                                                                *
```

FIG. 14D

```
PGKKQYLNGVQLPQSLKTATRMAPLSDAIPDDLQGTLASIGTAPERSISETRHIFPCRITAAFHTFFSVR
         3510      3520      3530      3540      3550      3560      3570
ILQYHHLGPNKGPDLQQLTLGKPLDFGTISLALAVPQVLGGLSFLNFEKCFYRNLGDPVTSGLPQLKTYL
         3580      3590      3600      3610      3620      3630      3640
RMIEMDDLFLPLIAKNPGNCTAIDFVLNPSGLNVPGSQDLTSFLRQIVRRTITLSAKNKLINTLFHASAD
         3650      3660      3670      3680      3690      3700      3710
FEDEMVCKWLLSSTPVMSRFAADIFSRTPSGKRLQILGYLEGTRTLLASKIINKNTETPVLDRLRKITIQ
         3720      3730      3740      3750      3760      3770      3780
RWSLWPSYLDHCDNILABALTQITCTVDLAQILREYSWAHILEQRPLIGATLPCMIEQFKVFWLKPYEQC
         3790      3800      3810      3820      3830      3840      3850
PQCSNAKQPGGKPFVSVAVKKHIVSAWPNASRISWTIGDGIPYIGSRTEDKIGQPAIKFKCPSAALREAI
         3860      3870      3880      3890      3900      3910      3920
ELASRLTWVTQGSSNSDLLIKPFLEARVNLSVQEILQMTPSHYSGMIVHRYNDQYSPHSFMANRMSNSAT
         3930      3940      3950      3960      3970      3980      3990
RLIVSTNTLGEFSGGGQSARDSNIIFQNVINYAVALFDIKFRNTEATDIQYNRAHLHLTKCCTREVPAQY
         4000      4010      4020      4030      4040      4050      4060
LTYTSTLDLDLTRYRENELIYDSNPLKGGLNCNISFDNPFPQSKRLNIIEDDLIRLPHLSGWELAKTINQ
         4070      4080      4090      4100      4110      4120      4130
SIISDSNNSSTDPISSGRTRSPTTHPLTYPKIGLLYSPGAPVSYYLGNTIIRTKKLTLDNPLYYLTTQIH
         4140      4150      4160      4170      4180      4190      4200
NLPHRSLRILKPTFKHASVMSRLMSIDPHFRIYIGGAAGDRGLSDAARLFLRTSISSFLTFVKEWIINRG
         4210      4220      4230      4240      4250      4260      4270
TIVPLWIVYPLEGQNPTPVNNFLYQIVELLVHDSSRQQAFKTTISDHVHPHDNLVYTCKSTASNFFHASL
         4280      4290      4300      4310      4320      4330      4340
AYWRSRHNSNRKYLARDSSTGSSTNNSDGHIERSQEQTTRIDPHDGTERNLVLQMSHEIKRTTIPQENTH
         4350      4360      4370      4380      4390      4400      4410
QGPSFQSFLSDSACGTANPKLNFDRSRHNVKFQDHNSASKREGHQIISHRLVLPFFTLSQGTRQLTSSNE
         4420      4430      4440      4450      4460      4470      4480
SQTQDEISKYLRQLRSVIDTTVYCRFTGIVSSMHRYKLDEVLWEIESFKSAVTLAESECAGALLLIQKYQV
         4490      4500      4510      4520      4530      4540      4550
KTLFFNILATESSIESEIVSGMTTPRMLLPVMSKFHSDQIEIILNNSASQITDITNPTWFKDQRARLPKQ
         4560      4570      4580      4590      4600      4610      4620
VEVITMDASTTENINRSKLYEAVYKLILHHIDPSVLKAVVLKVFLSDTEGMLWLNDNLAPFFATGYLIKP
         4630      4640      4650      4660      4670      4680      4690
ITSSARSSEWYLCLTNFLSTTRKMFHQNHLSCKQVILTALQLIQRSFYWLSHLTQYADCELRLSYIRLG
```

FIG. 14E

```
                                           L
_____>
       4700       4710       4720       4730       4740       4750       4760
        *
FPSLEKVLYHRYNLVDSKRGPLVSITQHLAHLRAEIRELTNDYRQQRQSRTQTYHPIRTAKGRITKLVND
                                           L
_____>
       4770       4780       4790       4800       4810       4820       4830
                                           *
YLKFFLIVQALKHNGTWQAEFKKLPELISVCNRFYHIRDCNCEERFLVQTLYLHRMQDSEVKLIERLTGL
                                           L
_____>
       4840       4850       4860
LSLFPDGLYRFD*ITVHSILILAKVGY*HIDYKK
                   L
      _____>
```

Anti-GP IgA + IgG + IgM ELISA following GFPDL adsorption

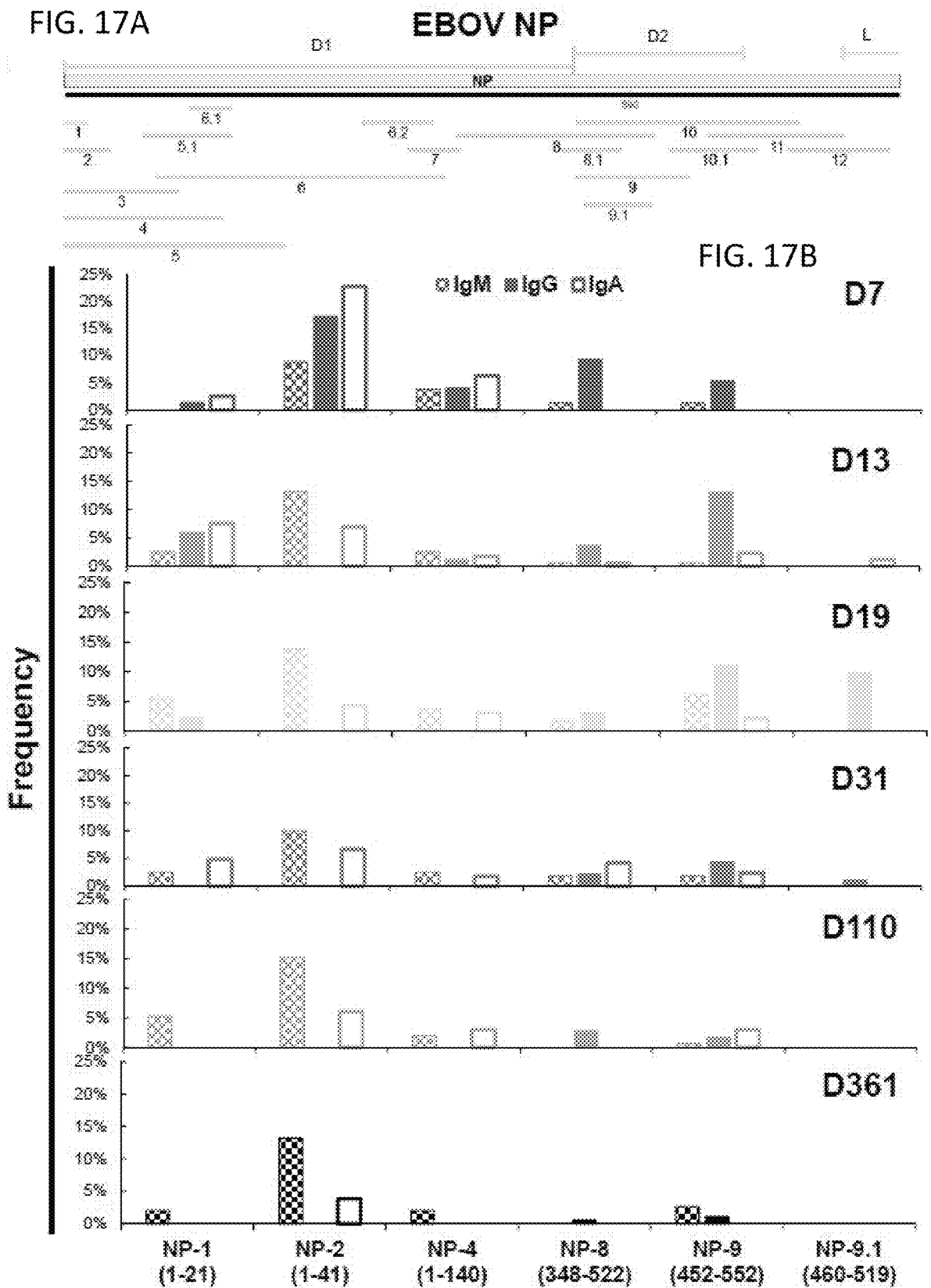

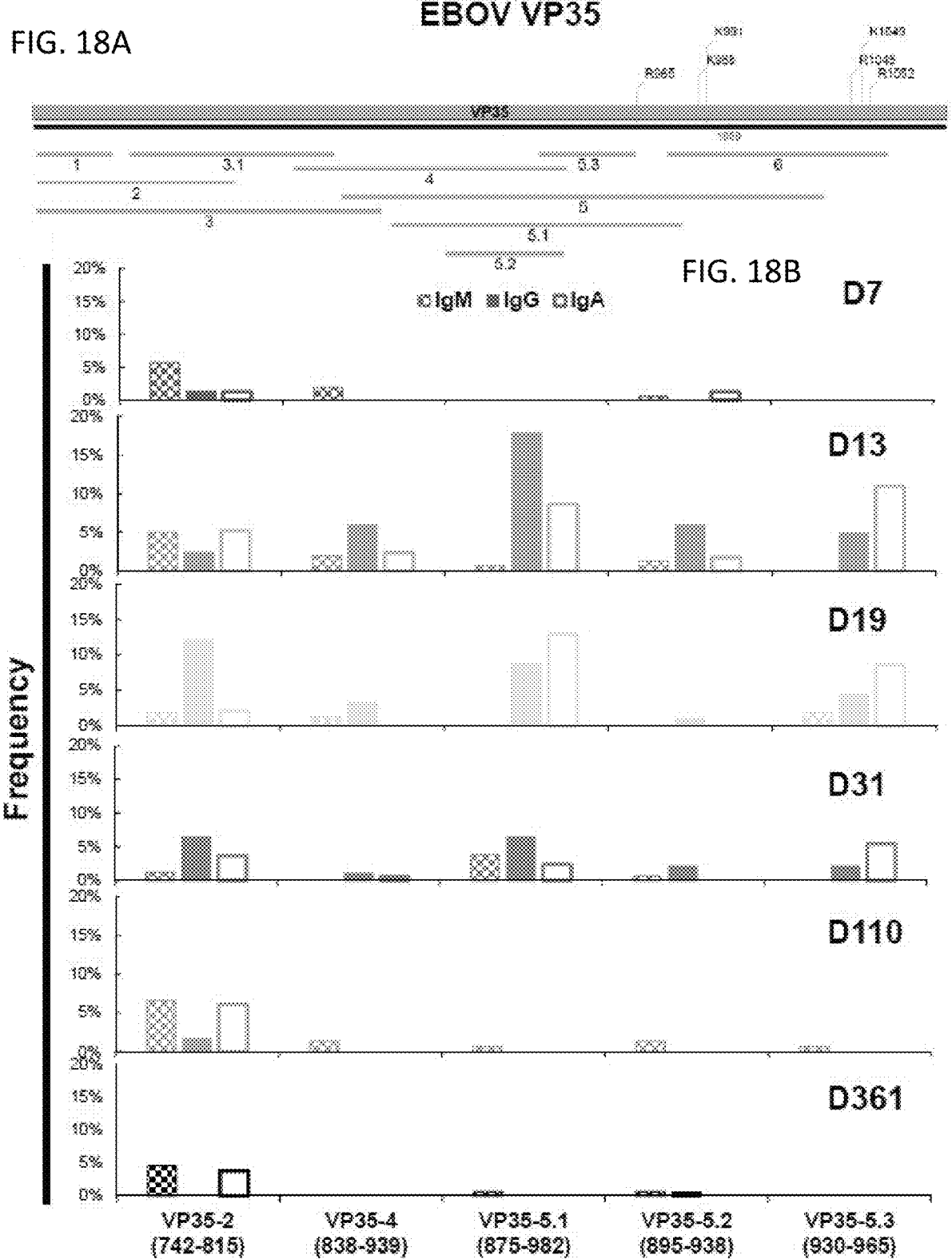

FIG. 19A EBOV VP40

FIG. 19B

Frequency

D7
D13
D19
D31
D110
D361

VP40-1 (1084-1164) | VP40-2 (1084-1266) | VP40-3 (1122-1372) | VP40-3.4 (1203-1308) | VP40-3.6 (1267-1358) | VP40-3.7 (1274-1330) | VP40-4 (1313-1387)

■ IgM ■ IgG □ IgA

EBOV VP30

FIG. 22A  EBOV VP24

FIG. 22B

FIG. 23A  FIG. 23B  FIG. 23C  FIG. 23D  FIG. 23E
NP-3 (1-101)  NP-4 (1-140)  NP-5 (1-196)  NP-5.1 (70-148)  NP-6 (83-337)
 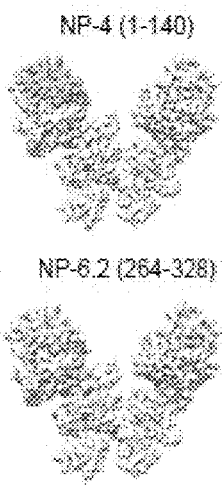 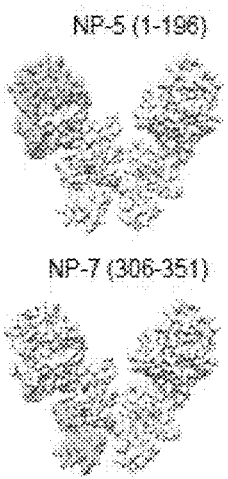 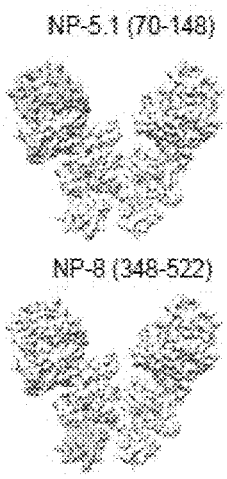 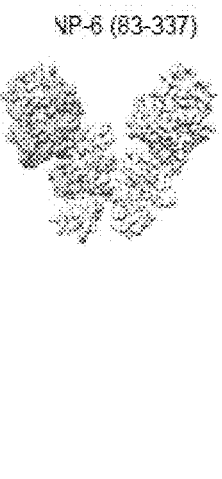
NP-6.1 (112-148)  NP-6.2 (264-328)  NP-7 (306-351)  NP-8 (348-522)
FIG. 23F  FIG. 23G  FIG. 23H  FIG. 23I
FIG. 23J
VP35-6 (978-1059)
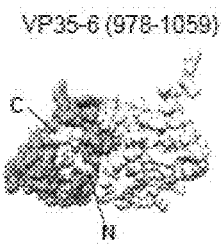
FIG. 23K  FIG. 23L  FIG. 23M  FIG. 23N  FIG. 23O
VP40-2 (1084-1266)  VP40-2.1 (1116-1156)  VP40-2.2 (1122-1242)  VP40-3 (1122-1372)  VP40-3.1 (1154-1276)
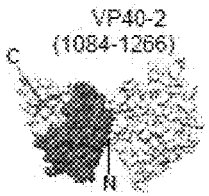 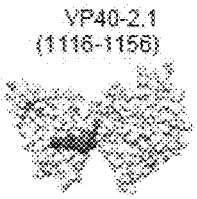   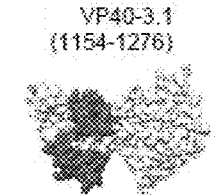
VP40-3.2 (1189-1241)  VP40-3.3 (1203-1228)  VP40-3.4 (1203-1308)  VP40-3.5 (1236-1301)
 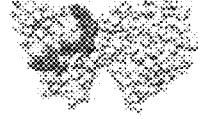  
FIG. 23P  FIG. 23Q  FIG. 23R  FIG. 23S FIG. 23T    FIG. 23U    FIG. 23V
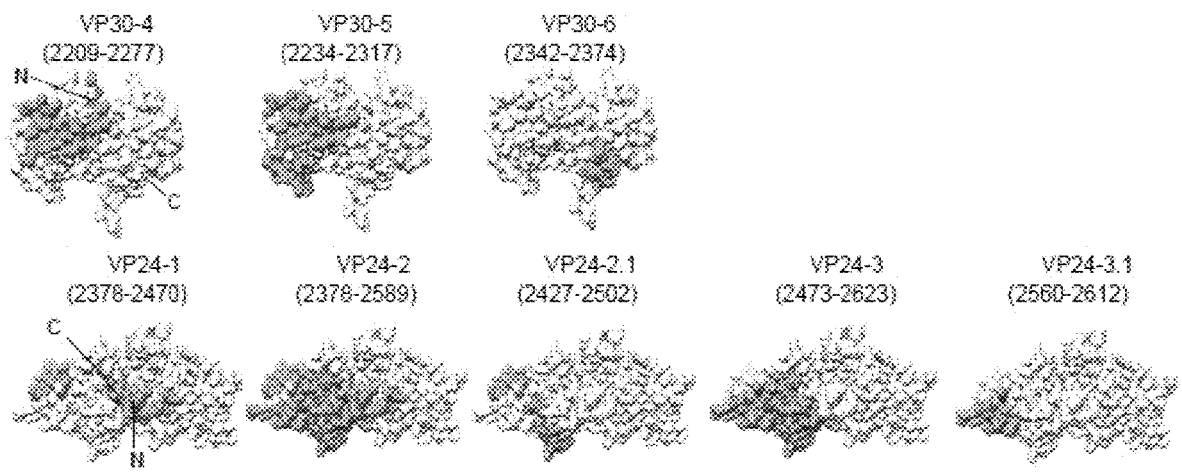
FIG. 23W    FIG. 23X    FIG. 23Y    FIG. 23Z    FIG. 23AA
FIG. 24A    FIG. 24B    FIG. 24C
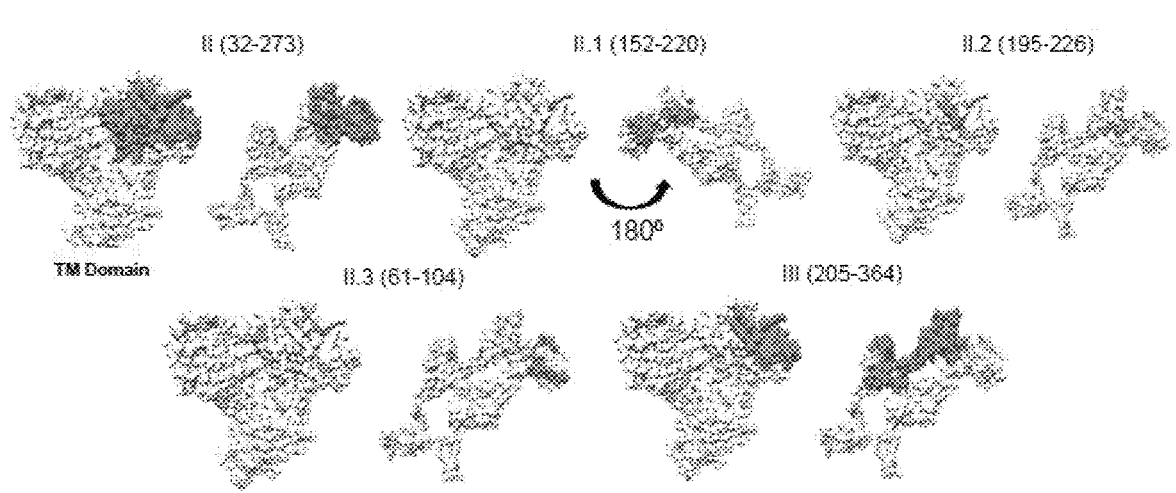
FIG. 24D    FIG. 24E FIG. 24F  FIG. 24G  FIG. 24H  FIG. 24I  FIG. 24J
GP-III.2 (232-291) 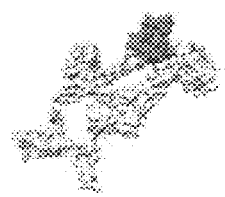  IV (267-434) 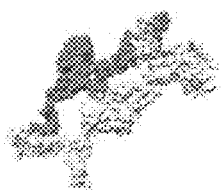  IV.1 (282-305) 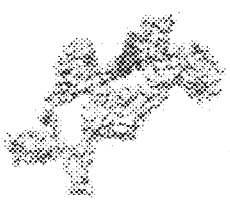  IV.3 (286-364) 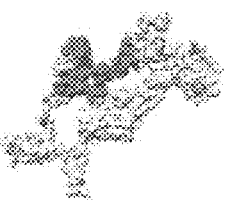  IV.6 (328-368) 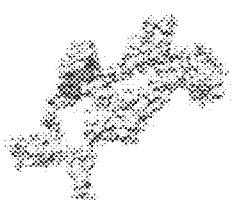
IV.8 (326-403) 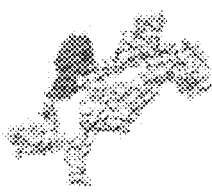  V (336-582) 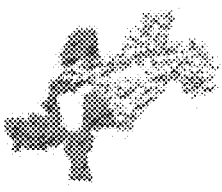  V.1 (343-368) 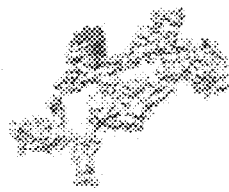  V.2 (372-420) 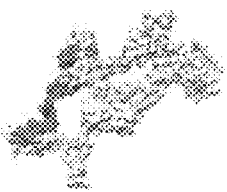  V.3 (380-491) 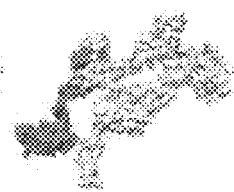
FIG. 24K  FIG. 24L  FIG. 24M  FIG. 24N  FIG. 24O
FIG. 24P  FIG. 24Q  FIG. 24R  FIG. 24S  FIG. 24T
V.4 (424-447) 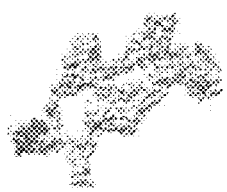  V.5 (436-491) 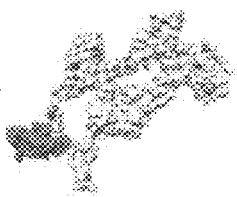  V.6 (456-484) 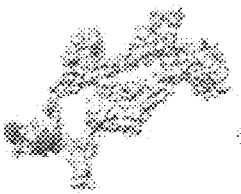  V.7 (469-498) 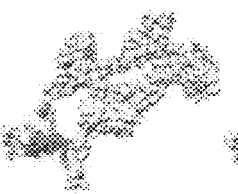  V.10 (520-547) 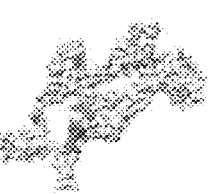
VI (617-645) 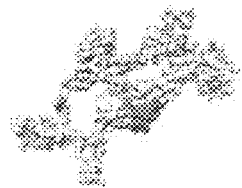  VII (430-667) 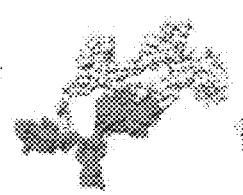  VII.1 (569-617) 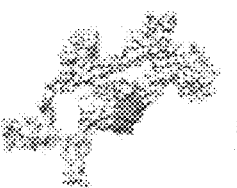  VII.2 (635-667) 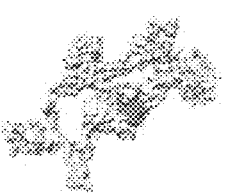
FIG. 24U  FIG. 24V  FIG. 24W  FIG. 24X

EBOV GP ELISA

PEPTIDES REPRESENTING EPITOPES FROM FILOVIRUSES

CROSS REFERENCE TO RELATED APPLICATIONS

This application claims the benefit of U.S. Provisional Application No. 62/958,612, filed Jan. 8, 2020, which is herein incorporated by reference in its entirety.

FIELD

The present disclosure relates to methods of identifying a subject with a filovirus infection, as well as to peptides and solid supports for use in such methods.

BACKGROUND

The 2014 epidemic of highly pathogenic Ebolavirus in Western Africa resulted in tens of thousands of infections and deaths. With occasional small outbreaks of new cases in West Africa and the possibility of long-term persistence of virus in some survivors, it is feared that future outbreaks can occur, resulting in severe epidemics.

Development of an effective detection assay for identifying a subject infected with Ebolavirus or other Filoviruses, including chronic Filovirus infection is a high priority, both for pre-epidemic preparedness and for rapid identification of infected individuals to control future outbreaks.

SUMMARY

Methods of identifying a subject with a Filovirus infection (such as an Ebolavirus infection) are provided herein. In some embodiments, the method comprises contacting a biological sample containing antibodies from the subject with one or more peptides comprising amino acid sequences selected from:

```
                                          (SEQ ID NO: 1)
MDSRPQKVWMTPSLTESDMDY;

(SEQ ID NO: 2)
MDSRPQKVWMTPSLTESDMDYHKILTAGLSVQQGIVRQRVI;

(SEQ ID NO: 3)
TIPDVVVDPDDGGYGEYQSYSENGMSAPDDLVLFDLDEDDEDTKPVPNR
STKGGQQKNSQKG;

(SEQ ID NO: 4)
MTTRTKGRGHTVATTQNDRMPGPELSGWISEQLMTGRIPVNDIFCDIEN
NPGLCYASQMQQTKPNPKMRNSQTQ;

(SEQ ID NO: 5)
ATAAATEAYWAEHGQPPPGPSLYEESAIRGKIESRDETVP;

(SEQ ID NO: 6)
DETVPQSVREAFNNLDSTTSLTEENFGKPDISAKDL;

(SEQ ID NO: 7)
MRRVILPTAPPEYMEAIYPARSNSTIARGGNSN;

(SEQ ID NO: 8)
MRRVILPTAPPEYMEAIYPARSNSTIARGGNSNTGFLTPESVNGDTPSN
P;

(SEQ ID NO: 9)
DLTSPEKIQAIMTSLQDFKIVPIDPTKNIMGIEVPETLVHKLTGKKVTS
KNGQPIIPVLLPKYIGLDPVAPGDLT;

(SEQ ID NO: 10)
KIVPIDPTKNIMGIEVPETLVHKLTGKKVTSKNGQPIIPVLLPKYIG;

(SEQ ID NO: 11)
KKGNSADLTSPEKIQAIMTSLQDFKIVPIDPTKNIMGIEVPETLVHK;

(SEQ ID NO: 12)
MEASYERGRPRAARQHSRDGHDHHVRA;

(SEQ ID NO: 13)
MEASYERGRPRAARQHSRDGHDHHVRARSSSRENYRGEYRQSRSASQVR
VPTVFH; and (SEQ ID NO: 14)
TQNHTIIITRTNMGFLVELQEPDKSAMNRKKPGPAKFSLLHESTLKAFT
QGSS.
```

In some examples, full-length VP35, VP40 and/or NP are used in combination with the one or more peptides.

The presence or absence of an immune complex of antibodies from the biological sample with the one or more peptides is detected. The presence of the immune complex identifies the subject as having a Filovirus infection and the absence of the immune complex identifies the subject as not having Filovirus infection.

The biological sample can be any suitable sample that contains antibodies form the subject. In some embodiments, the biological sample comprises a blood, plasma, urine, eye, serum, saliva, semen, breast milk, synovial fluid, or cerebrospinal fluid sample.

In some embodiments, the method can be used to identify a subject with a chronic Filovirus infection, such as a chronic Filovirus infection of eye, testis, synovium, or meninges tissue, or other body fluids, in the subject. In some embodiments, the method can be used to identify a Filovirus infection in a subject that was previously immunized with a Filovirus vaccine.

In some embodiments, the method further comprises treating the subject identified as having the Filovirus infection with an anti-viral agent, such as a monoclonal antibody that binds to Filovirus protein and inhibits Filovirus infection.

Also provided are methods of identifying a biological sample containing Filovirus-specific (such as Ebolavirus-specific) antibodies. In some embodiments, the method includes contacting the biological sample with one or more peptides comprising amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14, and detecting the presence or absence of an immune complex of Filovirus-specific antibodies from the biological sample with the one or more peptides. The presence of the immune complex identifies the biological sample as containing Filovirus-specific antibodies and the absence of the immune complex identifies the biological sample as not containing Filovirus-specific antibodies. In some examples, method further includes contacting the biological sample with one or more of full-length VP35, VP40 and NP to perform the diagnostic method.

Further provided are compositions that include one or more Filovirus peptides linked to a solid support, linked to a heterologous detectable label, or conjugated to a heterologous carrier. In some embodiments, the one or more peptides have amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14. In some examples, the one or more peptides are no more than 150 amino acids in length.

In additional embodiments, a peptide is provided that comprises, consists essentially of, or consists of an amino acid sequence set forth as any one of SEQ ID NOs: 1-14. In some embodiments, the peptide is no more than 150 amino acids in length. In some embodiments, the peptide is linked to a solid support or other molecule (such as a heterologous molecule).

Also provided is a method of eliciting an immune response to a Filovirus (such as an Ebolavirus) in a subject by administering an effective amount of a composition disclosed herein.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1B. Surface plasmon resonance (SPR) based analysis of human serum following Zaire ebolavirus (ZEBOV)-infection with purified ZEBOV proteins. Serial dilutions of serum samples collected at different time points from the ZEBOV survivor were analyzed for antibody binding to purified proteins from ZEBOV/Makona strain by SPR. (FIG. 1A) Polyclonal antibody affinity maturation to ZEBOV proteins following ZEBOV infection in a survivor was determined by SPR. Total antibody binding is represented in SPR resonance units (RU) in black for binding to NP, VP35, VP40, GP, sGP, VP30, VP24 and L polymerase. Total antibody binding is calculated RU for an undiluted serum sample. Binding affinity of serially diluted post-infection serum to ZEBOV proteins was measured and plotted in blue for each of the proteins as mentioned above for total antibody binding. Antibody off-rate constants that describe the fraction of antibody-antigen complexes decaying per second were determined directly from the serum sample interaction with ZEBOV proteins using SPR in the dissociation phase as described in Example 1. All SPR experiments were performed twice. The variation for each sample in duplicate SPR runs was <5%. The data shown is average value of two experimental runs. The maximum resonance units (Max RU) data shown was the calculated RU signal for the undiluted serum sample. (FIG. 1B) Antibody isotype of ZEBOV/Makona protein binding antibodies following ZEBOV infection. The isotype composition of serum antibodies bound to different proteins of the ZEBOV/Makona isolate as measured by SPR. The resonance units for each anti-Makona protein antibody isotype (IgM in black, IgG in green, and IgA in red) was divided by the total resonance units for all antibody isotypes combined to calculate the percentage of each antibody isotype for individual serum sample.

(FIG. 2A) IgM, IgG and IgA antibody epitope repertoire recognized in the ZEBOV infected sera at different days post-onset of symptoms (D7, D13, D19, D31, D110 and D361) and their alignment to the whole proteome of ZEBOV showing different proteins (NP, VP35, VP40, GP, VP30, VP24 and L). Graphical distribution of representative clones with a frequency of ≥2, obtained after affinity selection, are shown. The horizontal position and the length of the bars indicate the peptide sequence displayed on the selected phage clone to its homologous sequence in the ZEBOV proteome on alignment. The thickness of each bar represents the frequency of repetitively isolated phage, with the scale shown below the alignment. Scale value for IgM, IgG and IgA is shown enclosed in a red box beneath the respective alignments. The Gene Fragment Phage Display Library (GFPDL) affinity selection data was performed in duplicate, and similar number of phage clones and epitope repertoire was observed in both phage display analysis. (FIG. 2B) Elucidation of antibody epitope profile against the ZEBOV proteome following ZEBOV infection. Antigenic sites within the ZEBOV proteins recognized by serum antibodies following ZEBOV infection (based on data presented in FIG. 1A). The amino acid designation is based on the ZEBOV protein sequence encoded by the complete ZEBOV/Makona genome (FIG. 14). The antigenic regions/sites discovered in this study using the post-infection antibodies are depicted below the ZEBOV proteome schematic and are color coded. Epitopes of each protein are numbered in a sequential fashion indicated in black and the epitopes are color coded according to the protein color code in the proteome map.

FIGS. 4A-4D. GP binding and ZEBOV neutralization by serum antibodies generated following rabbit immunization with GFPDL selected GP antigenic site peptides. (FIG. 4A) 10-fold dilution of serum samples obtained from rabbits immunized thrice with keyhole limpet hemocyanin (KLH)-conjugated antigenic site peptides were analyzed for total binding to GP from different Ebolavirus isolates (ZEBOV/Makona, blue; ZEBOV/Mayinga, black; and Sudan virus (SUDV), red) in SPR. Total antibody binding is represented in SPR resonance units. The data shown is mean value and standard deviations of two experimental SPR runs. (FIG. 4B) Virus neutralization titers were measured against ZEBOV/Mayinga (blue bars), ZEBOV/Kikwit (green bars) and SUDV (black bars) by pseudovirion neutralization (PsVN) assay and authentic ZEBOV/Makona (red bars) in classical BSL4 based plaque reduction neutralization (PRNT). The average end-point titers (50% neutralization titers; NT50) of rabbit sera from assay run in triplicate that demonstrated virus neutralization against either of the ZEBOV strains are shown. None of the post-immunization rabbit sera neutralized empty pseudovirus, as specificity control. Pre-vaccination rabbit sera also did not neutralize any of the VSV-GPs tested in PSVN assay. (FIG. 4C) The ZEBOV-GP structure (PDB Id—3CSY) protein used for crystallography encompasses amino acid residues 33-189, 214-278, 299-310 and 502-599 of the mature 676 a.a. GP sequence with the membrane anchor shown by the trans-membrane domain (TM domain) shown at the base. (FIG. 4D) Structural representation of neutralizing/protective antigenic sites in ZEBOV-GP identified using GFPDL on the surface structures of a complete ZEBOV-GP model and solved ZEBOV-GP (PDB Id #6DZL for ZEBOV/Makona) structure wherever available. Sites that induced neutralizing antibodies (IV.1; GP 282-305, V.1; GP 343-368, V.7; GP 469-498, V.9; GP 520-547, and VI; GP 617-645) are depicted as a front view, and the antigenic sites in a monomer (chain A) are color coded according to FIG. 2. The transmembrane domain with membrane anchor base is designated by a grey bar for all structures.

FIGS. 5A-5D. GP antigenic site peptide immunization and ZEBOV challenge study in mice. (FIG. 5A) Schematic representation of mouse immunization and challenge schedule. C57Bl/6 mice (N=10 per group) were immunized intramuscularly with 20 µg of GP 282-305, GP 343-368, GP 469-498, GP 520-547, and GP 617-645 of KLH-conjugated peptides mixed with Emulsigen adjuvant, ZEBOV-GP Venezuelan equine encephalitis virus (VEEV) replicon particles (VRP) (positive control) or with KLH alone or PBS as negative controls. After the second immunization, blood was collected on day 57 (28 days after second vaccination), and sera were analyzed for antibody binding to either GP from ZEBOV/Makona (FIG. 5B) or ZEBOV/Mayinga (FIG. 5C) by SPR. The mean values with standard deviations for each group are shown. (FIG. 5D) Vaccinated mice were challenged intraperitoneally with 100 PFU of mouse-adapted ZEBOV (ma7EBOV) on day 63. ZEBOV-challenged animals were observed daily for first 14 days and every week thereafter up to 28 days following ma7EBOV infection. Mice either succumbed to viral infection or were euthanized when found to be nonresponsive. Antigenic site peptides V.7 (GP 469-498), VI (GP 617-645), peptide mix and VRP provided statistically significant protection (p<0.05) compared with the control naïve group.

FIG. 6. Serum analyses of an Ebola virus disease (EVD) patient during the first month post-symptom onset. Viral load in serum from extracted RNA was measured by RTqPCR as described (Trombley et al. Am J Top Med Hyg 2010). Lower limit of detection for each enzyme-linked immunosorbent assay (ELISA) was determined using naïve control serum and the following formula: Avg titer+(3× S.D.). For IgM, end titers for each sample are expressed as the last dilution to exceed the cut-off value for a given dilution.

FIGS. 7A-7C. Table showing antigenic regions/sites on complete ZEBOV proteome identified using GFPDL. The amino acid sequences listed in the table (from top to bottom) are set forth herein as SEQ ID NOs: 1, 2, 22-38, 4, 39-44, 6 and 45-53 (FIG. 7A); SEQ ID NOs: 54-57, 9, 58-93, 13, 94 and 95 (FIG. 7B); and SEQ ID NOs: 96-102, 14 and 103-120 (FIG. 7C).

FIG. 8. Table showing sequence similarity of GP antigenic sites with other ZEBOV strains. Amino acid sequences listed in the table are set forth herein as SEQ ID NOs: 60, 62, 67, 64, 69-75, 77-80, 83, 82, 85-87, 91, 84, 90 and 93 (from top to bottom).

FIGS. 13A-13E. IgG subclass of human serum binding to ZEBOV proteins following ZEBOV infection. The subclass of total IgG of serum antibodies bound to ZEBOV proteins are shown for serum samples collected at different time points following ZEBOV infection as measured in SPR experiment. The resonance unit for each anti-ZEBOV protein antibody IgG subclass was divided by total resonance units for total bound IgG antibodies combined for each sera and represented as a percentage.

FIGS. 14A-14E. Complete ZEBOV-Makona gene translated sequence used for construction of ZEBOV-GFPD library and depiction in FIG. 2 (SEQ ID NO: 15). Individual proteins of the complete proteome have been indicated including NP, VP35, VP40, GP, VP30, VP24, and L.

FIG. 15. Random distribution of size and sequence of the ZEBOV-GFPDL. Sequencing of Makona (2014) proteome sequences expressed by the phages of the ZEBOV GFPD libraries were aligned to the Makona (2014) proteome translated sequence (shown in FIG. 14).

FIG. 16. Anti-GP reactivity of ZEBOV convalescent plasma in ELISA before and after ZEBOV-GFPDL adsorption. Post ZEBOV infected sera (#S1) was adsorbed on Makona GFPDL coated petri dishes. Binding to recombinant ZEBOV-GP is shown before (solid purple line) and after (dashed purple line) GFPDL-adsorption in ELISA using HRP-conjugated goat anti-human IgA+IgG+IgM specific antibody.

FIGS. 17A-17B. Antigenic sites in ZEBOV-NP identified using GFPDL analysis. (FIG. 17A) Map of NP protein of ZEBOV depicting various antigenic sites in yellow from 1-12 and different NP domains (D1, D2 and L). NP D1 spans 1-450 aa and aids in NP-NP interaction. NP D2 spans 451-600 aa and plays a role in viral replication. L signifies last 50 aa and is the L domain aiding in viral assembly and budding. (FIG. 17B) Distribution of ZEBOV NP phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with clonal frequency of ≥5% are shown.

FIGS. 18A-18B. Antigenic sites in ZEBOV-VP35 identified using GFPDL analysis. (FIG. 18A) Map of VP35 protein of ZEBOV depicting various antigenic sites in orange 1-6. Residues playing a role in polymerase cofactor function (R965, K991 and K988) and those playing a role in immune suppression (R1045, K1049 and R1052) are depicted. (FIG. 18B) Distribution of ZEBOV VP35 phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with a clonal frequency of ≥5% are shown.

FIGS. 19A-19B. Antigenic sites in ZEBOV-VP40 identified using GFPDL analysis. (FIG. 19A) Map of VP40 protein of ZEBOV depicting antigenic sites in purple from 1-5 and residue Y1096 playing a role in viral replication. VP40 D1 spans residues 1296-1409 binds to liposomes and L signifies the VP40 L domain responsible for VLP assembly and budding (residues 1295-KLR-1297). (FIG. 19B) Distribution of ZEBOV VP40 phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with a clonal frequency of ≥5% are shown.

FIGS. 20A-20B. Antigenic sites in ZEBOV-GP identified using GFPDL analysis. (FIG. 20A) Map of GP protein of ZEBOV depicting antigenic sites in green from I-VII.2. Various peptide regions of GP are abbreviated; SP: signal peptide, RBR: receptor-binding region, MLD: mucin-like domain, FP: fusion peptide, HR1: heptad Residues on the GP1 chalice contacting residues F503, F504 and Y506 on the protruding loop 2 of NPC1 have been marked with * (V1490, P1491), # (W1497, G1498, F1499), & (L1522, E1523, I1524), @ (V1522, S1553, G1554, T1555, G1556, P1557) or indicated on the sequence (T1494, A1563, 11581). (FIG. 20B) Distribution of ZEBOV GP phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with a clonal frequency of ≥5% are shown.

FIGS. 21A-21B. Antigenic sites in ZEBOV-VP30 identified using GFPDL analysis. (FIG. 21A) Map of VP30 protein of ZEBOV depicting antigenic sites in cyan from 1-6. Two serine clusters S1 (2116-2118 aa) and S2 (2129-2133 aa and 2159-2177 aa) phosphorylated for transcription are shown. The map also shows a Cys3-His zinc binding motif crucial for transcription and RNA binding activity. (FIG. 21B) Distribution of ZEBOV VP30 phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with a clonal frequency of ≥5% are shown.

FIGS. 22A-22B. Antigenic sites in ZEBOV-VP24 identified using GFPDL analysis. (FIG. 22A) Map of VP24 of ZEBOV depicting antigenic sites in pink from 1-3.1. Map also indicates IID (2403-2427 aa and 2519-2523 aa) and the L domain (2529-2522 aa) responsible for viral assembly and budding. (FIG. 22B) Distribution of ZEBOV VP24 phage clones and frequency of phage clones binding IgM (checkered box pattern), IgG (filled box) and IgA (empty box) antibodies for each antigenic site isolated using GFPDL against serum samples at Day 7 (magenta), 13 (orange), 19 (yellow), 31 (blue), 110 (green) and 361 (black). The number of clones encoding each antigenic site was divided by the total number of ZEBOV GFPDL-selected clones for each serum sample to calculate frequency. Only antigenic sites with a clonal frequency of ≥5% are shown.

FIGS. 23A-23AA. Structured representation of antigenic sites identified in various ZEBOV proteins using GFPDL. (FIGS. 23A-23I) Antigenic sites in NP protein of ZEBOV are depicted in yellow on the surface structure of NP PDB #6C54 (Sites of NP displayed on PDB #6C54 Su et al., (2018) Cell 172: 966-978), which encompasses residues 39-385. (FIG. 23J) Antigenic site (VP35-6) in the PDB #3FKE (Sites of VP35 displayed in PDB #3FKE Leung et al., (2009) PNAS 106 (2) 411-416), which only encompasses the interferon inhibitory domain (IID). (FIGS. 23K-23S) Antigenic sites in VP40 protein of ZEBOV are depicted in purple on the surface structure of NP PDB #4LDD (Sites of VP40 displayed on PDB #4LDD Bornholdt et al., (2013) Cell 154, 763-774), which encompasses residues 1129-1353. (FIGS. 23T-23V) Antigenic sites in the VP30 protein of ZEBOV are depicted in cyan on the surface structure of NP PDB #2I8B (Sites of VP30 displayed on PDB #2I8B Hartlieb et al., (2007) PNAS 104 (2) 624-629), which encompasses residues 2227-2353. (FIGS. 23W-23AA) Antigenic sites in VP24 protein of ZEBOV are depicted in pink on the surface structure of NP PDB #4MOQ (Sites of VP24 displayed on PDB #4MOQ Edwards et al., (2014) Cell Rep 6: 1017-1025), which encompasses residues 2387-2608. The N-terminal (N-) and C-terminal (C-) are depicted within the first structure for each ZEBOV protein.

FIG. 24A-24X. Structural representations of antigenic sites on the surface structure of a complete ZEBOV/Makona GP model (ITASSER (Yang, J. et al. The I-TASSER Suite: protein structure and function prediction. Nat. Methods 12, 7-8 (2015), right) and solved ZEBOV/Makona GP structure (PDB #6DZL (Murin, C. D. et al. Cell Rep, 24, 2723-2732 (2018)) are shown where available; antigenic sites in a monomer (chain A) are colored green. The ZEBOV GP structure used for crystallography encompasses amino acid residues 33-189, 214-278, 299-310 and 502-599 of the mature 676-aa GP sequence. All sites are shown in the model in the rear view (FIGS. 24A and 24C-24X) except Site II.1 (FIG. 24B). All sites are depicted in front view on the solved structure (PDB #6DZL) (FIGS. 24A-24E).

FIG. 26. Alignment of glycoprotein (GP) sequences from ZEBOV/Makona (2014) (SEQ ID NO: 18), ZEBOV/Mayinga (1976) (SEQ ID NO: 121), ZEBOV/Kikwit (1995) (SEQ ID NO: 122), Bundibugyo virus (BDBV; SEQ ID NO: 123), and SUDV (SEQ ID NO: 124).

FIG. 28. Anti-GP reactivity of post-immunization mouse sera. Post-first (prime) and second (boost) vaccination sera from mice immunized with KLH conjugated antigenic site peptides were evaluated to ZEBOV GP binding antibodies in ELISA. Binding to recombinant ZEBOV-GP is shown after prime (black) and after boost (red) vaccination in ELISA using HRP-conjugated anti-mouse IgG specific antibody. The mean values with standard deviations for each group are shown.

SEQUENCE LISTING

Figure 2A:
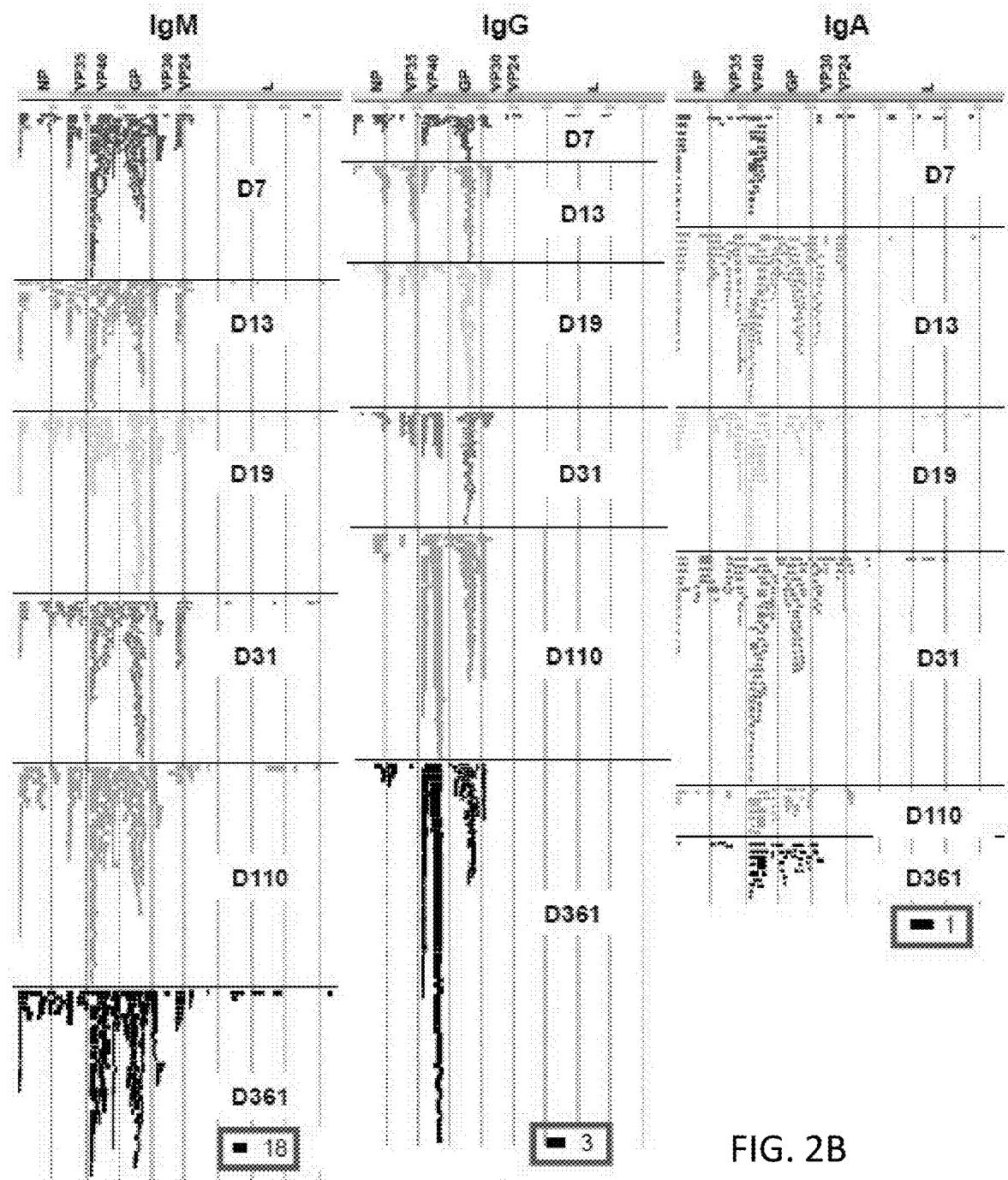
FIGS. 2A-2B. IgM, IgG and IgA antibody repertoires elicited in a severely ill survivor after ZEBOV infection.

The amino acid sequences listed in the accompanying sequence listing are shown using standard three letter code for amino acids, as defined in 37 C.F.R. 1.822. The Sequence Listing is submitted as an ASCII text file, created on Jan. 3, 2021, 158 KB, which is incorporated by reference herein. In the accompanying sequence listing:

SEQ ID NOs: 1-14 are amino acid sequences of Filovirus peptides (see Table 1).

SEQ ID NO: 15 is the amino acid sequence of ZEBOV/Makona NP.

SEQ ID NO: 16 is the amino acid sequence of ZEBOV/Makona VP35.

SEQ ID NO: 17 is the amino acid sequence of ZEBOV/Makona VP40.

SEQ ID NO: 18 is the amino acid sequence of ZEBOV/Makona GP.

SEQ ID NO: 19 is the amino acid sequence of ZEBOV/Makona VP30.

SEQ ID NO: 20 is the amino acid sequence of ZEBOV/Makona VP24.

SEQ ID NO: 21 is the amino acid sequence of ZEBOV/Makona L.

SEQ ID NOs: 22-120 are amino acid sequences of ZEBOV antigenic sites (FIGS. 7A-7C).

SEQ ID NO: 121 is the amino acid sequence of ZEBOV/Mayinga (1976) GP.

SEQ ID NO: 122 is the amino acid sequence of ZEBOV/Kikwit (1995) GP.

SEQ ID NO: 123 is the amino acid sequence of Bundibugyo virus GP.

SEQ ID NO: 124 is the amino acid sequence of Sudan virus GP.

DETAILED DESCRIPTION

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of an active agent into a subject by a chosen route. Administration can be local or systemic. For example, if the chosen route is intravenous, the agent is administered by introducing the agent into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody: An immunoglobulin, antigen-binding fragment, or derivative thereof, that specifically binds and recognizes an analyte (antigen). The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof that retain binding affinity for the antigen. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen.

Avidin/Streptavidin: The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NeutrAvidin Biotin Binding Protein (available from Pierce Biotechnology) with a mass of approximately 60,000 daltons.

The avidin-biotin complex is the strongest known non-covalent interaction ($Ka=10^{15}$ $M^{-1}$) between a protein and ligand. The bond formation between biotin and avidin is very rapid, and once formed, is unaffected by extremes of pH, temperature, organic solvents and other denaturing agents.

Although examples disclosed herein use streptavidin as a specific binding agent, the streptavidin could be substituted with other types of avidin. The term "avidin" is meant to refer to avidin, streptavidin and other forms of avidin (such as derivatives or analogs thereof) that have similar biotin binding characteristics. Analogs or derivatives of avidin/streptavidin include, but are not limited to, nitro-streptavidin, non-glycosylated avidin, N-acyl avidins (such as N-acetyl, N-phthalyl and N-succinyl avidin), and the commercial products ExtrAvidin™ (Sigma-Aldrich), Neutralite Avidin (SouthernBiotech) and CaptAvidin (Invitrogen). Additional avidin/streptavidin analogs and derivatives are known in the art (see, for example, U.S. Pat. No. 5,973,124 and U.S. Patent Application Publication Nos. US 2004/0191832; US 2007/0105162; and US 2008/0255004).

Biological sample: A sample obtained from a subject. Biological samples include all clinical samples useful for detection of disease or infection (for example, EVD or ZEBOV infection) in subjects, including, but not limited to, cells, tissues, and bodily fluids, such as blood, derivatives and fractions of blood (such as serum or plasma), cerebrospinal fluid, urine, eye tissue, saliva, semen, breast milk, synovial fluid; as well as biopsied or surgically removed tissue, for example tissues that are unfixed, frozen, or fixed in formalin or paraffin. In a particular example, a biological sample is obtained from a subject having or suspected of having a Filovirus infection.

Biotin: A molecule (also known as vitamin H or vitamin $B_7$) that binds with high affinity to avidin and streptavidin. Biotin is often used to label nucleic acids and proteins for subsequent detection by avidin or streptavidin linked to a detectable label, such as a fluorescent or enzymatic reporter molecule. Biotinylation of a molecule (such as a peptide) is routinely achieved in the art by reacting a free carboxyl group on biotin with an amine group on a protein, such as an amine group found in an antibody or protein analyte/ analog. Unless indicated otherwise, the term "biotin" includes derivatives or analogs that participate in a binding reaction with avidin. Biotin analogs and derivatives include, but are not limited to, N-hydroxysuccinimide-iminobiotin (NHS-iminobiotin), amino or sulfhydryl derivatives of 2-iminobiotin, amidobiotin, desthiobiotin, biotin sulfone, caproylamidobiotin and biocytin, biotinyl-ε-aminocaproic acid-N-hydroxysuccinimide ester, sulfo-succinimide-iminobiotin, biotinbromoacetylhydrazide, p-diazobenzoyl biocytin, 3-(N-maleimidopropionyl) biocytin, 6-(6-biotinamido-hexanamido)hexanoate and 2-biotinamidoethanethiol. Biotin derivatives are also commercially available, such as DSB-X™ Biotin (Invitrogen). Additional biotin analogs and derivatives are known in the art (see, for example, U.S. Pat. No. 5,168,049; U.S. Patent Application Publication Nos. 2004/0024197, 2001/0016343, and 2005/0048012; and PCT Publication No. WO 1995/007466).

Carrier: An immunogenic molecule to which a peptide can be linked to enhance an immune response to the peptide. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached. In one example, the carrier is keyhole limpet hemocyanin (KLH).

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual*, $2^{nd}$ ed. Cold Spring Harbor Publications, New York (2013) for a description of immunoassay formats and conditions. The conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (for example, from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

In several embodiments, the formation of an immune complex can be detected through conventional methods, for instance immunohistochemistry, immunoprecipitation, flow cytometry, immunofluorescence microscopy, ELISA, immunoblotting (for example, Western blot), point-of-care test, rapid assay, flow assay, bead-based assay, nitrocellulose/PVDF membrane based assay, magnetic resonance imaging, CT scans, X-ray, affinity chromatography, biosensors, luminescence, fluorescence, etc.

Conjugate: A complex of at least two heterologous molecules linked together. In a non-limiting example, a Filovirus peptide as disclosed herein is conjugated to a solid support by a linker. In another non-limiting example, a Filovirus peptide as disclosed herein is conjugated to a protein carrier by a linker.

Consists essentially of and Consists Of: A peptide that consists essentially of a specified amino acid sequence does not include any additional amino acid residues. However, the residues in the peptide can be modified to include non-peptide components, such as labels (for example, fluorescent, radioactive, or solid particle labels), sugars or lipids, and the N- or C-terminus of the polypeptide can be joined (for example, by peptide bond) to heterologous amino acids, such as a cysteine (or other) residue in the context of a linker for conjugation chemistry. A peptide that consists of a specified amino acid sequence does not include any additional amino acid residues, nor does it include additional biological components, such as nucleic acids, lipids, sugars, nor does it include labels.

Contacting: Placement in direct physical association; includes both in solid and liquid form, which can take place either in vivo or in vitro. Contacting includes contact between one molecule and another molecule, for example the amino acid on the surface of one peptide, such as an antigen, that contacts a polypeptide, such as an antibody.

Control: A reference standard. In some embodiments, the control is a negative control, such as sample obtained from a healthy patient not infected with Filovirus. In other embodiments, the control is a positive control, such as a biological sample obtained from a patient diagnosed with Filovirus infection. In still other embodiments, the control is a historical control or standard reference value or range of values (such as a previously tested control sample, such as a group of Filovirus patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, biopsy, body fluids, and analysis of biological samples obtained from a subject. In one example, diagnosis of a subject as having a Filovirus infection comprises determining whether the subject has antibodies that specifically bind to one or more peptides listed in Table 1.

Ebolavirus: A genus of enveloped, non-segmented, negative-sense, single-stranded RNA viruses that cause Ebolavirus disease (EVD), formerly known as Ebola hemorrhagic fever (EHF), in humans. Ebolaviruses spread through human-to-human transmission, with infection resulting from direct contact with blood, secretions, organs or other bodily fluids of infected people, and indirect contact with environments contaminated by such fluids. These may include other Filoviruses.

The symptoms of Ebolavirus infection and EVD are well-known. Briefly, in humans, Filovirus has an initial incubation period of 2 to 21 days (7 days on average, depending on the species) followed by a rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms related to hemorrhagic fever occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. Death can occur 6 to 16 days after the onset of symptoms. People are infectious as long as their blood and secretions contain the virus, which in some instances can be more than 60 days.

Immunoglobulin M (IgM) antibodies to the virus appear 2 to 9 days after infection whereas immunoglobulin G (IgG) antibodies appear approximately 7 to 25 days after infection, which coincides with the recovery phase. In survivors of EVD, both humoral and cellular immunity are detected, however, their relative contribution to protection is unknown.

Five distinct species of Ebolavirus are known, including Bundibugyo ebolavirus (BDBV), Reston ebolavirus (RESTV), Sudan ebolavirus (SUDV), Taï Forest ebolavirus (TAFV), and Zaire ebolavirus (ZEBOV). Bundibugyo ebolavirus, Sudan ebolavirus, and Zaire ebolavirus have been associated with large outbreaks of EVD in Africa and reported case fatality rates of up to 90%.

The Ebolavirus genome includes about 19 kb, which encode seven structural proteins including NP (a nucleoprotein), VP35 (a polymerase cofactor), VP30 (a transcriptional activator), VP24, L (a RNA polymerase), and GP (a glycoprotein).

Ebolavirus glycoprotein (GP): The virion-associated transmembrane glycoprotein of Ebolavirus is initially synthesized as a precursor protein of about 676 amino acids in size, designated $GP_0$. Individual $GP_0$ polypeptides form a homotrimer and undergo glycosylation as well as processing to remove the signal peptide, and cleavage by a cellular protease between approximately positions 501/502 to generate separate $GP_1$ and $GP_2$ polypeptide chains, which remain associated via disulfide bonds as $GP_1/GP_2$ protomers within the homotrimer. The extracellular $GP_1$ trimer (approximately 140 kDa) is derived from the amino-terminal portion of the $GP_0$ precursors, and the $GP_2$ trimer (approximately 26 kDa), which includes extracellular, transmembrane, and cytosolic domains, is derived from the carboxyl-terminal portion of the $GP_0$ precursors. $GP_1$ is responsible for attachment to new host cells while $GP_2$ mediates fusion with those cells.

Comparisons of the predicted amino acid sequences for the GPs of the different ebolaviruses show conservation of amino acids in the amino-terminal and carboxy-terminal regions with a highly variable region in the middle of the protein (Feldmann et al., Virus Res. 24: 1-19, 1992; see also FIG. 26). The GPs of the ebolaviruses are highly glycosylated and contain both N-linked and O-linked carbohydrates that contribute up to 50% of the molecular weight of the protein. Most of the glycosylation sites are found in the central variable region of GP.

Effective amount: An amount of agent, such as an antiviral agent, that is sufficient to generate a desired response, such as an inhibition of viral infection in a subject or detection of a particular viral infection in a subject. For instance, this can be the amount necessary to inhibit an infection with one or more ebolaviruses or to measurably alter outward symptoms of the infection. In some embodiments, an effective amount is an amount of a peptide that is sufficient for detection of antibodies to the peptide in a biological sample from a subject.

In one example, a desired response is to induce an immune response that elicits an immune response to filovirus in a subject and/or inhibits or prevents filovirus infection in a subject. For example, administration of an effective amount of a disclosed filovirus peptide can induce an immune response in a subject that inhibits subsequent infection of the subject by the filovirus.

Epitope: An antigenic determinant. These are particular chemical groups or peptide sequences on a molecule that are antigenic (for example, sequences that elicit or recognize a specific immune response). An antibody specifically binds a particular antigenic epitope on a polypeptide.

Filovirus: A family of enveloped, non-segmented, negative-sense, single-stranded RNA viruses that cause viral hemorrhagic fever (such as Ebolavirus disease, EVD) in humans. The Filovirus family contains several genera, including Ebolavirus, Marburgvirus, Cuevavirus, and Dianlovirus. Filoviruses spread through human-to-human transmission, with infection resulting from direct contact with blood, secretions, organs or other bodily fluids of infected people, and indirect contact with environments contaminated by such fluids. These may include other Filoviruses.

The symptoms of filovirus infection and viral hemorrhagic fever are well-known and vary depending on the particular infectious agent. Briefly, in humans, filovirus has an initial incubation period of 2 to 21 days (7 days on average, depending on the species) followed by a rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms may occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. People are infectious as long as their blood and secretions contain the virus, which in some instances can be more than 60 days.

The filovirus genome is about 19 kb in length, and includes seven genes including NP (a nucleoprotein), VP35 (a polymerase cofactor), VP30 (a transcriptional activator), VP24, L (a RNA polymerase), and GP (a glycoprotein).

Heterologous: Originating from a separate genetic source or species. For example, a heterologous protein (such as a carrier protein) refers to a protein derived from a different source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to treatment of a subject with a "prime" immunogen to induce an immune response that is subsequently "boosted" with a boost immunogen. Together, the prime and boost immunizations produce the desired immune response in the subject. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immune complex: The binding of antibody to an antigen forms an immune complex. In some embodiments, the formation of an immune complex can be detected through conventional methods, for instance immunodetection, immunohistochemistry, immunoprecipitation, flow cytometry, immunofluorescence microscopy, ELISA, immunoblotting (for example, Western blot), magnetic resonance imaging, CT scans, X-ray, biosensors, affinity chromatography, etc.

Inhibiting a disease or condition: Reducing the full development of a disease or condition in a subject, for example, reducing the full development of filovirus disease in a subject who has a filovirus infection, and/or reducing filovirus infection in a subject or population of subjects at risk thereof. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example, by vaccinating a subject at risk of filovirus infection, but not infected by filovirus, with an filovirus peptide as disclosed herein) that reduces subsequent development of the disease or condition, and also to amelioration of one or more signs or symptoms of the disease or condition following development. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters well known in the art that are specific to the particular disease or condition.

In some embodiments, an immune response elicited by administering an effective amount of an filovirus peptide as disclosed herein inhibits infection of a human subject by the filovirus, for example, by at least 50% (such as at least 60%, at least 70%, at least 80%, at least 90%, or more) compared to a suitable control.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Label or Detectable label: A detectable compound that is conjugated directly or indirectly to another molecule, such as a peptide or antibody, to facilitate detection of that molecule. For example, the label can be capable of detection by any method including ELISA, spectrophotometry, flow cytometry, or microscopy. Specific, non-limiting examples of labels include fluorophores, chemiluminescent agents, enzymatic linkages, radioactive isotopes or a member of a specific binding pair (such as biotin and avidin/streptavidin). Non-limiting methods for labeling and guidance in the choice of labels appropriate for various purposes are discussed for example in Green and Sambrook (*Molecular Cloning: A Laboratory Manual,* $4^{th}$ ed., New York: Cold Spring Harbor Laboratory Press, 2012) and Ausubel et al. (Eds.) (*Current Protocols in Molecular Biology*, New York: John Wiley and Sons, 2017).

Lateral flow device: A device that absorbs or adsorbs a liquid sample (such as a serum or plasma sample), routes that liquid sample to a detection zone, and uses detection methods (such as peptide—or antibody-based detection methods) to generate a visible signal in response to the presence or absence of a specific molecule (such as an antibody specific for a peptide of interest). The device can be a test strip used in lateral flow chromatography, in which a test sample fluid, suspected of containing an analyte (such as an antibody that specifically binds to one or more of the peptides listed in Table 1), flows (for example by capillary action) through the strip (which is frequently made of bibulous materials such as paper, nitrocellulose, and cellulose). The test fluid and any suspended analyte can flow along the strip to a detection zone in which the analyte (if present) interacts with a detection agent to indicate a presence, absence and/or quantity of the analyte.

Many lateral flow devices are one-step lateral flow assays in which a biological fluid is placed in a sample area on a bibulous strip (though, non-bibulous materials can be used, and rendered bibulous by applying a surfactant to the material), and allowed to migrate along the strip until the liquid comes into contact with a specific binding partner (such as one or more of the peptides listed in Table 1) that interacts with an analyte (such as an antibody that binds to one or more of the peptides listed in Table 1) in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

Linked: The term "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g. electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker". In several embodiments, linked components are associated in a chemical or physical manner so that the components are not freely dispersible from one another, at least until contacting or entering a cell, such as an immune cell.

Linker: One or more molecules or groups of atoms positioned between two moieties. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In several embodiments, a peptide linker can be used to link the C-terminus of a first protein to the N-terminus of a second protein. Non-limiting examples of peptide linkers include glycine-serine peptide linkers, which are typically not more than 10 amino acids in length. Typically, such linkage is accomplished using molecular biology techniques to genetically manipulate DNA encoding the first polypeptide linked to the second polypeptide by the peptide linker.

Peptide: A chain of amino acids, typically less than 150 amino acids in length, such as 50-100 amino acids in length. The residues in a peptide can include post-translational or secondary modifications, such as glycosylation, sulfation or phosphorylation, as well as chemical modifications. "Peptide" applies to naturally occurring amino acid polymers and non-naturally occurring amino acid polymers, including amino acid polymers in which one or more amino acid residues are non-natural amino acids. A "residue" refers to an amino acid or amino acid mimetic incorporated in a peptide by an amide bond or amide bond mimetic. A peptide has an amino terminal (N-terminal) end and a carboxy terminal (C-terminal) end.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid. In some embodiments, a peptide is at most 150 amino acids in length, such as at most 100 amino acids in length, such as at most 75 amino acids in length, such as at most 50 amino acids in length or at most 40 amino acids in length for example.

Peptide Modifications: Synthetic embodiments of the peptides described herein are also provided. For example, peptides can be modified by a variety of chemical techniques to produce derivatives having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Any suitable method may be used to introduce cyclic structures into the disclosed peptides to select and provide conformational constraints to the structure that result in enhanced stability.

Each peptide of this disclosure is comprised of a sequence of amino acids, which may be either L- and/or D-amino acids, naturally occurring and otherwise.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed peptides and compositions.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired anti-Filovirus immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Prime-boost immunization: An immunotherapy including administration of multiple immunogens over a period of time to elicit the desired immune response.

Solid support: Any material which is insoluble or can be made insoluble by a subsequent reaction. Numerous and varied solid supports are known to those in the art and include, without limitation, nitrocellulose, the walls or wells of a reaction tray, multi-well plates, test tubes, polystyrene (e.g., polystyrene beads), polyvinyl (e.g., polyvinyl beads), magnetic beads, membranes, hydrogel, and microparticles (such as latex particles). Any suitable porous material with sufficient porosity to allow access by detector reagents and a suitable surface affinity to immobilize capture reagents (e.g., peptides or antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described herein can be in the form of sheets or strips.

The surface of a solid support may be activated by chemical processes that cause covalent linkage of an agent (e.g., a peptide or antibody) to the support. However, any other suitable method may be used for immobilizing an agent (e.g., a peptide or antibody) to a solid support including, without limitation, ionic interactions, hydrophobic interactions, covalent interactions and the like. The particular forces that result in immobilization of an agent on a solid phase are not important for the methods and devices described herein.

A solid phase can be chosen for its intrinsic ability to attract and immobilize an agent, such as a capture reagent (such as an antibody or peptide). Alternatively, the solid phase can possess a factor that has the ability to attract and immobilize an agent, such as a capture reagent. The factor can include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow support" is a solid support that is useful in a lateral flow device.

Specifically bind: When referring to the formation of an antibody:antigen protein complex, or a protein:protein complex, refers to a binding reaction which determines the presence of a target protein, peptide, or polysaccharide, in the presence of a heterogeneous population of proteins and other biologics. Thus, under designated conditions, a particular antibody or protein binds preferentially to a particular target protein, peptide or polysaccharide and does not bind in a significant amount to other proteins or polysaccharides present in the sample or subject. Specific binding can be determined by standard methods. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Subject: Living multi-cellular vertebrate organisms, a category that includes human and non-human mammals. In an example, a subject is a human. In an additional example, a subject is selected that is at risk of or suspected of having a Filovirus infection, such as an Ebolavirus infection.

Treating or preventing a disease: "Preventing" a disease refers to inhibiting the full development of a disease, for example in a person who is known to have a predisposition to a disease such as an Ebolavirus infection or EVD. "Treating" refers to a therapeutic intervention that ameliorates a sign or symptom of a disease or pathological condition after it has begun to develop. "Ameliorating" refers to the reduction in the number or severity of signs or symptoms of a disease, such as cancer. In several embodiments, treatment refers to a reduction in viral load and/or an improvement of one or more symptoms of a Filovirus infection.

Under conditions sufficient for: A phrase that is used to describe any environment that permits a desired activity.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen (such as a Filovirus0, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with Filovirus infection and/or decreases the viral load compared to a control. In another non-limiting example, a vaccine reduces Filovirus infection compared to a control.

II. Methods of Detection and Diagnosis

Provided herein is a method of identifying a subject with a Filovirus infection based on the detection of antibodies in the subject that bind to particular epitopes of Filovirus proteins. As discussed in the examples, the epitopes are highly conserved among filoviruses and the presence of antibodies in a subject targeting these epitopes is unexpectedly superior for identification of a subject with a Filovirus infection. In one example, the presence of Filovirus (for example, Zaire ebolavirus) is detected in a biological sample from a subject, and can be used to identify a subject with a filovirus infection. The method can include contacting a sample with an isolated filovirus peptide as disclosed herein and under conditions sufficient to form an immune complex between the peptide and the antibodies in the sample, and detecting the immune complex. In some examples, full-length VP35, VP40 and/or NP are used in combination with the one or more peptides.

The method can be performed with a biological sample from any suitable subject, such as a subject at risk of or suspected of having a Filovirus infection, for example a ZEBOV infection. In some embodiments, the method is performed with a biological sample from a subject at risk of or suspected of having a Filovirus infection, for example a ZEBOV infection. In some embodiments, the method is performed with a biological sample from a subject who has a history of Filovirus disease, but has recovered and does not have any symptoms of the disease at the time the sample is obtained. In some embodiments, the method is performed with a biological sample from a subject who does not have acute Filovirus disease or symptoms, but is at risk of or suspected of having a Filovirus infection, for example a ZEBOV infection.

In some embodiments, the method is performed with a biological sample from a subject who was previously immunized with a Filovirus vaccine, such as an Ebolavirus vaccine, for example, a ZEBOV vaccine. In some embodiments, the method is performed with a biological sample from a subject who was previously immunized with a Filovirus GP vaccine, such as an Ebolavirus GP vaccine, for example, a ZEBOV GP vaccine.

The biological sample can be any suitable sample from a subject that contains antibodies. For example, a blood, plasma, urine, eye, serum, saliva, semen, breast milk, synovial fluid, or cerebrospinal fluid, or sputum sample.

In some embodiments, detection of antibodies in the biological sample that specifically bind to the peptides comprising Filovirus epitopes described herein identifies the subject as having a Filovirus infection, such as a ZEBOV infection. In some embodiments, detection of the absence of antibodies in the biological sample that specifically bind to the peptides comprising Filovirus epitopes described herein identifies the subject as not having a Filovirus infection, such as a ZEBOV infection. Depending on the subject and the sample, the Filovirus infection may be, for example, an acute or chronic infection.

In some embodiments, detection of antibodies in the biological sample that specifically bind to the peptides comprising Filovirus epitopes described herein indicates that the subject has an acute Filovirus infection if the subject has no prior history of Filovirus infection.

In some embodiments, detection of antibodies in the biological sample that specifically bind to the peptides comprising Filovirus epitopes described herein indicates that the subject has a chronic Filovirus infection if the subject has a history of Filovirus infection, but no longer has symptoms of acute infection.

In some embodiments, detection of antibodies in the biological sample that specifically bind to the peptides comprising Filovirus epitopes described herein indicates that the subject has a chronic Filovirus infection if the subject has a history of Filovirus infection, but no longer has symptoms of acute infection, and the biological sample is an eye, semen, breast milk, synovial fluid, cerebrospinal fluid, body fluid, or meninges sample. In some embodiments, detection of antibodies in the biological sample that specifically bind to the peptides comprising Filovirus epitopes described herein indicates that the subject has a chronic Filovirus infection if the subject has a history of Filovirus infection, but no longer has symptoms of acute infection, and the biological sample is from immune privileged tissue in the subject, such as eye, testis, synovium, cerebrospinal fluid, or meninges tissue.

The Filovirus infection detected using the disclosed method can be any type of Filovirus infection. In some embodiments, the disclosed method is used to identify the presence or absence of an Ebolavirus infection. In some embodiments, the disclosed method is used to identify the presence or absence of a ZEBOV, SUDV, RESTV, TAFV, MARV, or BDBV infection.

In some embodiments, the method comprises contacting a biological sample containing antibodies from the subject with one or more peptides selected from those shown in Table 1, and detecting the presence or absence of an immune complex of antibodies from the biological sample with the one or more peptides. The presence of the immune complex identifies the subject as having a Filovirus infection and the absence of the immune complex identifies the subject as not having a Filovirus infection.

TABLE 1

| Filovirus protein and residues | Exemplary Sequence | SEQ ID NO |
|---|---|---|
| NP 1-21 | MDSRPQKVWMTPSLTESDMDY | 1 |
| NP 1-41 | MDSRPQKVWMTPSLTESDMDYHKILTAGLSVQQGIVRQRVI | 2 |
| NP 453-514 | TIPDVVVDPDDGGYGEYQSYSENGMSAPDDLVLFDLDEDDEDTKPVPNRSTKGGQQKNSQKG | 3 |
| VP35 742-815 | MTTRTKGRGHTVATTQNDRMPGPELSGWISEQLMTGRIPVNDIFCDIENNPGLCYASQMQQTKPNPKMRNSQTQ | 4 |
| VP35 895-934 | ATAAATEAYWAEHGQPPPGPSLYEESAIRGKIESRDETVP | 5 |
| VP35 930-965 | DETVPQSVREAFNNLDSTTSLTEENFGKPDISAKDL | 6 |
| VP40 1084-1116 | MRRVILPTAPPEYMEAIYPARSNSTIARGGNSN | 7 |
| VP40 1084-1133 | MRRVILPTAPPEYMEAIYPARSNSTIARGGNSNTGFLTPESVNGDTPSNP | 8 |
| VP40 1313-1387 | DLTSPEKIQAIMTSLQDFKIVPIDPTKNIMGIEVPETLVHKLTGKKVTSKNGQPIIPVLLPKYIGLDPVAPGDLT | 9 |
| VP40 1331-1377 | KIVPIDPTKNIMGIEVPETLVHKLTGKKVTSKNGQPIIPVLLPKYIG | 10 |
| VP40 1307-1353 | KKGNSADLTSPEKIQAIMTSLQDFKIVPIDPTKNIMGIEVPETLVHK | 11 |
| VP30 2088-2114 | MEASYERGRPRAARQHSRDGHDHHVRA | 12 |
| VP30 2088-2142 | MEASYERGRPRAARQHSRDGHDHHVRASSSRENYRGEYRQSRSASQVRVPTVFH | 13 |
| VP24 2560-2612 | TQNHTIIITRTNMGFLVELQEPDKSAMNRKKPGPAKFSLLHESTLKAFTQGSS | 14 |

In some embodiments, the method comprises contacting a biological sample containing antibodies from the subject with one or more peptides selected from those shown in Table 1, and detecting the presence or absence of an immune complex of antibodies from the biological sample with the one or more peptides. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1-21 of a Filovirus NP protein, such as residues 1-21 of an ZEBOV NP protein, for example as set forth as SEQ ID NO: 1. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1-41 of a Filovirus NP protein, such as residues 1-41 of an ZEBOV NP protein, for example as set forth as SEQ ID NO: 2. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 453-514 of a Filovirus NP protein, such as residues 453-514 of an ZEBOV NP protein, for example as set forth as SEQ ID NO: 3. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 742-815 of a Filovirus VP35 protein, such as residues 742-815 of an ZEBOV VP35 protein, for example as set forth as SEQ ID NO: 4. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 895-934 of a Filovirus VP35 protein, such as residues 895-934 of an ZEBOV VP35 protein, for example as set forth as SEQ ID NO: 5. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 930-965 of a Filovirus VP35 protein, such as residues 930-965 of an ZEBOV VP35 protein, for example as set forth as SEQ ID NO: 6. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1084-1116 of a Filovirus VP40 protein, such as residues 1084-1116 of an ZEBOV VP40 protein, for example as set forth as SEQ ID NO: 7. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1084-1133 of a Filovirus VP40 protein, such as residues 1084-1133 of an ZEBOV VP40 protein, for example as set forth as SEQ ID NO: 8. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1313-1387 of a Filovirus VP40 protein, such as residues 1313-1387 of an ZEBOV VP40 protein, for example as set forth as SEQ ID NO: 9. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1331-1377 of a Filovirus VP40 protein, such as residues 1331-1377 of an ZEBOV VP40 protein, for example as set forth as SEQ ID NO: 10. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 1307-1353 of a Filovirus VP40 protein, such as residues 1307-1353 of an ZEBOV VP40 protein, for example as set forth as SEQ ID NO: 11. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 2088-2114 of a Filovirus VP30 protein, such as residues 2088-2114 of an ZEBOV VP30 protein, for example as set forth as SEQ ID NO: 12. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 2088-2142 of a Filovirus VP30 protein, such as residues 2088-2142 of an ZEBOV VP30 protein, for example as set forth as SEQ ID NO: 13. The presence of the immune complex identifies the subject as having Filovirus infection and the absence of the immune complex identifies the subject as not having Filovirus infection.

In some embodiments, the method comprises contacting a biological sample containing antibodies from the subject with a peptide comprising, consisting essentially of, or consisting of residues 2560-2612 of a Filovirus VP24 protein, such as residues 2560-2612 of an ZEBOV VP24 protein, for example as set forth as SEQ ID NO: 14. The presence of the immune complex identifies the subject as having Filovirus infection and the absence of the immune complex identifies the subject as not having Filovirus infection.

In some embodiments, a combination of the peptides provided in Table 1 is used to identify a subject with a Filovirus infection. For example, a combination of at least 2 (such as at least 3, 4, 5, 6, 7, 8, 9, 10, 11, 12, 13, or all 14) of the peptides is used to identify a subject with a Filovirus infection. In some examples, the at least two peptides includes the peptides of SEQ ID NO: 6 and SEQ ID NO: 9. In some examples, the at least three peptides includes the peptides of SEQ ID NO: 6, SEQ ID NO: 9 and SEQ ID NO: 12. In some examples, the at least four peptides includes the peptides of SEQ ID NO: 6, SEQ ID NO: 8, SEQ ID NO: 9 and SEQ ID NO: 14. In some examples, the at least five peptides includes the peptides of SEQ ID NO: 6, SEQ ID NO: 8, SEQ ID NO: 9, SEQ ID NO: 12 and SEQ ID NO: 14.

In some examples, the method further includes treating the subject identifying as having a Filovirus infection. For example, the subject can be treated by administering a therapeutically effective amount of an anti-viral agent. In specific examples, the antiviral agent is a monoclonal antibody that specifically binds to a glycoprotein extracellular domain of the Filovirus.

Also provided herein is a method of identifying a biological sample containing Filovirus-specific antibodies. In some embodiments, the method includes contacting the biological sample with one or more peptides listed in Table 1 (for example, one or more peptides comprising amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14), and detecting the presence or absence of an immune complex of Filovirus-specific antibodies from the biological sample with the one or more peptides. The presence of the immune complex identifies the biological sample as containing Filovirus-specific antibodies and the absence of the immune complex identifies the biological sample as not containing Filovirus-specific antibodies. In some examples, the one or more peptides consist of or consist essentially of the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14. As noted above, a combination of the peptides provided in Table 1 can be used to identify a biological sample containing Filovirus-specific antibodies. For example, a combination of at least 2 (such as at least 3, 4, 5, 6, 7, 8, 9, 10, 11, 12, 13, or all 14) of the peptides is used to identify a biological sample containing Filovirus-specific antibodies. In some examples, the at least two peptides includes the peptides of SEQ ID NO: 6 and SEQ ID NO: 9. In some examples, the at least three peptides includes the peptides of SEQ ID NO: 6, SEQ ID NO: 9 and SEQ ID NO: 12. In some examples, the at least four peptides includes the peptides of SEQ ID NO: 6, SEQ ID NO: 8, SEQ ID NO: 9 and SEQ ID NO: 14. In some examples, the at least five peptides includes the peptides of SEQ ID NO: 6, SEQ ID NO: 8, SEQ ID NO: 9, SEQ ID NO: 12 and SEQ ID NO: 14.

The sequences presented in Table 1 are sequences of ZEBOV proteins. Due to the sequence homology across Filoviruses proteins, the sequences provided in Table 1 can readily be identified in other filovirus proteins, for example, from any of Bundibugyo ebolavirus, Sudan ebolavirus, Tai Forest ebolavirus, or Marburg marburgvirus, or other Filovirus strains.

In the context of the disclosed methods, the peptide can be any suitable length, for example, no more than 150 amino acids in length, such as no more than 100 or no more than 75 amino acids in length, or from 75-100, 75-150, or 100-150 amino acids in length.

In the disclosed methods, the biological sample or a processed form thereof is contacted with the one or more peptides and the presence or absence of an immune complex of antibodies from the biological sample with the one or more peptides is detected. Any suitable technique may be used to detect the presence or absence of the immune complex. In some embodiments, the presence or absence of the immune complex is determined using biosensors, immunodetection, immunohistochemistry, immunoprecipitation, flow cytometry, immunofluorescence microscopy, ELISA, immunoblotting (for example, Western blot), magnetic resonance imaging, CT scan, X-ray and affinity chromatography.

In some embodiments, an immunoassay (such as ELISA, indirect ELISA, Western blot, or RIA assay) is used to identify the presence or absence of antibodies in the biological sample that specifically bind to one or more of the peptides listed in Table 1. Immunohistochemical techniques can also be utilized. General guidance regarding such techniques can be found in Suvarna, Layton, and Bancroft (Eds.) "*Theory and Practice of Histological Techniques,*" 8$^{th}$ Ed., Elsevier, 2019) and Ausubel et al. (Eds.) (*Current Protocols in Molecular Biology*, New York: John Wiley and Sons, 2017, and Greenfield (Ed.), *Antibodies: A Laboratory Manual*, 2$^{nd}$ ed. New York: Cold Spring Harbor Laboratory Press, 2014; these references disclose a number of immunoassay formats and conditions that can be used to determine specific immunoreactivity. Generally, the immunoassay involves incubating the one or more peptides listed in Table 1 with the biological sample containing antibodies form the subject under conditions sufficient to allow for specific binding of antibodies in the sample to the one or more peptides, if antibodies specific to the epitopes in the peptides are present in the sample. Although the details of the immunoassays may vary with the particular format employed, the method of detecting the protein in a sample generally includes the steps of contacting the sample with an one or more peptides, which specifically bind to the antibodies in the sample under immunologically reactive conditions to form an immune complex between the antibody and the one or more peptides (assuming that such antibodies are present in the sample), and detecting the presence of and/or quantity of the immune complex (bound antibody), either directly or indirectly.

The peptides can be labeled. Any suitable label may be used. For example, various enzymes, prosthetic groups, fluorescent materials, luminescent materials, magnetic agents, and radioactive materials can be used. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin, etc. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

Additional examples are disclosed above. In particular examples, the peptides are biotinylated.

The concentration of antibodies in the biological sample specific for the one or more peptides that is detected can be compared to a control, such as the concentration of the antibodies specific for the one or more peptides in a subject known to have or not to have a Filovirus infection, or known to have or not to have a chronic Filovirus infection. In other embodiments, the control is a standard value, such as a value that represents an average concentration of the antibodies specific for the one or more peptides that is expected in a subject known to have or not to have a Filovirus infection, or known to have or not to have a chronic Filovirus infection. In some embodiments, the presence or absence of the immune complex is determined based on a level or amount of antibodies in the biological sample that specifically bind to the one or more peptides listed in Table 1. The amounts of antibody in the sample from the subject can be compared to levels of the antibody found in samples form control subjects or to another control (such as a standard value or reference value). A significant increase or decrease in the amount can be evaluated to determine the presence or absence of the immune complex.

In some non-limiting examples, an indirect ELISA can be used to detect the presence or absence or determine the amount of an antibodies in the biological sample that specifically bind to the one or more peptides listed in Table 1. In this method, a solid support is first coated with the one or more peptides. The test sample containing antibodies (such as, but not limited to, a blood, plasma, serum, or urine sample), is then added and the antibodies are allowed to react with the peptide. Any unbound antibody is washed away. A labeled secondary antibody (for example, enzyme-labeled) is then allowed to react with the bound antibody. Any excess unbound labeled secondary antibody is washed away after the reaction. The label is detected to identify and/or quantify the amount of primary antibody bound to the one or more peptides on the solid support. In some embodiments, the secondary antibody is enzyme-labeled and the substrate for the enzyme used in the assay is added and the reaction between the substrate and the enzyme produces a color change. The amount of visual color change is a direct measurement of specific enzyme-conjugated bound antibody, and consequently the quantity of the antibody that specifically binds to the one or more peptides present in the sample tested.

Monoclonal or polyclonal antibodies raised against any of these peptides can be used to detect the presence of Filovirus antigen in the biological sample to determine the Filovirus infection.

In some examples of the disclosed detection methods, the solid support (such as a multi-well plate suitable for an ELISA) is coated in streptavidin and the one or more peptides are biotinylated.

III. Methods of Treatment

In some embodiments, the method further comprises treating the subject identified as having the Filovirus infection, for example, by administering an effective amount of an anti-ebolavirus agent (such as a monoclonal antibody that specifically binds to Filovirus protein and inhibits Filovirus infection) to inhibit the Filovirus infection in the subject.

In some embodiments, the subject is identified as having a Filovirus infection and is treated by administering an effective amount of an anti-viral agent, such as a monoclonal antibody that specifically binds to Ebolavirus GP protein and inhibits Ebolavirus infection, such as mAb114 (also known as EVB114 as described in U.S. Pat. No. 10,160,795, incorporated by reference herein), mAb100, REGN-EB3, or ZMapp, or a small molecule such as remdesivir.

The Filovirus infection does not need to be completely inhibited for the method to be effective. For example, the method can inhibit the Filovirus infection (for example, as measured by infection of cells, or by number or percentage of subjects infected by the filovirus, or by an increase in the survival time of infected subjects, or by reduction in symptoms associated with filovirus infection) by a desired amount, for example by at least 10%, at least 20%, at least 50%, at least 60%, at least 70%, at least 80%, at least 90%, at least 95%, at least 98%, or even at least 100% (elimination of detectable Filovirus infection) as compared to a suitable control, such as Filovirus infection in the absence of the treatment.

In some embodiments, administration of an effective amount of an anti-viral agent (such as an antibody that specifically binds to Filovirus GP protein and inhibits Filovirus infection) inhibits the Filovirus disease progression in a subject, which can encompass any statistically significant reduction in Filovirus activity or symptoms of infection in the subject.

The effective amount of an anti-viral agent that is administered to a subject to inhibit Filovirus infection will vary depending upon a number of factors associated with that subject, for example the overall health and/or weight of the subject. An effective amount can be determined by varying the dosage and measuring the resulting response, such as, for example, a reduction in pathogen titer. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Antibodies and antigen binding fragments thereof are typically administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

The antibody can be administered to subjects in various ways, including local and systemic administration, such as, e.g., by injection subcutaneously, intravenously, intra-arterially, intraperitoneally, intramuscularly, intradermally, or intrathecally. In an embodiment, the antibody is administered by a single subcutaneous, intravenous, intra-arterial, intraperitoneal, intramuscular, intradermal or intrathecal injection once a day. The antibody can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody over a pre-determined period. The osmotic pump or mini-pump can be implanted subcutaneously, or near a target site.

IV. Filovirus Peptides

Isolated peptides containing fragments of Filovirus proteins are disclosed herein that can be used to detect or vaccinate/treat a Filovirus infection in a subject. As discussed in the Examples, the isolated peptides contain antigenic sites of the Filovirus proteins that are targeted by antibodies elicited in a subject with a Filovirus infection.

In some embodiments, the isolated peptide comprises residues 1-21 of a Filovirus NP protein, such as residues 1-21 of an ZEBOV NP protein, for example as set forth as SEQ ID NO: 1, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1-21 of a Filovirus NP protein, such as residues 1-21 of an ZEBOV NP protein, for example as set forth as SEQ ID NO: 1.

In some embodiments, the isolated peptide comprises residues 1-41 of a Filovirus NP protein, such as residues 1-41 of an ZEBOV NP protein, for example as set forth as SEQ ID NO: 2, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1-41 of a Filovirus NP protein, such as residues 1-41 of an ZEBOV NP protein, for example as set forth as SEQ ID NO: 2.

In some embodiments, the isolated peptide comprises residues 453-514 of a Filovirus NP protein, such as residues 453-514 of an ZEBOV NP protein, for example as set forth as SEQ ID NO: 3, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 453-514 of a Filovirus NP protein, such as residues 453-514 of an ZEBOV NP protein, for example as set forth as SEQ ID NO: 3.

In some embodiments, the isolated peptide comprises residues 742-815 of a Filovirus VP35 protein, such as residues 742-815 of an ZEBOV VP35 protein, for example as set forth as SEQ ID NO: 4, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 742-815 of a Filovirus VP35 protein, such as residues 742-815 of an ZEBOV VP35 protein, for example as set forth as SEQ ID NO: 4.

In some embodiments, the isolated peptide comprises residues 895-934 of a Filovirus VP35 protein, such as residues 895-934 of an ZEBOV VP35 protein, for example as set forth as SEQ ID NO: 5, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 895-934 of a Filovirus VP35 protein, such as residues 895-934 of an ZEBOV VP35 protein, for example as set forth as SEQ ID NO: 5.

In some embodiments, the isolated peptide comprises residues 930-965 of a Filovirus VP35 protein, such as residues 930-965 of an ZEBOV VP35 protein, for example as set forth as SEQ ID NO: 6, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 930-965 of a Filovirus VP35 protein, such as residues 930-965 of an ZEBOV VP35 protein, for example as set forth as SEQ ID NO: 6.

In some embodiments, the isolated peptide comprises residues 1084-1116 of a Filovirus VP40 protein, such as residues 1084-1116 of an ZEBOV VP40 protein, for example as set forth as SEQ ID NO: 7, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1084-1116 of a Filovirus VP40 protein, such as residues 1084-1116 of an ZEBOV VP40 protein, for example as set forth as SEQ ID NO: 7.

In some embodiments, the isolated peptide comprises residues 1084-1133 of a Filovirus VP40 protein, such as residues 1084-1133 of an ZEBOV VP40 protein, for example as set forth as SEQ ID NO: 8, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1084-1133 of a Filovirus VP40 protein, such as residues 1084-1133 of an ZEBOV VP40 protein, for example as set forth as SEQ ID NO: 8.

In some embodiments, the isolated peptide comprises residues 1313-1387 of a Filovirus VP40 protein, such as residues 1313-1387 of an ZEBOV VP40 protein, for example as set forth as SEQ ID NO: 9, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1313-1387 of a Filovirus VP40 protein, such as residues 1313-1387 of an ZEBOV VP40 protein, for example as set forth as SEQ ID NO: 9.

In some embodiments, the isolated peptide comprises residues 1331-1377 of a Filovirus VP40 protein, such as residues 1331-1377 of an ZEBOV VP40 protein, for example as set forth as SEQ ID NO: 10, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1331-1377 of a Filovirus VP40 protein, such as residues 1331-1377 of an ZEBOV VP40 protein, for example as set forth as SEQ ID NO: 10.

In some embodiments, the isolated peptide comprises residues 1307-1353 of a Filovirus VP40 protein, such as residues 1307-1353 of an ZEBOV VP40 protein, for example as set forth as SEQ ID NO: 11, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 1307-1353 of a Filovirus VP40 protein, such as residues 1307-1353 of an ZEBOV VP40 protein, for example as set forth as SEQ ID NO: 11.

In some embodiments, the isolated peptide comprises residues 2088-2114 of a Filovirus VP30 protein, such as residues 2088-2114 of an ZEBOV VP30 protein, for example as set forth as SEQ ID NO: 12, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 2088-2114 of a Filovirus VP30 protein, such as residues 2088-2114 of an ZEBOV VP30 protein, for example as set forth as SEQ ID NO: 12.

In some embodiments, the isolated peptide comprises residues 2088-2142 of a Filovirus VP30 protein, such as residues 2088-2142 of an ZEBOV VP30 protein, for example as set forth as SEQ ID NO: 13, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 2088-2142 of a Filovirus VP30 protein, such as residues 2088-2142 of an ZEBOV VP30 protein, for example as set forth as SEQ ID NO: 13.

In some embodiments, the isolated peptide comprises residues 2560-2612 of a Filovirus VP24 protein, such as residues 2560-2612 of an ZEBOV VP24 protein, for example as set forth as SEQ ID NO: 14, and is no more than 150 amino acids in length, such as no more than 100 or no more than 75 amino acids in length, or from 75-100, 75-150, or 100-150 amino acids in length. In some embodiments, the isolated peptide consists essentially of or consists of residues 2560-2612 of a Filovirus VP24 protein, such as residues 2560-2612 of an ZEBOV VP24 protein, for example as set forth as SEQ ID NO: 14.

The sequences presented in Table 1 are sequences of ZEBOV proteins. Due to the sequence homology across Filoviruses proteins, the sequences provided in Table 1 can readily be identified in other filovirus proteins, for example, from any of Bundibugyo ebolavirus, Sudan ebolavirus, Tai Forest ebolavirus, or Marburg marburgvirus, or other Filovirus strains.

The peptides disclosed herein can be prepared using any suitable technique, for example, solid-phase synthesis and molecular biology techniques, such as expression from recombinant DNA. In some embodiments, the peptides incorporate one or more modified amino acid residues (e.g., D-amino acids, homologs of naturally occurring amino acids, amino acids with modified side chains, etc.). Following synthesis, exemplary techniques for peptide purification include reverse phase chromatography, high performance liquid chromatography, ion exchange chromatography, size exclusion chromatography, affinity chromatography, and gel electrophoresis. The actual conditions used to purify a particular peptide, or a modified form thereof, will depend, in part, on synthesis strategy and on factors such as net charge, hydrophobicity, hydrophilicity, and the like.

Any of the isolated peptides disclosed herein can be linked to a solid support, for example, to facilitate detection of antibodies in a biological sample from the subject that specifically bind to the peptide.

Any suitable sold support can be used. The solid support can be any material which is insoluble, or can be made insoluble by a subsequent reaction, and to which the peptide can be linked for use in a detection assay to identify antibodies in a biological sample that specifically bind to the peptide. Non-limiting examples include nitrocellulose, the walls of wells of a reaction tray, multi-well plates, test tubes, polystyrene (e.g., polystyrene beads), polyvinyl (e.g., polyvinyl beads), magnetic beads, membranes, hydrogel, molecules such as tags, fluorescence, luminescence, and microparticles (such as latex particles).

The solid support can have any suitable shape for use in the desired detection assay, such as films, sheets, strips, or plates, or it may be coated onto or bonded or laminated to appropriate inert carriers, such as paper, glass, plastic films, or fabrics. In some embodiments, the solid support is in the shape of a strip, for example, for use as a lateral flow strip in a lateral flow device.

Additionally, any of the isolated peptides disclosed herein can be conjugated to a carrier molecule, for example, to enhance an immune response in a subject to the peptide.

The peptide can be directly conjugated to the solid support or carrier, or indirectly via a linker.

Suitable linkers include, but are not limited to, straight or branched-chain carbon linkers, heterocyclic carbon linkers or peptide linkers. Typically, the peptide, linker, carrier, and/or solid support contains the necessary reactive groups for linkage. Representative combinations of such groups are amino with carboxyl to form amide linkages or carboxy with hydroxyl to form ester linkages or amino with alkyl halides to form alkylamino linkages or thiols with thiols to form disulfides or thiols with maleimides or alkylhalides to form thioethers. Hydroxyl, carboxyl, amino and other functionalities, where not present may be introduced by known methods. Likewise, a wide variety of linking groups may be employed. In some cases, the linking group can be designed to be either hydrophilic or hydrophobic in order to enhance the desired binding characteristics of the peptide and the support. The covalent linkages should be stable relative to the solution conditions under which the peptide and support are subjected.

In some embodiments, the linkers may be joined to the constituent amino acids of the peptide through their side chains (such as through a disulfide linkage to cysteine) or to the alpha carbon, amino, and/or carboxyl groups of the terminal amino acids. In some embodiments, the linker, the peptide, and the carrier can be encoded as a single peptide such that the peptide and the carrier are joined by peptide bonds.

The procedure for attaching a peptide to the solid support or the carrier varies according to the chemical structure of the molecules. Peptides typically contain a variety of functional groups; for example, carboxylic acid (COOH), free amine (—$NH_2$) or sulfhydryl (—SH) groups, which are available for reaction with a suitable functional group on a linker. Alternatively, the peptide is derivatized to expose or attach additional reactive functional groups. The derivatization may involve attachment of any of a number of linker molecules.

In some embodiments, a sulfosuccinimidyl (4-iodoacetyl) aminobenzoate (Sulfo-SIAB) linker is used to link the peptide to the solid support or the carrier. In some embodiments an m-maleimidobenzoyl-N-hydroxysuccinimide ester (MBS) linker is used to attach the peptide to the solid support or the carrier.

In some examples, the peptide and the carrier are linked by a linker between a lysine amino acid residue present on the carrier protein and a cysteine amino acid residue fused (by a peptide bond) to the C-terminal residue of the peptide.

Any specific combination of peptide and carrier may be selected from the specific peptides and carriers that are listed herein.

It can be advantageous to produce conjugates in which more than one peptide as described herein is conjugated to a single carrier protein. In several embodiments, the conjugation of multiple peptides to a single carrier protein is possible because the carrier protein has multiple lysine or cysteine side-chains that can serve as sites of attachment. The amount of peptide reacted with the amount of carrier may vary depending upon the specific peptide and the carrier. In some embodiments, from 1 to 30, such as about 1, about 5, about 10, about 15, about 20, or about 30 peptides, or more, can be linked to each carrier protein molecule. In some embodiments (such as when KLH is used as a carrier, from 1 to 1000, such as about 10, about 20, about 30, about 40, about 50, about 100, about 200, about 300, about 400, about 500, about 700, or about 1000 peptides can be linked to each carrier protein molecule. "About" in this context refers to plus or minus 5% when measuring an average number of peptide molecules per carrier molecule in the conjugate.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, recombinantly produced, semi-synthetic or synthetic materials containing one or more amino groups, such as those present in a lysine amino acid residue present in the carrier, to which a reactant moiety can be attached. A carrier can be useful even if the antibody that it elicits is not of benefit by itself.

Specific, non-limiting examples of suitable polypeptide carriers include, but are not limited to, natural, semi-synthetic or synthetic polypeptides or proteins from bacteria or viruses. In one embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GENBANK® Accession No. NC 007322); *B. anthracis* LF (for example, as encoded by the complement of bases 149357 to 151786 of GENBANK® Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065), such as tetanus toxin heavy chain C fragment; *P. aeruginosa* exotoxin/toxoid (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094) *C. difficile* toxin B or A, or analogs or mimetics of and combinations of two or more thereof. Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin (KLH), horseshoe crab hemocyanin, Concholepas Hemocyanin (CCH), Ovalbumin (OVA), edestin, mammalian serum albumins (such as bovine serum albumin), and mammalian immunoglobulins. In some examples, the carrier is bovine serum albumin.

In some embodiments, the carrier is selected from one of: KLH, tetanus toxoid, tetanus toxin heavy chain C fragment, diphtheria toxoid, diphtheria toxin variant CRM197, or H influenza protein D (HiD). CRM197 is a genetically detoxified form of diphtheria toxin; a single mutation at position 52, substituting glutamic acid for glycine, causes the ADP-ribosyltransferase activity of the native diphtheria toxin to be lost. For description of protein carriers for vaccines, see Pichichero, Protein carriers of conjugate vaccines: characteristics, development, and clinical trials, Hum Vaccin Immunother., 9: 2505-2523, 2013, which is incorporated by reference herein in its entirety).

Following conjugation of the peptide to the carrier protein, the conjugate can be purified by appropriate techniques. One goal of the purification step is to separate the unconjugated peptide or carrier from the conjugate.

In several embodiments, the disclosed immunogenic conjugates can be formulated into an immunogenic composition (such as vaccines), for example by the addition of a pharmaceutically acceptable carrier and/or adjuvant.

V. Immunogenic Compositions

Immunogenic compositions comprising a disclosed peptide (for example, linked to a carrier) or a nucleic acid molecule or vector encoding the peptide and a pharmaceutically acceptable carrier are also provided. Such compositions can be administered to subjects by a variety of administration modes, for example, intramuscular, subcutaneous, intravenous, intra-arterial, intra-articular, intraperitoneal, or parenteral routes. Actual methods for preparing administrable compositions are described in more detail in such publications as *Remingtons Pharmaceutical Sciences,* 19$^{th}$ Ed., Mack Publishing Company, Easton, Pa., 1995.

The peptide (for example, linked to a carrier) or a nucleic acid molecule or vector encoding the peptide can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, Mass.) may also be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In some embodiments, the immunogenic composition can be provided as a sterile composition. The immunogenic composition typically contains an effective amount of a disclosed peptide (for example, linked to a carrier) or a nucleic acid molecule or vector encoding the peptide, and can be prepared by conventional techniques. Typically, the amount of a disclosed peptide (for example, linked to a carrier) or a nucleic acid molecule or vector encoding the peptide in each dose of the immunogenic composition is selected as an amount which elicits an immune response without significant, adverse side effects. In some embodiments, the immunogenic composition can be provided in unit dosage form for use to elicit an immune response in a subject, for example, to prevent ebolavirus infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

VI. Methods of Inducing an Immune Response

An immunogenic composition comprising a disclosed filovirus peptide, a nucleic acid molecule (such as an RNA molecule) encoding a disclosed filovirus peptide, vector including the nucleic acid molecule, or immunogenic composition, can be administered to a subject to induce an immune response to filovirus in the subject. In a particular example, the subject is a human. The immune response can be a protective immune response, for example a response that inhibits subsequent infection with a filovirus (such as a Zaire ebolavirus). Elicitation of the immune response can also be used to treat or inhibit infection and illnesses associated with a filovirus (such as a Zaire ebolavirus).

A subject can be selected for immunization that has, or is at risk for developing infection or illness associated with a filovirus (such as a Zaire ebolavirus), for example because of exposure or the possibility of exposure to a filovirus (such as a Zaire ebolavirus).

Typical subjects intended for administration of the immunogenic composition include humans, as well as non-human primates and other animals. To identify relevant subjects, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize a filovirus (such as a Zaire ebolavirus) infection. These and other routine methods allow the clinician to select patients in need of therapy. In accordance with these methods and principles, the immunogenic composition can be administered according to the teachings herein, or other conventional methods, as an independent prophylaxis or treatment program, or as a follow-up, adjunct or coordinate treatment regimen to other treatments.

The administration of the immunogenic composition can be for prophylactic or therapeutic purpose. When provided prophylactically, the immunogenic composition can be provided in advance of any symptom, for example, in advance of infection. The prophylactic administration serves to prevent or ameliorate any subsequent infection. In some embodiments, the methods can involve selecting a subject at risk for contracting filovirus infection (e.g., Zaire ebolavirus infection), and administering an effective amount of the immunogenic composition to the subject. The immunogenic composition can be provided prior to the anticipated exposure to filovirus infection (e.g., Zaire ebolavirus infection) so as to attenuate the anticipated severity, duration or extent of an infection and/or associated disease symptoms, after exposure or suspected exposure to the virus, or after the actual initiation of an infection.

The immunogenic composition is provided to the subject in an amount effective to induce or to enhance an immune response against filovirus (e.g., Zaire ebolavirus) in the subject, preferably a human. The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to filovirus (e.g., Zaire ebolavirus). Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example, a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of filovirus infection (e.g., Zaire ebolavirus infection) or improvement in disease state (e.g., reduction in viral load). If such monitoring indicates that vaccination is sub-optimal, the subject can be boosted with an additional dose of immunogenic composition, and the vaccination parameters can be modified in a manner expected to potentiate the immune response.

In some embodiments, the prime-boost method can include DNA-prime and protein-boost vaccination protocol to a subject. The method can include two or more administrations of the nucleic acid molecule or the protein.

For peptide therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

The amount utilized in an immunogenic composition is selected based on the subject population (e.g., infant or elderly). An optimal amount for a particular composition can be ascertained by standard studies involving observation of antibody titers and other responses in subjects. It is understood that an effective amount of a disclosed immunogenic composition can include an amount that is ineffective at eliciting an immune response by administration of a single dose, but that is effective upon administration of multiple dosages, for example in a prime-boost administration protocol.

Upon administration of the immunogenic composition, the immune system of the subject typically responds to the immunogenic composition by producing antibodies specific for viral protein. Such a response signifies that an immunologically effective dose was delivered to the subject.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, filovirus (e.g., Zaire ebolavirus).

Filovirus infection (e.g., Zaire ebolavirus infection) does not need to be completely eliminated or reduced or prevented for the methods to be effective. For example, elicitation of the immune response can reduce or inhibit infection with the filovirus (e.g., Zaire ebolavirus) by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the filovirus (e.g., Zaire ebolavirus) in the absence of the immunization.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In some embodiments, a plasmid DNA vaccine is used to express a disclosed filovirus peptide (e.g., Zaire ebolavirus peptide) in a subject. For example, a nucleic acid molecule encoding a disclosed filovirus peptide (e.g., Zaire ebolavirus peptide) can be administered to a subject to induce an immune response to filovirus (e.g., Zaire ebolavirus).

In another approach, a disclosed filovirus peptide (e.g., Zaire ebolavirus peptide) can be expressed by attenuated viral hosts or vectors or bacterial vectors. Recombinant vaccinia virus, adeno-associated virus (AAV), herpes virus, retrovirus, cytomegalovirus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991). These peptides can also be used in combination or with vaccines against other pathogens.

In one embodiment, a nucleic acid encoding a disclosed filovirus peptide (e.g., Zaire ebolavirus peptide) is introduced directly into cells to induce the immune response. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed filovirus peptide (e.g., Zaire ebolavirus peptide) directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed filovirus peptide (e.g., Zaire ebolavirus peptide) include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

In some embodiments, administration of an effective amount of one or more of the disclosed immunogens to a subject induces a neutralizing or protective immune response in the subject. To assess neutralization activity, following immunization of a subject, serum can be collected from the subject at appropriate time points, frozen, and stored for neutralization testing. Methods to assay for binding or neutralization activity are known to the person of ordinary skill in the art and are further described herein, and include, but are not limited to, ELISA, plaque reduction neutralization (PRNT) assays, microneutralization assays, flow cytometry based assays, single-cycle infection assays. In some embodiments, the serum neutralization activity can be assayed using a panel of filovirus (e.g., Zaire ebolavirus) pseudoviruses.

EXAMPLES

The following examples are provided to illustrate particular features of certain embodiments, but the scope of the claims should not be limited to those features exemplified.

Example 1

Human Antibody Repertoire Against Complete Viral Proteome Following Acute Ebola Virus Infection Evolution of antibody repertoire against entire Zaire ebolavirus proteome was characterized in an acutely infected patient receiving supportive care alone to elucidate virus-host interaction over time. Differential kinetics was observed for IgM/IgG/IgA epitope diversity, antibody binding, and affinity maturation to ZEBOV proteins. During acute illness, antibodies predominated to VP40 and GP, followed by VP30, VP35, VP24 and NP. At day 13 of clinical illness, a marked increase in antibody titers to most ZEBOV proteins and affinity maturation to GP was associated with rapid decline in viral replication and illness severity. At one-year, despite undetectable virus, a diverse IgM repertoire against VP40 and GP epitopes was observed suggesting occult viral persistence. Immunodominant sites in C-terminus of GP1 and conserved GP2-HR2 induced ZEBOV-neutralizing antibodies and protected vaccinated mice against lethal ZEBOV challenge. This example illustrates markers of viral persistence and infection provide a promising approach for development and evaluation of vaccines and therapeutics.

Introduction

Zaire ebolavirus (ZEBOV) causes severe and often fatal disease in humans and remains a global public health challenge. The ongoing ZEBOV epidemic in the Democratic Republic of the Congo (DRC) has resulted in 3206 cases and 2143 deaths (case fatality ratio=67%) as of Oct. 7, 2019 (who.int/emergencies/diseases/ebola/drc-2019), and the 2013-16 ZEBOV epidemic in West Africa resulted in an estimated 28,652 cases and 11,325 deaths. Given that ZEBOV may persist in semen of male survivors risking sexual transmission (Deen et al. N Engl J Med. 377(15), 1428-1437, 2017), and that natural spillover events continue to occur, the likelihood of recurrent severe outbreaks remains high.

Development of effective vaccines for prevention and medical countermeasures for treatment of ZEBOV infection remains a high global priority. Multiple vaccine candidates based on ZEBOV-GP are being evaluated in humans, although duration of protective immunity is undetermined. However, little is known about which sites within GP are responsible for vaccine induced antibody mediated protection against ZEBOV. Most studies on ZEBOV infection/vaccination in humans used MAb as surrogate readouts, and no vaccination studies have been performed to evaluate the contribution of each individual antigenic site within ZEBOV-GP as an immunogen/vaccine to generate ZEBOV neutralizing antibodies or protection against Ebola virus disease (EVD). It is postulated that immune responses generated during ZEBOV infection likely provide life-long protection among survivors, and so deeply characterizing immune responses in survivors, and correlating those responses to viral clearance and recovery might assist in rational vaccine and therapeutic design.

Prior studies evaluated immune responses among EVD survivors, although all patients had received antibody treatment (ZMapp or convalescent plasma), which may confound study conclusions, and analyses primarily focused on anti-GP antibodies performed on samples collected after disease resolution, using MAbs as surrogate readouts. One study showed that individual MAbs developed following rVSV-ZEBOV vaccination, 30-76% reacted with Sudan virus (SUDV). In contrast, the polyclonal sera elicited by rVSV-ZEBOV vaccination appears to be specific to just ZEBOV, with little detectable reactivity to SUDV or other ebolaviruses at the polyclonal level. These studies did not determine epitope specificity against the complete ZEBOV proteome, nor did they closely characterize antibody kinetics during disease progression and resolution. Enzyme linked immunosorbent assays (ELISA) and ZEBOV-neutralization tests targeting ZEBOV surface glycoprotein (GP) have primarily been used to characterize antibody responses in humans following ZEBOV infection, but provide limited insight into the diversity and quality of polyclonal antibody responses across the complete ZEBOV proteome and its evolution over time (Cohen and Enserink. Science. 349 (6254), 1272-1273, 2015; Krause. Lancet. 386(9996), 831-833, 2015; Matassov et al. J Infect Dis. 212 Suppl 2, S443-451, 2015; Wong et al., Sci Transl Med. 4(158), 158ra146, 2012). Moreover, the contribution of different antigenic sites in ZEBOV-GP as an immunogen or vaccine in neutralization/protection against EVD is unknown.

Previously, genome-fragment phage display library (GFPDL) spanning the entire genome of highly pathogenic avian influenza virus, respiratory syncytial virus and Zika virus were used to map the antibody repertoires of convalescent sera from infected individuals and in individuals after pandemic influenza vaccinations. These studies have revealed several diagnostic and protective targets (Fuentes et al., PLoS Pathog. 12(4), e1005554, 2016; Khurana et al. Sci Transl Med. 2(15), 15ra15, 2010; Khurana et al. J Virol. 85(23), 12455-12463, 2011; Khurana et al. PLoS Med. 6(4), e1000049, 2009; Khurana et al. Sci Transl Med. 3(85), 85ra48, 2011; Ravichandran et al. Nat Commun. 10(1), 1943, 2019). This example provides a comprehensive longitudinal analysis of the humoral immune response across the complete ZEBOV proteome in a critically ill patient with EVD who survived with supportive care alone (i.e., without the use of experimental therapies) correlated to antibody responses with viral clearance and disease resolution. After selecting immunodominant antigens in the single patient it was sought to determine if synthetic peptides, reflective of these antigenic sites within surface GP, would induce ZEBOV-neutralizing responses in a rabbit model and provide protection from lethal EOBV infection in a mouse model. The strategy was to use complete ZEBOV genome fragment-phage display libraries (GFPDL) to elucidate the epitope repertoire recognized by IgM, IgG & IgA polyclonal antibodies in sera and surface plasmon resonance (SPR) technology to measure real-time antibody binding kinetics, immunoglobulin isotypes, and affinity maturation of serum antibodies against the complete ZEBOV proteome daily during acute illness and intermittently during convalescence. This was done to identify the immune markers that correlate with protection and disease resolution naturally in the EVD survivor. To reveal the importance of each antigenic site within ZEBOV-GP as a vaccine antigen, rabbit immunization and mice challenge studies were performed with each GP antigenic site identified in the study to establish that this approach can be used to guide rational vaccine development against EVD.

Results

Figure 9:
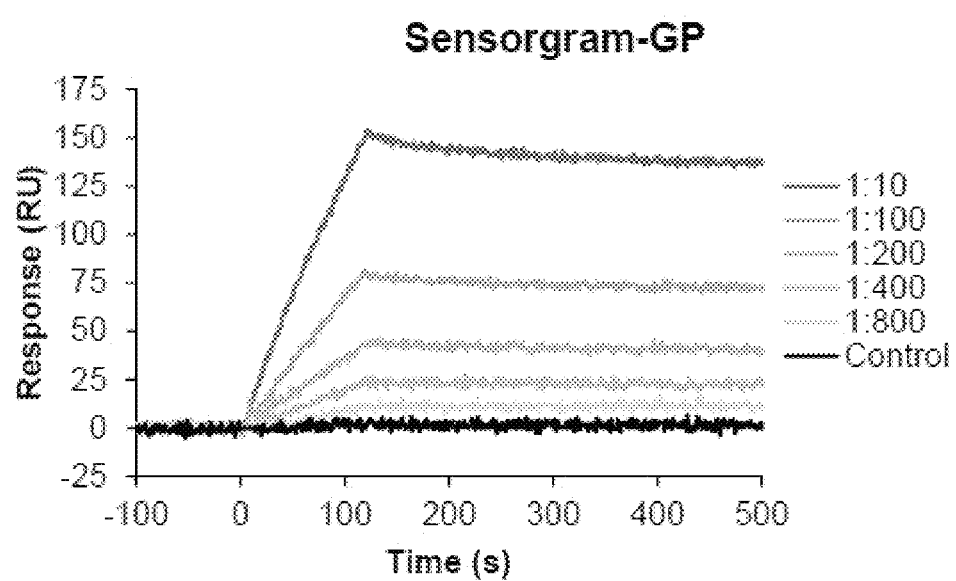
FIG. 9. Steady-state equilibrium analysis of different dilutions of serum antibodies binding to Makona GP by SPR. Serial dilutions of serum samples were injected simultaneously onto both Makona GP captured on a Ni-NTA sensor chip and on a surface free of protein (used as a blank). Binding was recorded using BioRad Proteon surface plasmon resonance biosensor instrument. Responses from the protein surface were corrected for the response from the mock surface and for responses from a separate, buffer only injection. Uninfected (ZEBOV-negative) control sample at 10-fold dilution did not show any binding in SPR. Antibody off-rate constants, which describe the fraction of antigen-antibody complexes that decay per second, were determined directly from the serum sample interaction with GP using SPR in the dissociation phase only for the sensorgrams with Max RU in the range of 10-100 RU and calculated using the BioRad ProteOn manager software for the heterogeneous sample model.
Figure 10:
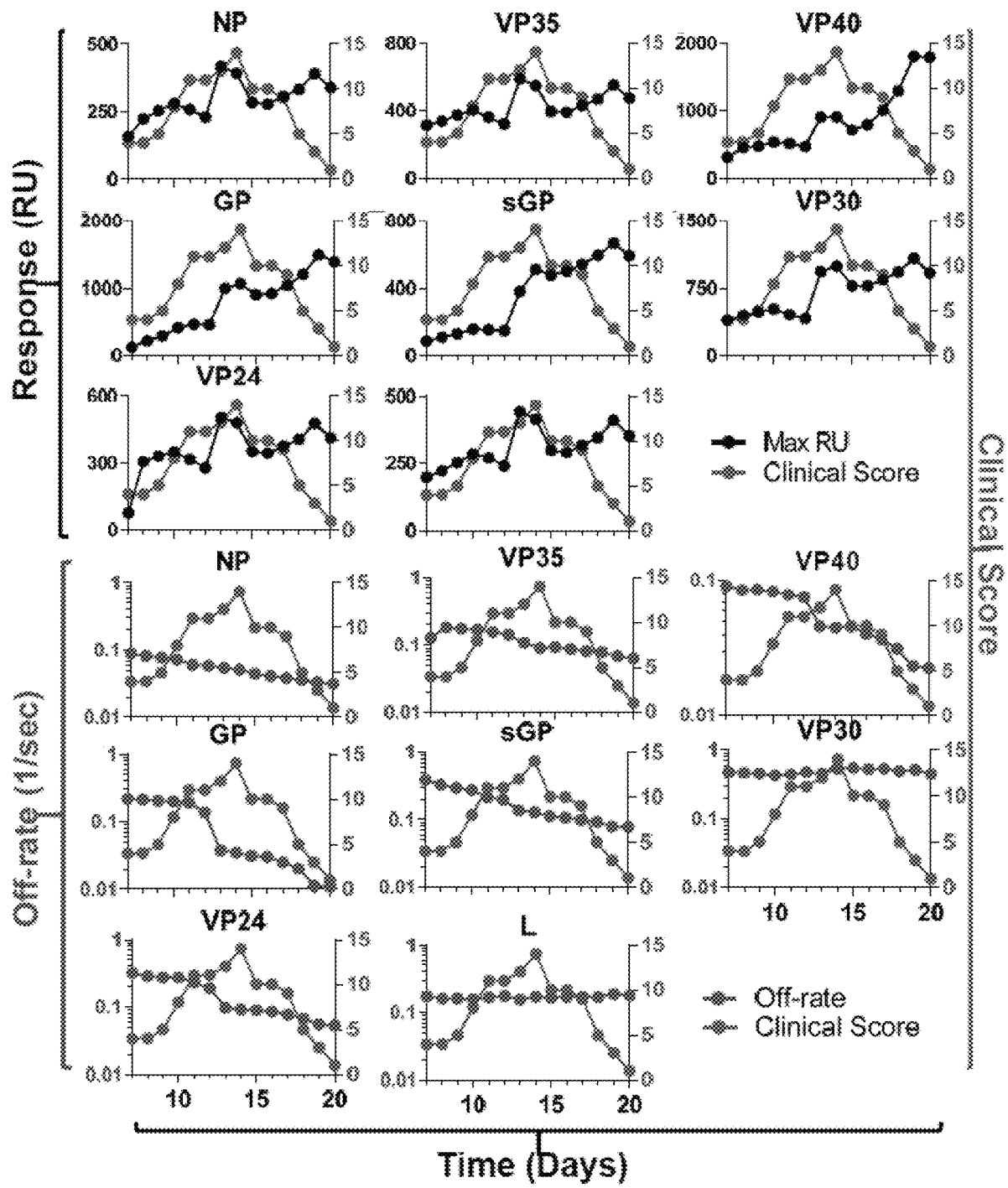
FIG. 10. Relationship of serum antibody binding and antibody affinity to Ebola proteins and clinical scores following ZEBOV infection. Total binding antibody (Max RU; black symbols) or antibody affinity (blue symbols) of human serum against each of the 8 Ebola proteins were plotted with the clinical SOFA scores (red symbols) in the symptomatic phase following ZEBOV infection (days 7-20) in this EVD survivor.

Longitudinal Analysis of Antibody Binding Kinetics of Post-ZEBOV Infection Serum to ZEBOV Proteins Human sera collected daily from a critically ill patient with EVD during acute illness and intermittently during convalescence were evaluated, with all days being relative to the day (D) of symptom onset (Barnes et al. Clin Infect Dis. 65(8), 1400-1403, 2017). The patient had been medically-evacuated from Sierra Leone to the United States and treated at the NIH Clinical Center on a randomized controlled clinical trial comparing an investigational immunotherapy plus standard of care to standard of care alone; in this case the patient had randomized to receive standard of care treatment alone. The viral RNA levels, clinical symptom scores, ZEBOV-IgG/IgM antibodies, GP binding antibodies and neutralization titers during acute illness are shown in FIG. 6. Quantitative and qualitative SPR analyses was performed for several dilutions of polyclonal serum (FIG. 9; shown for GP) using recombinant full-length ZEBOV/Makona proteins except for partial L polymerase. Uninfected control serum did not display antibody binding. Antibody binding titers to most ZEBOV proteins gradually increased from D7 to D12, followed by an inflection point on D13, defined by a pronounced increase in titers against all ZEBOV proteins was observed (FIG. 1A). This increase coincided with an end to viral replication in blood, as determined by strand-specific quantitative reverse transcription polymerase chain reaction testing Kash et al. Sci Transl Med. 9(385), 2017, and a rapid decline in the clinical sequential organ failure assessment (SOFA) score, a validated predictor of death in critically ill patients with severe infection (FIGS. 6 and 10). Overall, VP40 and GP induced the highest antibody binding titers, peaking around days 66/361 and 19, respectively. Serum antibodies against other ZEBOV proteins peaked between day 19-28 and then declined after day 66, but remained consistent against NP, VP35 and VP40 (FIG. 1A).

Figure 11:
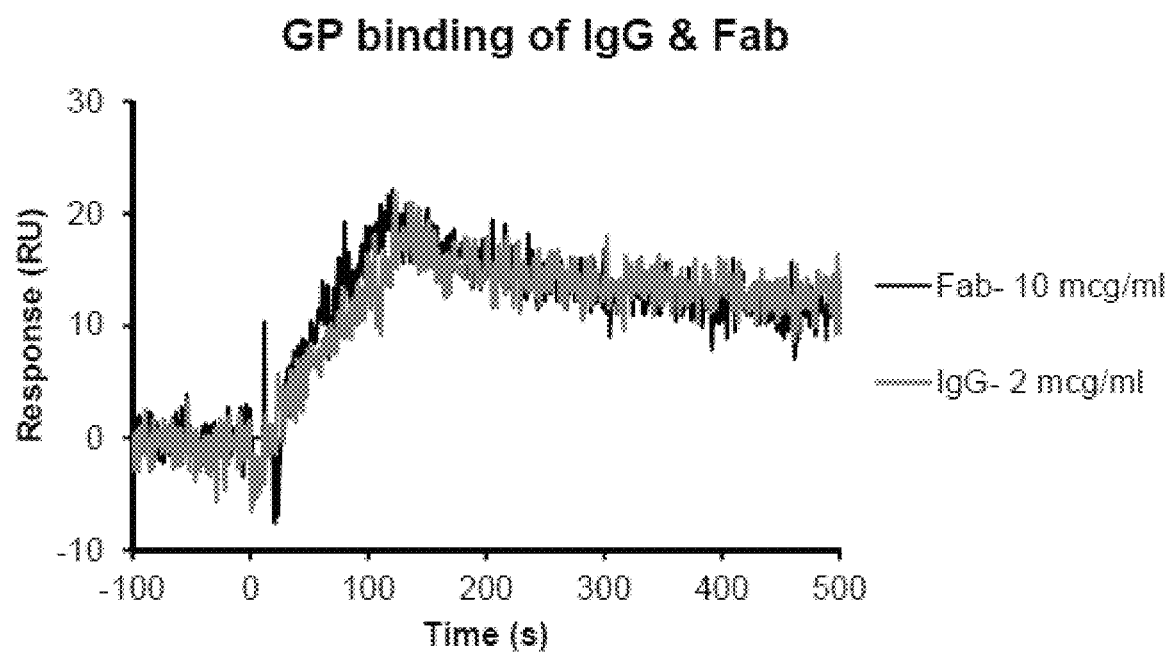
FIG. 11. Steady-state equilibrium analysis of purified IgG and Fab to GP by SPR. IgG and Fab were purified from sera, normalized for the molecular weight and sensor detection of these molecules; and injected simultaneously onto both Makona GP captured on a Ni-NTA sensor chip and on a surface free of protein (used as a blank). Binding was recorded using BioRad Proteon surface plasmon resonance biosensor instrument. Responses from the protein surface were corrected for the response from the mock surface and for responses from a separate, buffer only injection. Antibody off-rate constant, which describe the fraction of antigen-antibody complexes that decay per second, were determined directly from the sample interaction with GP using SPR in the dissociation phase only for the sensorgrams with Max RU in the range of 10-100 RU and calculated using the BioRad ProteOn manager software for the heterogeneous sample model.

Technically, since antibodies are bivalent, the proper term for their binding to multivalent antigens like viruses is avidity, but here the term affinity is used throughout since primarily monovalent interactions were measured (Khurana et al. Nat Commun. 10(1), 3338, 2019). To determine the antibody affinity maturation over time against different ZEBOV proteins following virus infection, the dissociation kinetics (off-rate constants) of antigen-antibody complexes that are independent of antibody concentration were used as a surrogate for overall average affinity of polyclonal antibody against ZEBOV proteins using SPR (Khurana et al. Nat Med. 22(12), 1439-1447, 2016; Khurana et al. Nat Commun. 10(1), 3338, 2019; Khurana et al. Sci Transl Med. 3(85), 85ra48, 2011). Furthermore, to ascertain that the antibody kinetics measured under optimized SPR conditions represent primarily the monovalent interactions between the antibody-antigen complex, IgG was purified from the serum and used to prepare Fab molecules and evaluated for binding to GP in the SPR. The antigen-antibody binding off-rates of the IgG and Fab interaction with Makona GP were very similar when adjusted for molecular weight of the bound IgG and Fab molecules. (FIG. 11).

Figure 12:
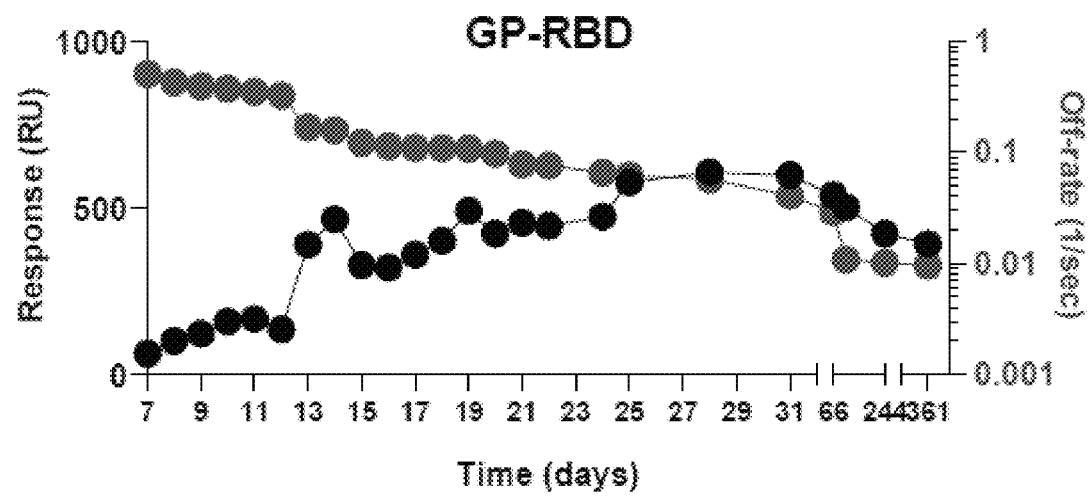
FIG. 12. SPR based analysis of human serum following ZEBOV-infection with purified GP receptor binding domain (GP-RBD). Serial dilutions of serum samples collected at different time points from the ZEBOV survivor were analyzed for antibody binding to purified GP-RBD of SPR. Total antibody binding is represented in SPR resonance units (RU; in black) and is calculated RU for an undiluted serum sample. Binding affinity of serially diluted post-infection serum to GP-RBD was measured and is plotted in blue. Antibody off-rate constants that describe the fraction of antibody-antigen complexes decaying per second were determined directly from the serum sample interaction with GP-RBD using SPR in the dissociation phase. All SPR experiments were performed twice and the data shown is average value of two experimental runs.

At D7, off-rates of polyclonal antibodies bound to ZEBOV proteins were fast (between 0.1 to 1 per second), indicating weak antibody affinity early during illness, that matured thereafter although differentially for various ZEBOV proteins (FIG. 1A). Anti-GP antibodies demonstrated weak affinity maturation through D12 (0.136 per sec), however, an inflection point on D13 was observed defined by a 4-fold increase in antibody affinity in a single day (0.037 per sec). A gradual increase in anti-GP antibody affinity through D31 (0.00713 per sec) was then followed by a remarkable 50-fold increase by D361 (0.00037 per sec) (FIG. 1A). No GP sequence change was observed during acute illness (serum samples) or convalescences (semen samples) in this EVD survivor (Barnes et al. Clin Infect Dis. 65(8), 1400-1403, 2017). The antibody binding and affinity to GP receptor binding domain (GP-RBD) follow the similar antibody kinetics to native GP (FIG. 12). Anti-soluble (s)GP antibodies showed moderate affinity maturation without an inflection point and an off-rate of 0.0052 per sec by D361 (FIG. 1A). Anti-VP40 antibody affinity maturation demonstrated a 10-fold increase from D31 to D361 (0.0161 on D31 to 0.00109 on D361 per sec) (FIG. 1A). Binding antibodies against NP, VP35 and VP24 affinity matured slowly over time to reach off-rates of 0.01 per sec by D361 (FIG. 1A). Minimal affinity maturation was observed for anti-L and anti-VP30 antibodies with off-rate around 0.1/sec by D361 (FIG. 1A). The inflection point observed on day 13 for the predominant increase in anti-GP antibody affinity was followed by a rapid decline in clinical SOFA score from day 14 onwards (FIG. 1B). The clinical scores and viral load decreased before an increase in neutralizing titers was measured in the PRNT80 assay, indicating that neutralizing antibodies may not be of key importance to control ZEBOV infection or that sensitivity of the PRNT80 assay is low in determining the functional immune response that curtails viral infection (FIG. 6).

Class-Switching of Binding Antibodies to ZEBOV Proteins after ZEBOV Infection

Isotype analysis of binding antibodies was performed by SPR across ZEBOV proteins (FIG. 1B) and demonstrated the presence of IgM, IgA, and IgG in post-infection sera. The absence of GP antibody binding for uninfected control human sample excluded the possibility that IgM binding may be due to polyreactive natural antibodies (i.e. sticky antibodies not induced by ZEBOV) in SPR (FIG. 9) (Khurana et al. Nat Med. 22(12), 1439-1447, 2016). On D7, the majority of the ZEBOV protein binding antibodies were of IgM isotype, which class switched gradually with increasing contribution from IgA and IgG isotypes over time apart from VP24 and L (FIG. 1B). After D31, IgA binding antibodies declined against most ZEBOV proteins while IgG antibodies increased ~60% against GP and VP40, ~33% against NP, and <15% against VP35, VP30, VP24 and L proteins by D361. Further IgG subclass analysis of antibodies revealed predominance of IgG2 and IgG3 at early time points against NP, VP35, VP40, and VP24 with increased contribution by IgG4 by D66 and a predominance of IgG1 by D361 (FIG. 13).

Evolution of Whole Genome Antigenic Fingerprint Generated Following ZEBOV Infection The polyclonal antibody epitope repertoire of post-ZEBOV infection IgM, IgG and IgA antibodies in longitudinal sera on days 7, 13, 19, 31, 110 and 361 post-symptom onsets was analyzed by GFPDL containing sequences ranging from 50-1000 bp long from the complete ZEBOV/Makona genome with >$10^{7.7}$ unique phage clones (FIG. 14). The ZEBOV-GFPDL displayed linear and conformational epitopes with random distribution of size and sequence of inserts that spanned the entire ZEBOV genome (FIG. 15) (Khurana et al. Nat Med. 22(12), 1439-1447, 2016). The ZEBOV-GFPDL adsorbed >90% of ZEBOV-GP specific antibodies in the post-infection polyclonal human sera (FIG. 16) supporting the use of the ZEBOV GFPDL for repertoire analyses of human sera. Serum specimens were evaluated to delineate the IgM, IgG, and IgA epitope specificities across ZEBOV proteins (Table 2 and FIG. 2). An uninfected (ZEBOV-negative) control human sera bound very few phages. The number of bound phages was highest for IgM antibodies at early time points (D7 to D31) and remained consistent through D361. IgG specific phage titers increased over time reaching IgM antibody levels by D110. However, IgA specific phage titers peaked at D31 and were ~20 to 100-fold lower than phage titers for IgM antibodies.

IgM repertoire evolved further with additional epitopes recognized in NP, diverse immunodominant profile in VP40 and GP, and a decline in VP24 clones (FIGS. 17-22 and 7) in this EVD survivor.

The IgG antibody repertoire was limited at D7 with few recognized epitopes at the N- and C-terminus of NP, VP40 and GP. By D13, more IgG recognized C-terminus of NP, VP35, VP40 and GP, that evolved to predominant GP binding antibodies on days 19 and 31, with contribution from antibodies binding to additional sites focused to two regions each in VP35 and VP40 (FIG. 2A). The IgG profile further matured by days 110 and 361 with antibody binding primarily to two immunodominant regions in VP40 and several sites in GP. IgG response to VP30 was focused to the N-terminal site with few phage clones binding at early time points (D7-D19) that declined following recovery. IgG response to VP35 increased transiently at D31 but declined by D110 with minimal phage reactivity observed at D361. IgG binding phages that mapped to N- and C-terminal sites in VP40 at D7 evolved over time to a high titer anti-VP40 IgG repertoire by days 110 and 361. IgG response to GP at days 7 and 31 was focused to epitopes within the glycan cap and mucin like domain (MLD) of GP1, with limited binding to the fusion peptide and GP2. By D110 in addition to GP1 sites, the GP IgG repertoire evolved to preferentially recognize the fusion peptide and C-terminus of GP2 that predominated at D361 (FIG. 2A). Additional antibodies recognized small epitopes in the N-terminus, between the receptor binding region (RBR) and within the glycan cap domain of GP. While several antigenic sites were previously identified following recombinant vesicular stomatitis (rVSV)-ZEBOV GP vaccination (Khurana et al. Nat Med. 22(12), 1439-1447, 2016), ZEBOV infection induced a more diverse anti-GP antibody response across both GP1 and GP2 (FIG. 7; marked with asterisk in the table).

Figure 2B:
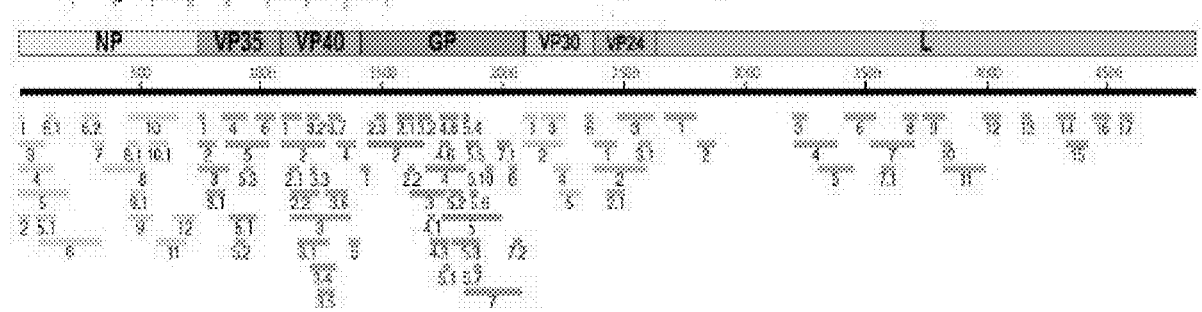

EBOV infection generated a diverse antibody response across the ZEBOV proteome defined by multiple antigenic regions (FIG. 2B). Antigenic regions of 21 to 254 amino acid residues were defined based on antibody recognition by at least 4% of phage clones obtained after affinity selection on IgM/IgG/IgA antibodies with at least one serum sample at

TABLE 2

Distribution of phage clones after affinity selection on post-ZEBOV infection sera

|     | D7       | D13      | D19      | D31      | D110     | D361     |
|-----|----------|----------|----------|----------|----------|----------|
| IgM | 9.90E+03 | 2.18E+04 | 1.77E+04 | 2.51E+04 | 2.36E+04 | 2.05E+04 |
| IgG | 1.00E+02 | 4.20E+03 | 2.40E+03 | 3.93E+03 | 1.20E+04 | 2.28E+04 |
| IgA | 1.10E+02 | 7.40E+02 | 1.60E+02 | 1.35E+03 | 2.00E+02 | 4.20E+02 |

Table 2 shows the number of IgM, IgG and IgA bound phage clones selected using whole genome ZEBOV GFPDL on polyclonal sera from various days 7 (D7), 13 (D13), 19 (D19), 31 (D31), 110 (D110) and 361 (D361) following symptom onset in severely ill EVD survivor.

EBOV sequences expressed by phages bound by post-infection IgM antibodies showed a diverse epitope repertoire distribution, displaying small and large sequences spanning the entire ZEBOV proteome, apart from L (FIGS. 2A and 7). D7 serum IgM antibodies recognized antigenic sites in N-terminal of NP and VP35, multiple sites within VP40 and GP, and few sites within VP30 and VP24 (FIGS. 17-22). By D31 IgM epitope profile evolved with additional binding to sites in C-terminus of VP35 and marginal decline in antibody binding to sites in N-terminal half of GP. By D361 the any time point. The frequency of phages expressing these antigenic sites selected by serum samples for each of the ZEBOV proteins are shown in FIGS. 17-22 and 7. Most of these GFPDL identified antigenic sites were exposed on surface of the ZEBOV protein structures (FIGS. 23-24). The antibody response from ZEBOV infection identified several Filovirus epitopes that elicit an antibody response that is indicative of Filovirus infection in a subject. Peptide sequences containing these epitopes are listed in Table 1 above.

Figure 3:
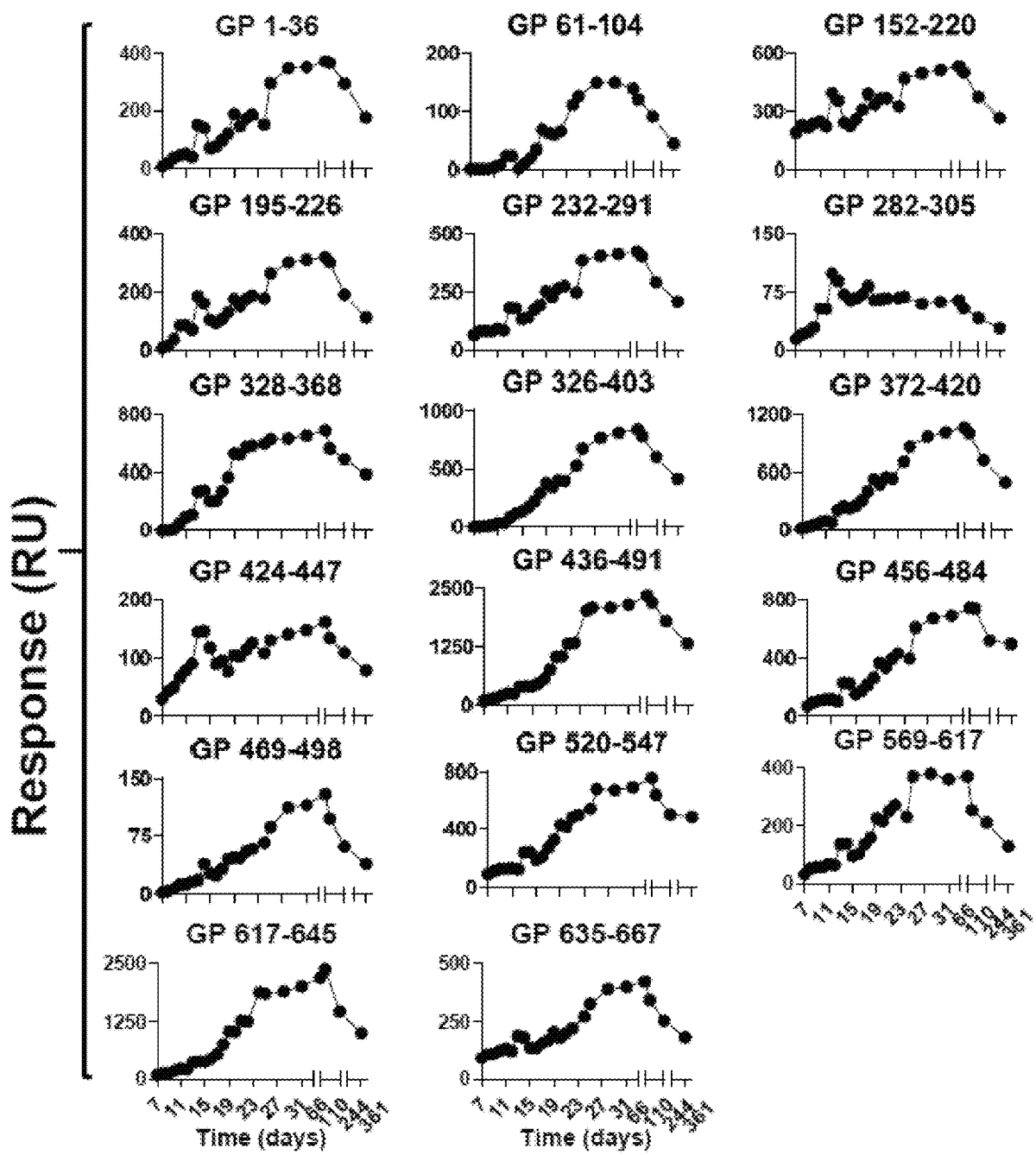
FIG. 3. Analysis of post-ZEBOV infection human serum binding to GFPDL identified GP antigenic site peptides by SPR. Ten-fold dilution of serum samples at each time point collected from ZEBOV survivor were analyzed for total binding to chemically synthesized peptides containing the antigenic sites identified by GFPDL (FIG. 2) in SPR. Total antibody binding of each serum sample at different time points against the peptide is represented in SPR resonance units. The data shown is average value of two experimental SPR runs. The variation for each sample in duplicate SPR runs was <6%.
Figure 25:
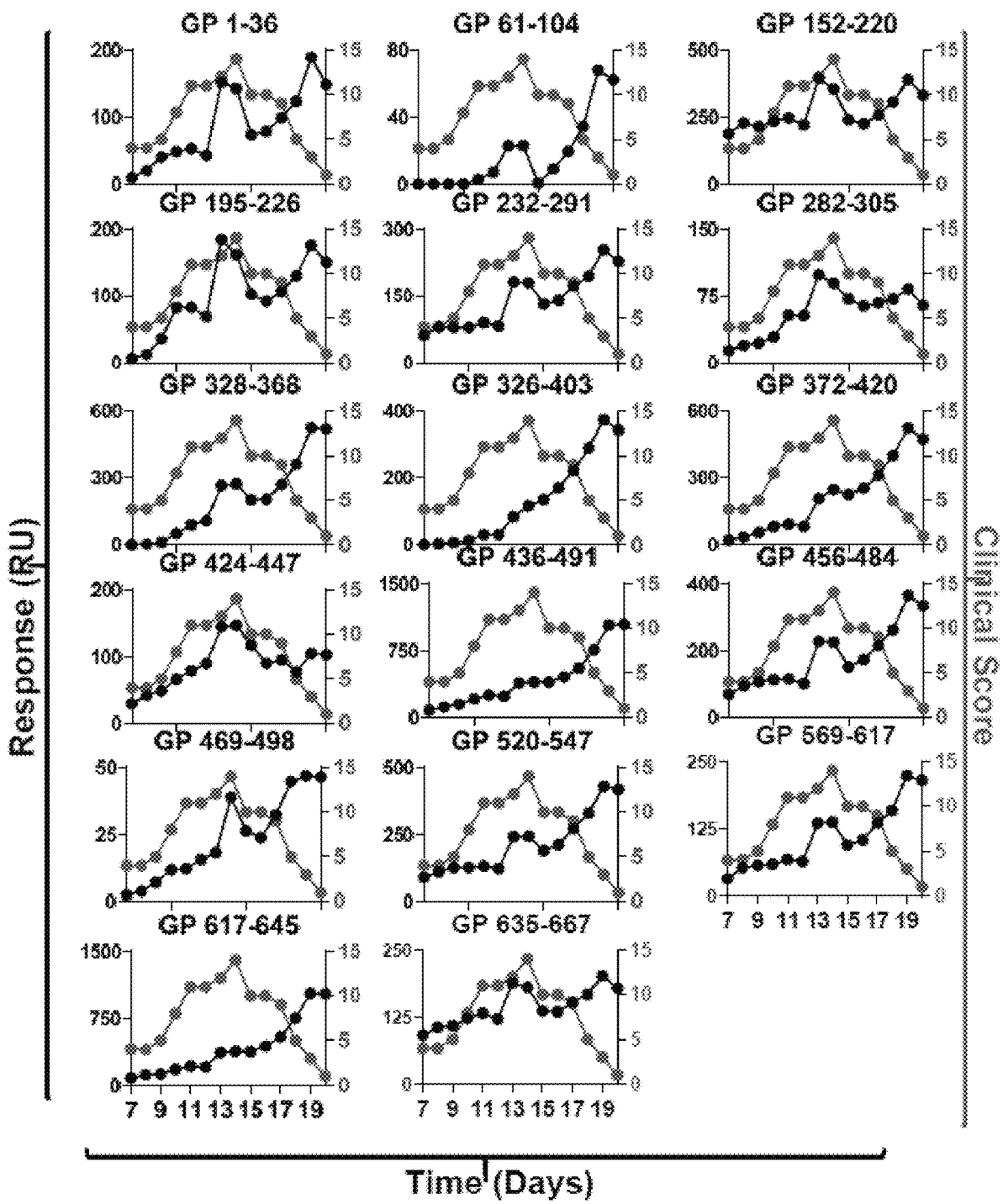
FIG. 25. Relationship of serum reactivity to GP antigenic site peptides and clinical symptom scores following ZEBOV infection. Total binding antibody (Max RU) of human serum against each of the GP antigenic site peptides were plotted with the clinical scores in the symptomatic phase following ZEBOV infection (days 7-20) in this survivor.

Evolution of Post-ZEBOV Infection Antibody Binding to Diverse Antigenic Sites in GP To follow up on antigenic sites in GP identified using GFPDL analysis, peptides representing most of the unique antigenic sites up to 70 amino acid residues long were chemically synthesized and evaluated for antibody binding with longitudinal samples in SPR (FIG. 3). The antibody kinetics of post-infection samples to most GP peptides evolved with similar trends, however the absolute total binding antibodies against different antigenic sites varied at different time points. The measured serum sample reactivity against each peptide in SPR is possibly an aggregate sum of different antibodies recognizing overlapping epitopes in multiple antigenic sites (as defined by the GFPDL in FIG. 2) contained within that peptide sequence. The inflection point observed on D13 with intact GP with sudden increase in binding antibodies (FIG. 1D) was also seen for binding antibodies against most GP peptides apart from GP 326-403. There was a second inflection point on D25 defined by pronounced increase in antibody binding for most peptides but not for some of the antigenic sites located in the glycan cap and mucin-like domain of GP1 (GP 282-305, GP 328-368 and GP 424-447). The increase in binding antibodies to most GP peptides corresponded with the decline in clinical SOFA scores for this patient (FIG. 25). Binding antibodies against most antigenic sites within GP peaked on D66 and D110 with highest reactivity to C-terminal of GP2 encompassing HR2-TM region (GP 617-645; 2372 RU) and C-terminus of GP1 (GP 436-491; 2348 RU) followed by peptides in the MLD and glycan cap region (GP 329-368; 689 RU, GP 372-420; 1061 RU and GP 326-403; 781 RU) and in the GP2 fusion peptide (GP 520-547; 756 RU). The antibody decay/decline after D66 was faster for antibodies targeting most sites, while the antibodies to C-terminal of GP1, fusion peptides and some GP2 antigenic sites at day 361 post-onset were at least 50% of their peak titers (FIG. 3).

Binding, Cross-Reactivity & Neutralization Potential of ZEBOV-GP Antigenic Sites: Rabbit Immunization Studies Since ZEBOV-GP is target for vaccine and therapeutic development against EVD, the contribution of these GFPDL identified GP antigenic sites as an immunogen to generate ZEBOV neutralizing antibodies were evaluated. Rabbits were immunized with the 15-individual KLH-conjugated synthetic peptides representing most of the antigenic sites up to 70 amino acid residues long. Immunization of rabbits with selected ZEBOV antigenic site peptides generated strong binding antibodies against GP from the Makona and Mayinga ZEBOV isolates (FIG. 4A) with minimal or no binding to SUDV GP, except antibodies raised against peptide GP 617-645, likely due to high (79%) sequence conservation with SUDV GP in this region. (FIGS. 8 and 26).

To evaluate the neutralization activity of the rabbit anti-GP peptide immune sera, a pseudovirion neutralization (PsVN) assay was performed against ZEBOV/Mayinga. Five antigenic peptides generated neutralizing antibodies including GP 282-305, GP 343-368, GP 469-498, GP 520-547, and GP 617-645 (FIG. 4B). Three peptides (GP 469-498, GP 520-547, and GP 617-645) also neutralized ZEBOV/Kikwit, while only the GP2 peptide (site VI; GP 617-645) generated antibodies that neutralized SUDV in the PsVN assay. In PsVN assay without complement, neutralization titers were on average 2-fold lower than in the presence of complement (5% Guinea Pig Complement) shown in FIG. 4B. Two of these peptides, one from the carboxy terminus of GP1 (V.7; GP 469-498) and another in the C-terminus of GP2-HR2 domain (VI; GP 617-645), generated strong neutralizing titers against wild type ZEBOV/Makona in the conventional BSL4-based plaque reduction neutralization test (PRNT) with end-point titers of 640 and 320, respectively (FIG. 4B).

These rabbit studies confirmed that GFPDL identified antigenic GP peptides are immunogenic as they can elicit antibodies that bind GP from ZEBOV isolates. Importantly, five of these peptides including conserved antigenic sites in C-termini of GP1 and GP2 induced neutralizing antibodies. Spatial structure of these neutralizing antigenic sites on the ZEBOV GP crystal structure of the ZEBOV/Makona-GP (PDB Id #6DZL) (Murin et al. Cell Rep. 24(10), 2723-2732 e2724, 2018); and the model of complete ZEBOV GP monomer are shown in FIGS. 4C-4D. Based on the surface representation, these five targets of neutralizing antibodies discovered in this study are exposed on the native ZEBOV GP structures.

EBOV-GP Protective Antigenic Sites: Mice Immunization and Challenge Studies

To further understand the importance of these neutralizing antigenic sites in providing protection against ZEBOV, mouse ZEBOV challenge studies were performed using the 5 antigenic site peptides that generated ZEBOV neutralizing antibodies in rabbits. Female C57Bl/6 mice (N=10 per group) were immunized on days 0 and 29 intra-muscularly, with 20 micrograms of the five KLH-conjugated peptides (FIG. 5A). Additionally, one group of mice was vaccinated with a combination of the KLH-peptides (at 4 microgram each). Control groups of mice were injected with 20 micrograms of KLH only (negative control), or with an ZEBOV GP—Venezuelan equine encephalitis virus (VEEV) replicon particle-based vaccine (VRP) expressing full length ZEBOV GP (positive control) (FIG. 5A).

Figure 27:
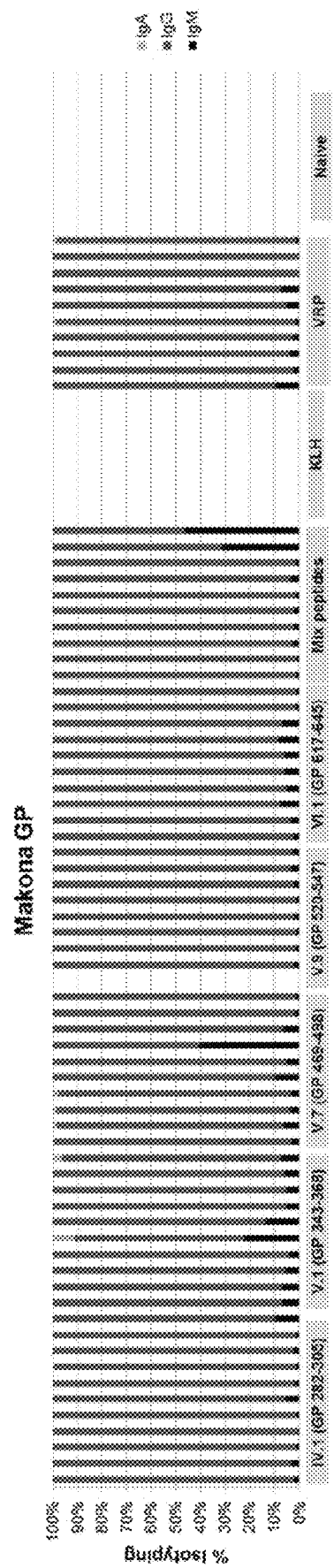
FIG. 27. SPR based isotyping of Makona GP binding antibodies in post-immunization mouse sera. Antibody isotype of ZEBOV/Makona GP binding antibodies (shown in FIG. 4B) following second (boost) immunization sera from mice immunized with KLH conjugated antigenic site peptides by SPR. The resonance units for each anti-GP antibody isotype (IgA in green, IgG in red, and IgM in black) was divided by the total resonance units for all antibody isotypes combined to calculate the percentage of each antibody isotype for individual serum sample.
Figure 29:
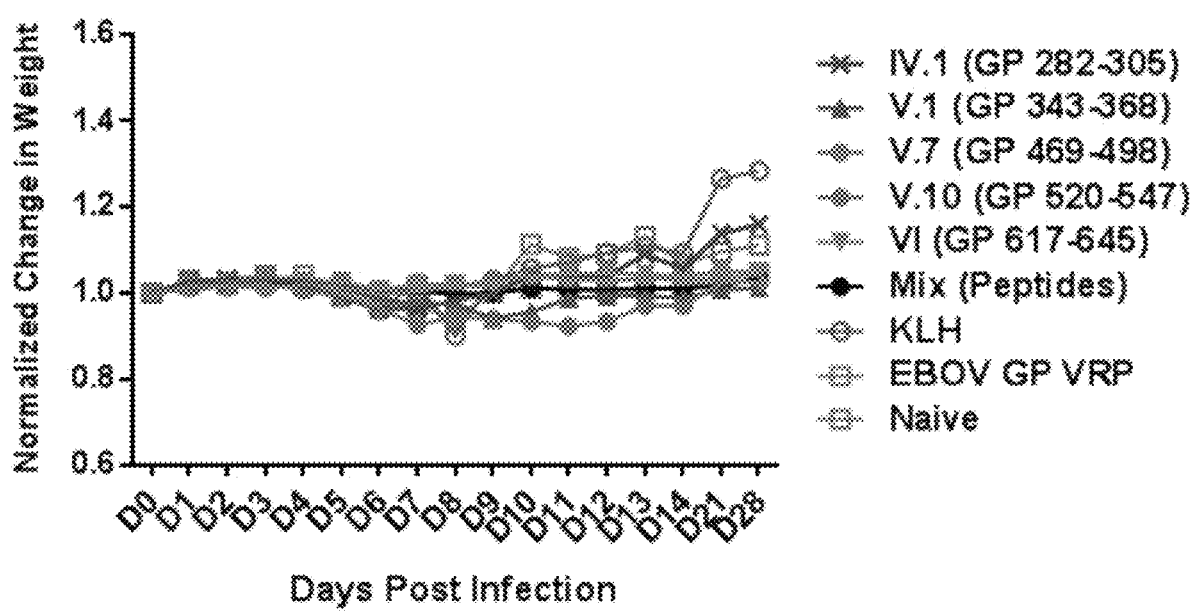
FIG. 29. Change in body weight of surviving mice following ma7EBOV virus challenge. ZEBOV-challenged animals were weighed daily for the first 14 days and every week thereafter up to 28 days following ma7EBOV infection. Weight of each individual mice were normalized to their original body weight on day of ma7EBOV challenge.

Following immunization but prior to the viral challenge, sera was collected on day 57 (28 days following second vaccine dose) to analyze the immune response against GP by SPR. The conserved antigenic sites in the C-terminal region of GP1 (V.7) and GP2 (VI) generated strong binding antibodies to native GP of both ZEBOV/Makona (FIG. 5B) and ZEBOV/Mayinga (FIG. 5C) comparable to that induced by the positive control VRP in SPR. The other antigenic site peptides generated moderate (V.1; GP 343-368) to weak (IV.1; GP 282-305, V.9; GP 520-547) GP binding antibodies. SPR based isotyping of the post-vaccination mouse serum revealed that >95% of GP binding antibodies were IgG (FIG. 27). These findings were confirmed by GP-IgG ELISA that suggested that second (boost) vaccination had a minimal impact on the GP binding antibody titers (FIG. 28). The GP-binding antibodies follow similar reactivity trends against both Makona and Mayinga strains for most post-$2^{nd}$ vaccination sera in SPR and ELISA. At day 63, the mice were challenged with 100 pfu wild type (mouse-adapted) ZEBOV strain (ma7EBOV) and were followed for mortality (FIG. 5D) and weight loss (FIG. 29). Vaccination with the conserved antigenic sites in C-terminus of GP1 (V.7; GP 469-498) and GP2 (VI; GP 617-645) provided complete protection (100% survival) against challenge, similar to the VRP control group and the group vaccinated with peptide mix (FIG. 5D) and protected against weight loss (FIG. 29). The other antigenic site peptides only conferred moderate (V.1; GP 343-368) to minimal (IV.1; GP 282-305, V.9; GP 520-547) protection from mortality following ma7EBOV challenge. The peptide mixture containing $\frac{1}{5}^{th}$ of each individual peptide provided 90% protection suggests that 4 µg of the relevant immunogen may be sufficient for protective immunity. The protection against lethality induced following ma7EBOV challenge mediated through neutralization and other mechanisms seems to correlate with the titer of GP binding antibodies induced following second vaccination. These protective antigenic sites identified in the current study are located either at the base (site V.7) or in the stalk domain of GP (site VI) close to the viral membrane (FIG. 4D). Analysis of sequence homology of GP showed that antigenic site VI is highly conserved between diverse Ebolavirus species including SUDV (79%) and BDBV (92%) (FIG. 8). As a vaccine, novel antigenic sites at the C-terminus of GP1 and in highly conserved GP2-HR2, conferred 100% protection in mice against lethal ZEBOV challenge.

DISCUSSION

This example represents the most comprehensive longitudinal characterization of antibody responses across the complete ZEBOV proteome in a critically ill patient with EVD who survived with supportive care alone without experimental therapies. Some of the differences between this study versus previous studies (Davis et al. Cell. 177(6), 1566-1582 e1517, 2019; McElroy et al. Clin Infect Dis. 63(4), 460-467, 2016; Saphire et al. Cell. 174(4), 938-952 e913, 2018) are: i) this study describes a critically ill acutely infected ZEBOV patient who survived without any experimental treatment, while previous studies describe patients that received antibody treatment (ZMapp or convalescent plasma) at early time post-symptom onset (the antibody therapeutic treatment can have significant impact on the study conclusions); ii) this study performed comprehensive longitudinal analysis against complete ZEBOV proteome including antigenic epitope mapping of IgM, IgG and IgA every day following acute ZEBOV infection, while other studies primarily looked at GP responses and only IgG response to NP and VP40 without determining epitope specificity of these antibodies; iii) the daily longitudinal analysis performed in this study starts on day 7 post-symptom onset, prior to peak in symptoms and before the viral decline/disease resolution to identify the immune markers that correlate with protection naturally in this EVD survivor, while other studies described experimentally antibody treated patients primarily after their peak in symptoms; iv) to identify the immune signature providing protection during natural ZEBOV infection, the antigenic sites identified by GFPDL were evaluated as vaccine for their contribution to ZEBOV neutralization (Rabbit studies) and protective vaccine efficacy (mouse) ZEBOV in lethal challenge studies, while previous studies produced anti-GP MAbs once the EVD symptoms have been resolved in these EVD survivors, without any vaccination studies to evaluate the contribution of different GP antigenic sites in neutralization/protection. This study is the first study that shows the contribution of the different epitopes as a vaccine for ZEBOV neutralization and protection against EVD. Antibody parameters and immunodominant antibody responses to ZEBOV GP epitopes were identified that coincided with disease resolution in this EVD survivor. Novel antigenic sites in the C-terminus of GP1 and a highly conserved site in the base of GP2 induced neutralizing antibodies in rabbits and provided complete protection in mice from lethal ZEBOV challenge. The findings indicate that close daily immunological characterization of the host-viral interaction can identify immune markers of protection that may help guide rational vaccine design and facilitate development and evaluation of more targeted immune-based countermeasures against EVD.

Over the course of the patient's illness, a differentially evolving diverse antibody response was observed, in terms of antibody epitope repertoire, isotype class switch, and affinity maturation. An inflection point with rapid rise in antibody titers against all ZEBOV proteins was observed on illness D13, with GP antibodies displaying the greatest single-day rise in titer and affinity maturation that associated with a rapid decline in clinical SOFA score thereafter. VP40 and to a lesser extent VP30 also induced high titer and affinity antibodies that persisted through D361. Although the IgG response on D7 was limited, it evolved to focus on immunodominant sites within VP40 and GP. The kinetics of the IgA repertoire emerged to peak both in binding and diversity approximately one-month post-symptom onset and then declined. This differential antibody kinetics to various ZEBOV proteins suggests disparate expression and/or antigen exposure/recognition by the human immune system following ZEBOV infection in this EVD survivor that should be validated in a larger cohort. VP40 and GP antibodies accounted for >70% of IgG and IgA with high affinity during convalescence. The relevance of IgA titers is unclear but may be important at mucosal sites and in semen. The presence of IgG2 isotype binding antibodies during acute and convalescent illness suggest a possible polysaccharide antigen-induced class switching to IgG2 following ZEBOV infection. IgG3 are potent mediators of effector functions, including antibody-dependent cellular cytotoxicity, complement activation, and neutralization. The observed differential antibody kinetics and class switching with early IgG3 response followed by a later IgG2 response may be related to antigen drive but equally likely to be driven by the severe cytokine storm during acute ZEBOV infection. Therefore, to understand the relevance of these antibody kinetics, it would be important to investigate antibody profile between ZEBOV-infected persons based on differential clinical outcome. High levels of IgG3 detected against GP, VP24 and VP40 at early time points post-ZEBOV infection potentially may have been associated with control or protection possibly by Fc-mediated functions as was observed against a range of intracellular bacteria and viruses (Lu et al., 2018).

A high titer, durable high affinity antibody response was observed against the most abundant ZEBOV protein VP40, which plays an essential role in virus particle assembly and budding, as well as suppression of host defenses and evasion/tolerance by ZEBOV of host immune response (Yamayoshi and Kawaoka. J Infect Dis. 196 Suppl 2, S291-295, 2007). The anti-VP40 inflection point for both titers and affinity on D13 preceding decline of clinical symptoms on D14 onwards suggests a potential role of VP40 antibodies in protection from disease and, accordingly, provides support for the role of the VP40 protein as a potential vaccine or therapeutic target (Madara et al. Future Virol. 10(5), 537-546, 2015; Wilson et al. Virology. 286(2), 384-390, 2001. Recently it was observed that combination of GP with VP24 and VP40 induced stronger antibody responses and promoted protection in mice. VP24 was also shown to induce protection via cell-mediated immunity demonstrating potential for this as an additional vaccine antigen (Lehrer et al. Vaccine, 37(47:6942-6950, 2019.

The GP specific antibody repertoire induced by ZEBOV infection in the patient showed greater diversity, antibody class switching, and affinity maturation compared to rVSV-ZEBOV GP prime-boost vaccination induced antibody responses (Khurana et al. Nat Med. 22(12), 1439-1447, 2016). ZEBOV infection-induced GP binding antibodies in the patient provided a durable response up to 12 months post-infection, in contrast to the rVSV-ZEBOV GP prime-boost vaccination that induced a short-lived response, with a decline to low antibody levels by six months post-vaccination (Khurana et al. Nat Med. 22(12), 1439-1447, 2016). Importantly, the patient demonstrated strong antibody binding to C-terminal sequences of GP1 and GP2 compared with rVSV-ZEBOV GP vaccination where the humoral response was primarily focused to the glycan cap and MLD sites perhaps due to the limited vector replication compared with productive ZEBOV infection that can stimulate the immune system over a prolonged period. One of the possible limitations of GFPDL-based assessments is that while the phage display is likely to detect both conformational and linear epitopes on ZEBOV proteins, they are unlikely to detect paratopic interactions that require post-translational modifications and rare quaternary epitopes that cross-protomers. However, in the current example (FIG. 16) and a prior study with post-rVSV-Ebola GP vaccination serum polyclonal antibodies, 86-91% of anti-GP antibodies were removed by adsorption with the ZEBOV-GFPDL, supporting the use of the ZEBOV-GP GFPDL for analyses of human sera (Khurana et al. Nat Med. 22(12), 1439-1447, 2016).

During convalescence, viral RNA was detected in the patient's semen on D32 (Ct=18.47), D66 (Ct=29.71) and D110 (Ct=30.07), but was below limit of detection by reverse transcription quantitative polymerase chain reaction (RT-qPCR) assay on days 244 and 361 (Barnes et al. Clin Infect Dis. 65(8), 1400-1403, 2017). By D361 however, binding antibodies against 5 of 7 ZEBOV proteins consisted of >50% IgM antibodies, suggesting persistent immune system exposure to ZEBOV antigens despite inability to detect virus by RT-qPCR (Barnes et al. Clin Infect Dis. 65(8), 1400-1403, 2017). Moreover, the presence of ZEBOV specific IgG4 at different time points suggests persistent infection or long-term exposure to antigen following ZEBOV infection or may even reflect persistent class-switched IgM memory contributing to the serum. Finally, IgM antibody epitope repertoire generated following ZEBOV infection during acute illness was very diverse across the entire ZEBOV proteome and remained consistently diverse during convalescence, further suggesting persistent ZEBOV antigen exposure as late as D361. These findings are consistent with those of PREVAIL III, a longitudinal prospective cohort study of EVD survivors and controls, where 30% of 267 male survivors had viral RNA detected in semen on average 19 months following acute illness and 44% of those men had 2 negative tests followed by a positive test (Group et al. N Engl J Med. 380(10), 924-934, 2019). However, the potential presence of virus in immune privileged sites in this EVD survivor, suggests that antibody response induced following infection in EVD survivors is limited in providing protection/clearance of ZEBOV infection at these hidden sites (including eyes, testis etc.) even after virus has long been cleared in blood/plasma. The findings of an IgM antibody signature during convalescence, despite undetectable virus by RT-qPCR assay, raise potential for GFPDL-based detection of viral persistence among survivors. Such a diagnostic assay could potentially guide use of experimental therapies to facilitate viral clearance and potentially mitigate sequela among survivors.

To identify immunodominant epitopes in GP the patient's polyclonal sera was tested against peptides covering most antigenic sites. Antibody binding against these peptides showed differential evolution of kinetics indicative of a dynamic process of antibody-antigen interaction recognizing epitopes in overlapping antigenic sites following ZEBOV infection. Antibody titers generated against antigenic sites in C-terminus of GP1 (GP 436-491) and the HR2-TM region on GP2 (GP 617-645) far exceeded those of other peptides in this EVD survivor. Since most advanced ZEBOV vaccines in clinical trials employ GP as vaccine target, the contribution of GFPDL identified immunodominant antigenic sites in ZEBOV-GP to virus neutralization were investigated, peptides representing most antigenic sites up to 70 amino acid residues long were used for immunization of rabbits and screening in ZEBOV neutralization assays. Although all rabbit anti-peptide sera bound ZEBOV/Makona GP, antibodies against only 5 antigenic sites showed neutralization titers in PsVN assay, and only antibodies against sites in C-termini of GP1 (GP 469-498) and GP2 (GP 617-645) neutralized wild type ZEBOV/Makona virus in BSL4-based PRNT (FIG. 5B). The same two C-termini antigenic site peptides (GP 469-498 and GP 617-645) provided mice 100% protection against lethal ZEBOV challenge. Antibodies directed against ZEBOV-GP can inhibit viral entry and/or release. While the antibody impact on virus release has not been studied, the partial protection mediated by peptide V.1 in the absence of entry inhibiting antibodies could be explained, at least in part, by antibodies blocking virus release in the mice challenge studies. The focus on GP for protective vaccination studies is primarily because currently all ZEBOV vaccines or antibody-based therapeutics in advanced clinical development target ZEBOV-GP. Current ZEBOV vaccines generate suboptimal antibody response primarily focused to non-neutralizing sites in glycan cap and mucin-like domain, mostly IgM, and this IgM response is not durable in humans (Khurana et al. Nat Med. 22(12), 1439-1447, 2016). Animal studies were performed to identify critical protective antigenic sites within GP identified by antibodies post-acute ZEBOV infection, that can be used to design immune-focused more effective Filovirus vaccines.

The rapid resolution of dissemination, intravascular coagulation and acute kidney injury (Chertow et al. Ann Intern Med. 165(4), 301-304, 2016), causing an overall reduction in the clinical SOFA score, was immediately preceded by a surge in high-titer, high-affinity GP antibodies with immunodominance of epitopes at the C-terminus of GP1 and base of GP2 in this EVD survivor. These peptides induced neutralizing antibodies in mice and rabbits and protected mice against lethal ZEBOV challenge. Antibodies generated against the highly conserved site in base of GP2 (GP 617-645) induced cross-reactive binding against diverse filovirus strains, raising potential for a cross reactive vaccine across ZEBOV species. While others have focused on evaluation of the functional characteristics of antibody responses among ZEBOV survivors to guide monoclonal antibody-based therapeutic design (Saphire et al., 2018), it is believed that this is the first study to utilize a high-fidelity analysis of humoral responses daily during acute illness and during convalescence to identify immune markers of protection and guide peptide-based vaccine design.

In summary, this longitudinal analysis study demonstrated a differential evolving antigenic fingerprint following ZEBOV infection across the ZEBOV proteome in terms of antibody epitope repertoire diversity, antibody isotype class switching, and antibody affinity maturation in a survivor whose natural host response was unaffected by any investigational treatments. Antibodies targeting several of these antigenic sites possessed ZEBOV neutralizing activity in vitro and showed an important role for the C-terminus of GP1 and highly conserved site in GP2 for providing protection in the lethal ZEBOV mice challenge studies. These observations provide a more in-depth understanding of quantitative and qualitative aspects of immune responses that are protective and which can aid development and evaluation of targeted more effective ZEBOV therapeutics and vaccines.

Methods

Proteins, Serum samples and Monoclonal Antibodies

Recombinant ZEBOV proteins of Makona-2014 strain were purchased from Sino Biologicals, MyBioSource, and IBT Bioservices Inc. All recombinant GP purified proteins used in the study were produced in mammalian cells. The gamma irradiated clinical serum samples were obtained from NIH (FIG. 6) (Wilkinson et al. Vaccine. 35(9), 1347-1352, 2017). In March 2015, a 34-year-old male health care worker was evacuated from Sierra Leone on day (D) 7 of documented EVD symptoms to the United States National Institutes of Health Clinical Research Center (ClinicalTrials.gov Identifier: NCT02363322; NIH IRB protocol #15-I-0083). Serum samples were collected daily from D7 to 31 and then in the convalescent phase (all days are post symptom onset). Viral RNA in blood peaked at D8 (cycle threshold, Ct=23.21) and became undetectable at D24 using the EZ1 RT-qPCR assay8. Viral RNA in semen was detected by EZ1 RT-qPCR assay on D32 (Ct=18.47), 66 (Ct=29.71) and 110 (Ct=30.07) and was at or below limit of detection on D180, 244 and 361. Serum samples from these days tested negative.

Samples were tested in different antibody assays with approval from the U.S. Food and Drug Administration's Research Involving Human Subjects Committee (FDA-RIHSC) under exemption protocol #15-0B. Day 110 and 361 samples were analyzed before and after gamma irradiation in both GFPDL and SPR that demonstrated identical antibody reactivity.

Clinical Illness Severity Scoring

A modified sequential organ failure assessment (SOFA) score was used to quantify clinical illness severity daily. A score of 0 to +4 was applied for each of the respiratory, neurological, cardiovascular, hepatic, coagulation, and renal systems as per the validated assessment tool with higher scores indicative of greater organ dysfunction and illness severity (Ferreira et al., 2001). The following modifications to the scoring system were applied: 1) conversion tables estimating partial pressure of oxygen in blood from peripheral oxygen saturation, and estimating fraction of inspired oxygen from oxygen flow rate and delivery method were applied and 2) the Glasgow verbal score during intubation was estimated from the Glasgow eye and motor scores using a validated linear regression prediction model (Meredith et al., 1998).

Antibody Binding Kinetics of Post-ZEBOV Infection Human Sera to Recombinant ZEBOV Proteins by Surface Plasmon Resonance (SPR)

Steady-state equilibrium binding of post-ZEBOV infected human polyclonal serum was monitored at 25° C. using a ProteOn surface plasmon resonance (BioRad). The purified recombinant Makona proteins were captured to a Ni-NTA sensor chip with 200 resonance units (RU) in the test flow channels. The protein density on the chip was optimized such as to measure monovalent interactions independent of the antibody isotype. Serial dilutions (10-, 100-, 200-, 400- and 800-fold) of freshly prepared sera in BSA-PBST buffer (PBS pH 7.4 buffer with Tween-20 and BSA) were injected at a flow rate of 50 µl/min (120 sec contact duration) for association, and disassociation was performed over a 1200-second interval. Responses from the protein surface were corrected for the response from a mock surface and for responses from a buffer-only injection. SPR was performed with serially diluted serum of each individual time point in this study. Antibody isotype analysis for the ZEBOV protein bound antibodies in the polyclonal serum was performed using SPR. Total antibody binding and antibody isotype analysis were calculated with BioRad ProteOn manager software (version 3.1). All SPR experiments were performed twice and the researchers performing the assay were blinded to sample identity. In these optimized SPR conditions, the variation for each sample in duplicate SPR runs was <5%. The maximum resonance units (Max RU) data shown in the figures was the calculated RU signal for the undiluted serum sample.

Antibody off-rate constants, which describe the stability of the antigen-antibody complex, i.e. the fraction of complexes that decays per second, were determined directly from the human polyclonal sera sample interaction with recombinant purified ZEBOV proteins using SPR. To that end, serially diluted sera at 10-, 100-, 200-, 400- and 800-fold dilutions were analyzed to determine antibody off-rate constants, which describe the fraction of antigen-antibody complexes that decay per second in the dissociation phase, only for the sensorgrams with maximum RU in range of 10-100 RU (FIG. 10) and calculated using the BioRad ProteOn manager software for the heterogeneous sample model.

To confirm that the intact polyclonal IgG interacts with GP via monomeric interaction under the defined SPR conditions, binding kinetics of purified IgG from D361 sera and Fab fragments were compared. To that end, 10 µg/mL or 2 µg/mL each of purified IgG and purified Fab fractions of serum sample were analyzed for binding to Makona GP under optimized conditions in SPR as described above (FIG. 11).

Purification of IgG from Serum and Preparation of Fab Molecules

IgG was purified from serum using Protein A chromatography per manufacturer's instructions (Pierce/Thermofisher). Purified IgG was digested with Papain and the cleaved Fc was removed using Nab Protein A Plus Spin column kit (Thermofisher) and Fab fraction was collected as the flow-through fraction.

Gene Fragment Phage Display Library (GFPDL) Construction cDNA complementary to all genes of ZEBOV/Makona strain was chemically synthesized and used for cloning. A gIII display-based phage vector, fSK-9-3, was used where the desired polypeptide can be displayed on the surface of the phage as a gIII-fusion protein. Purified DNA containing each ZEBOV genes were digested separately with DNase I to obtain gene fragments of 50-1000 bp size range, then combined at equimolar amounts and used for GFPDL construction as described previously (Khurana et al. Nat Med. 22(12), 1439-1447, 2016). The phage libraries were constructed from the whole ZEBOV genome potentially display viral protein segments ranging in size from 15 to 350 amino acids, as fusion protein on the surface of bacteriophage (FIG. 14).

Affinity Selection of ZEBOV GFPDL Phages with Polyclonal Human Serum

Prior to panning of GFPDL with polyclonal serum antibodies, serum components that could non (Khurana et al. Nat Med. 22(12), 1439-1447, 2016)-specifically interact with phage proteins were removed by incubation with UV-killed M13K07 phage-coated Petri dishes. Equal volumes of each human serum were used for GFPDL panning. GFPDL affinity selection was carried out in-solution with anti-IgM, or protein A/G (IgG), or anti-IgA specific affinity resin as previously described (Khurana et al. Nat Med. 22(12), 1439-1447, 2016; Khurana et al. PLoS Med. 6(4), e1000049, 2009; Khurana et al. Sci Transl Med. 3(85), 85ra48, 2011). Briefly, the individual serum was incubated with the GFPDL and the specific resin, the unbound phages were removed by PBST (PBS containing 0.1% Tween-20) wash followed by washes with PBS. Bound phages were eluted by addition of 0.1 N Gly-HCl pH 2.2 and neutralized by adding 8 µl of 2 M Tris solution per 100 µl eluate. After panning, antibody-bound phage clones were amplified, the inserts were sequenced, and the sequences were aligned to the ZEBOV genome, to define the fine epitope specificity in this EVD survivors. The GFPDL affinity selection data was performed in duplicate (two independent experiments by research fellow in the lab, who was blinded to sample identity), and similar number of phage clones and epitope repertoire observed in both phage display analysis.

Binding of GP Antigenic Site Peptides to Post-ZEBOV Infection Sera by SPR

Steady-state equilibrium binding of GP antigenic site peptide with each time-point post-ZEBOV infection from this severely ill patient was monitored at 25° C. using a ProteOn surface plasmon resonance (Bio Rad). The biotinylated GP peptides were captured to an NLC sensor chip via avidin interaction with 500 resonance units (RU) in the test flow channels. Samples of 300 µl freshly prepared sera at 10-fold dilution in BSA-PBST buffer (PBS pH 7.4 buffer with Tween-20 and BSA) were injected at a flow rate of 50 µl/min (120 sec contact duration) for association, and dis-association was performed over a 600-second interval. Responses from the protein surface were corrected for the response from a mock surface and for responses from a buffer-only injection. The maximum resonance units (Max RU) data shown in the figures was the observed RU signal for each serum sample.

Adsorption of Polyclonal Human Post-Infection Sera on ZEBOV GFPDL Phages and Residual Reactivity to Makona-GP Prior to panning of GFPDL, 500 µl of 10-fold diluted serum antibodies from post-infection sample was adsorbed by incubation with ZEBOV GFPDL phage-coated Petri dishes. To ascertain the residual antibodies specificity, an ELISA was performed with wells coated with 200 ng/100 µl of recombinant Makona-GP. After blocking with PBST containing 2% milk, serial dilutions of human serum (with or without adsorption) in blocking solution were added to each well, incubated for 1 hr at RT, followed by addition of 5000-fold diluted HRP-conjugated goat anti-human IgA+IgG+IgM specific antibody and developed by 100 µl of OPD substrate solution. Absorbance was measured at 490 nm.

Peptide Fragment Conjugation to KLH Carrier Protein

The peptide conjugation to Maleimide Activated KLH was performed as described in the product manual of Imject® Maleimide Activated KLH (Product 77605, Thermo Scientific).

Rabbit Immunization Studies

Female New Zealand white rabbits were immunized thrice intra-muscularly at 21-days interval with 25 µg of KLH-conjugated peptides mixed with Emulsigen Adjuvant. Sera were collected before (pre-vaccination) and after 3$^{rd}$ vaccination and analyzed for binding antibodies in Surface Plasmon Resonance (SPR) and neutralization assay.

EBOV Microneutralization Assay

A 2-fold series of dilutions of the rabbit sera were prepared (starting dilution of 1:5). An equal volume of authentic ZEBOV/Kikwit was added to the diluted serum samples and incubated for 1 hr at 37° C. The virus was diluted to provide a MOI of 0.2 when added to the cells in triplicate. The dilutions of serum after mixing with virus were 1:10 and 2-fold thereafter. After the pre-incubation of virus and serum, this mixture was added to Vero cells and incubated for 1 hr at 37° C. Following this inoculation period, the virus/serum mixture was discarded, and fresh medium added to the cells. Following a 48 hr incubation at 37° C., cells were fixed in formalin and transferred to BSL2. Plates were blocked overnight at 4° C. in a PBS/FBS buffer. ZEBOV-infected cells were detected by MAb KZ52 followed by an anti-human IgG labelled with ALEXA FLUOR™ 488. Hoechst dye was added to stain nuclei. Serum dilutions that inhibit ZEBOV infection by 50% were determined and represent the IC50 values.

Mouse Immunization and Challenge Study 6-8 weeks old C57Bl/6 mice (n=10 per group) were immunized twice intramuscularly with 20 µg of GP 282-305, GP 343-368, GP 469-498, GP 520-547, and GP 617-645 KLH-conjugated peptides mixed with Emulsigen adjuvant, ZEBOV-GP VEEV replicon particle ($1\times10^6$ focus-forming units, sub-cutaneous inoculation), or with KLH or PBS as a negative control. An additional group received a mixture of GP peptides 282-305, 343-368, 469-498, 520-547, and 617-645 (20 µg total). Vaccinations were performed 29 days apart. 34 days following the second vaccination, mice were infected with 100 pfu of mouse-adapted Zaire ebolavirus/1976 strain (ma7EBOV) by the intraperitoneal route. Mice were monitored daily for clinical symptoms and daily cage weights were recorded.

ELISA 96 well polystyrene plates were coated with 50 µL of recombinant ZEBOV GP (amino acids 1-649, produced in HEK293 cells) at 10 µg/mL in PBS overnight at 4° C. Starting at a 1:100 dilution, serum samples were serially diluted 1:3 and applied to the ZEBOV GP-coated plate in 50 µL for 2 hr at ambient temperature. Serum samples were assayed in duplicate. Naïve serum samples were assayed the same as experimental samples. After three washes with PBS/0.02% Tween 20, ZEBOV GP-specific antibodies were detected with an anti-mouse IgG (H+L) HRP-conjugated antibody. After 1 hr, plates were washed as before and ABTS was added for 30 min. Absorbance was measured at 405 nm. End titer was determined by averaging the absorbance values of the naïve serum samples and adding three standard deviations. The end titer is reported as the last serum dilution that was above this cutoff.

Statistical Analyses

The statistical significances of group differences were determined using an Ordinary one-way ANOVA and Tukey's multiple comparisons method. p-values less than 0.05 were considered significant with a 95% confidence interval. Correlations were calculated with a Pearson method and P value for correlation was calculated by two-tailed test.

Example 2

A Differential Diagnostic Assay for Serodiagnosis of Ebola Virus Infections and Surveillance The 2014-15 Ebola virus (EBOV) disease (EVD) outbreak in West Africa and the ongoing outbreak in the Democratic Republic of Congo has highlighted the need for rapid serodiagnostic assays and efficient vaccine strategies due to potential recurrence of the outbreak. Efforts are ongoing towards development of simple and rapid diagnostic assays that can be conducted in resource-limited settings with minimal personnel training (Paweska et al., *Viruses* 11(8): 678, 2019). While such point-of-care and rapid PCR based diagnostic tests have been developed, these are only sensitive for detection of virus genomic material during active virus replication and suffer from several bottlenecks including limit of detection, impact of sample matrix and lower sensitivity of long-term EBOV persistence in immune-privileged sites (semen etc.). Serological tests such as enzyme-linked immunosorbent assay (ELISA) are used for a fast and high-throughput detection of antibody responses (IgG, IgM or IgA) associated with a filovirus infection (Paweska et al., *Viruses* 11(8): 678, 2019; Broadhurst et al., *Clin Microbiol Rev* 29: 773-793, 2016). Developing a simple ELISA for EVD surveillance by detecting IgM and IgG levels in serum samples offers many advantages. ELISAs are compatible with gamma irradiation that could be used to inactivate infectious viral components in the serum samples prior to handling and does not alter measurable levels of anti-EBOV IgG (Paweska et al., *Viruses* 11(8): 678, 2019; Broadhurst et al., *Clin Microbiol Rev* 29: 773-793, 2016). The assay can then be carried out in a BSL-2 condition without requirements for advanced infrastructure. Prior studies have shown the detection of IgG antibodies even up to day 749 in EVD survivors in the case of a 1995 Kikwit outbreak (Rowe et al., *J Infect Dis* 179(Suppl 1): S28-S35, 1999), which makes their detection useful for epidemiological studies in the case of infected and non-infected human samples. Traditional EBOV ELISA studies have used the whole virus or the viral envelope glycoprotein (GP), however, while large quantities of whole filoviral antigens can be produced, their preparation poses safety concerns to personnel involved, thus requiring BSL-4 facilities. Moreover, these ELISAs are more prone to false positive results, increased cross-reactivity and hence decreased specificity (Paweska et al., *Viruses* 11(8): 678, 2019; Groen et al., *Microbes Infect* 5: 379-385, 2003). Some ELISA have used recombinant EBOV-GP as the detecting antigen. However, the need for serological assays have been overlooked as a powerful tool for diagnosis and disease surveillance even in areas with limited resources.

With the licensures of two EBOV vaccines, one in the US (rVSV-ZEBOV) and one in Europe (Ad26.ZEBOV/MVA-BN-Filo), there have been efforts for large-scale vaccination in western Africa to curtail the occurrences and spread of EBOV outbreaks. Even though the vaccines have been shown to be effective in clinical trials, there have been observations of breakthrough EBOV infections following vaccination in western Africa. However, the scale of these breakthrough infections following vaccination is unknown due to lack to availability of true differential serological diagnostic tests as well as appropriate surveillance.

In this study, synthetic peptides representing antigenic sites identified using whole EBOV genome fragment phage display library (GFPDL) in EBOV-exposed individuals and an EVD survivor, were used as antigens for development of an ELISA-based serological test (Khurana et al., *Cell Host Microbe* 27: 262-276, 2020; Fuentes et al., *iScience* 23: 100920, 2020). Serum samples from EBOV infected patients, rVSV-EBOV or ChAd3/MVA vaccinated individuals, and control sera from unexposed adults were analyzed for the presence of IgG antibodies against EBOV peptides spanning NP, VP35, VP30, VP40 and VP24. Previous studies have used recombinant NP and VP35 antigens in ELISAs as these proteins were thought to be major determinants of immune responses following infection in humans and primates (Becker et al., *Med Microbiol Immunol* 181: 43-55, 1992; Elliott et al., *Arch Virol* 133: 423-436, 1993; Lucht et al., *J Virol Methods* 111: 21-28, 2003; Niikura et al., *J Clin Microbiol* 39: 3267-3271, 2001). However, high antibody titers against VP40, VP30 and VP24 were observed up to 2 years post-EBOV exposure (Khurana et al., *Cell Host Microbe* 27: 262-276, 2020). Therefore, this study evaluates the serodiagnosis potential of these individual peptides and different combinations of peptides in an ELISA format with a diverse set of human serum samples for differential serodiagnosis of true EBOV infection.

Methods

Study Serum Samples

A panel of 33 EBOV-infected, 33 rVSV-EBOV vaccinated, 2 ChAd3/MVA vaccinated, and 10 influenza H1N1 infected and 3 healthy control adults' samples were tested in an ELISA. The clinical plasma samples from EBOV survivors, the ChAd3/MVA prime-boost vaccinated group and negative control serum samples were obtained from NIB SC as part of a "WHO collaborative study to assess the suitability of an interim standard for antibodies to Ebola virus" (Wilkinson et al., Vaccine 35: 1347-1352, 2017; Fuentes et al., *iScience* 23: 100920, 2020). Briefly, plasma obtained from convalescent patients recovered from Ebola virus disease were negative for Ebola virus RNA and other blood viral markers. The PCR-negative plasmas were solvent-detergent-extracted using a method validated at NIBSC. Serum samples from additional EBOV survivors were also obtained. rVSV-ZEBOV vaccinated serum samples were obtained from NIAID, NIH clinical trial (Khurana et al., *Nat Med* 22: 1439-1447, 2016). Serum from influenza H1N1 infected individuals during the 2009 pandemic were included as a control (Verma et al., *J Virol* 86: 5515-5522, 2012).

Enzyme-Linked Immunosorbent Assay (ELISA)

Nine biotinylated peptides selected from whole-genome GFPDL analysis of post-EBOV infected human serum/plasma were chemically synthesized. The 9 biotinylated peptides and a panel of 4 mixtures of peptides were evaluated by ELISA. The chosen peptides and combinations were as follows: NP 1-41 (1); NP 453-514 (2); VP35 742-815 (3); VP35-895-934 (4); VP35 930-965 (5); VP40 1084-1133 (6); VP40 1313-1387 (7); VP30 2088-2114 (8); VP24 2560-2612 (9) and peptide mixtures Mix-1 (VP35 930-965+VP40 1313-1387); Mix-2 (VP35 930-965+VP40 1313-1387+VP30 2088-2114); Mix-3 (VP35 930-965+VP40 1084-1133+VP40 1313-1387+VP24 2560-2612); and Mix-4 (VP35 930-965+VP40 1084-1133+VP40 1313-1387+VP30 2088-2114+VP24 2560-2612). 96-well ELISA plates (Immunolon 2HB, Fisher) were coated overnight at 4° C. with 200 ng streptavidin (NEB) in 100 μL PBS in each well. After washing the plates three times with PBST (0.05% Tween-20) each of the 13 biotinylated peptides/peptide mixtures were added in 100 μL PBS and allowed to bind the streptavidin-coated wells for 1 hour at RT. One column in the 96-well plate was coated with EBOV-GP as a control. The plates were then washed three times with PBST and blocked for 2 hours at RT with 5% BSA-PBST. Serially diluted serum samples in 2% BSA-PBST were added to the plates and incubated for 1 hour at RT. After washing the plates, 100 μL of HRP-conjugated anti-human IgG-Fc antibodies were added and incubated for 1 hour at RT. The plates were washed again, and the bound antibodies were developed with O-phenylenediamine substrate solution (Thermofisher). After stopping the reaction with 3.3M H2504, the plates were read at 492 nm. Samples were considered seropositive if the absorbance values exceeded twice the mock serum control values for each peptide and were above a cut-off absorbance value of 0.05. The OD values to a mock antigen was subtracted from those of the positive antigen to normalize the values for each sample. All statistical analyses were done using one-way ANOVA with a Tukey post-hoc analysis using GraphPad Prism (v. 9.0) with * denoting p<0.05,  p<0.01, * p<0.001, **** p<0.0001.

Results

Figure 30:
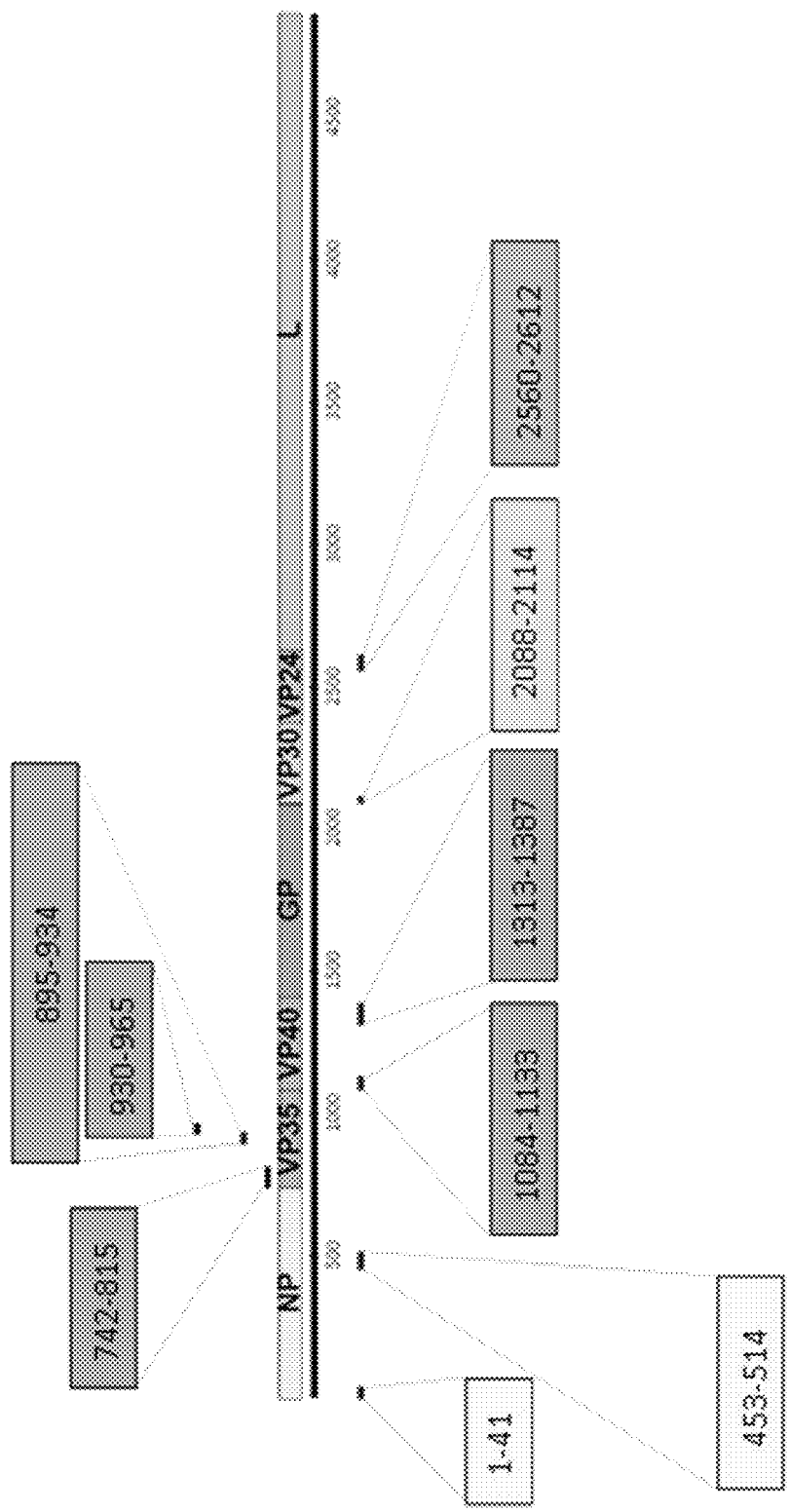
FIG. 30. Selected peptides used for development of Ebola-Serodetect. A whole proteome map of EBOV showing the NP, VP35, VP40, GP, VP30, VP24 and L proteins. Selected epitopes from NP, VP35, VP40, GP, VP30 and VP24 identified using the EBOV-GFPDL approach are indicated with their amino acid positions. These epitopes were used as biotinylated peptides in the ELISA experiments described in Example 2.

Currently, most EBOV serodiagnostic tests employ GP antigen as the target, however, since most EBOV vaccines currently licensed or under development induce antibodies that target GP, they will therefore react in an EBOV-GP serodiagnostic test, resulting in a false-positive result. This will lead to the phenomenon of vaccine-induced seropositivity (VISP), which would confound the interpretation of EBOV GP-based or whole virus-based serodiagnostic assays. Therefore, study disclosed herein focused on differential antigenic sites in proteins other than GP that were identified in EBOV-infected patients but not in uninfected controls using EBOV GFPDL analysis to determine potential serodiagnostic candidates (FIG. 30). Nine EBOV peptides representing immunodominant antigenic sites up to 74 amino acid residues long were chemically synthesized and evaluated for antibody binding with serum from 33 EBOV-infected human samples as well as 48 controls (including 10 influenza H1N1-infected adults (ages 18-45 years, collected in 2009) and 33 rVSV-ZEBOV and 2 ChAd3-MVA vaccinated adults (ages 18-45 years)).

Reactivity of EBOV-infected serum samples were tested and compared with controls and vaccinated groups including control serum samples, influenza infected controls, rVSV-ZEBOV vaccinated and ChAd3/MVA vaccinated serum samples (FIG. 31) against the selected peptides (FIG. 30) from the whole EBOV genome (NP, VP35, VP40, VP30 and VP24 proteins). The antibody binding of post-EBOV infection samples to most peptides evolved with similar trends; however, the absolute total binding of antibodies against different antigenic sites varied with EBOV-infected versus controls.

Figure 31:
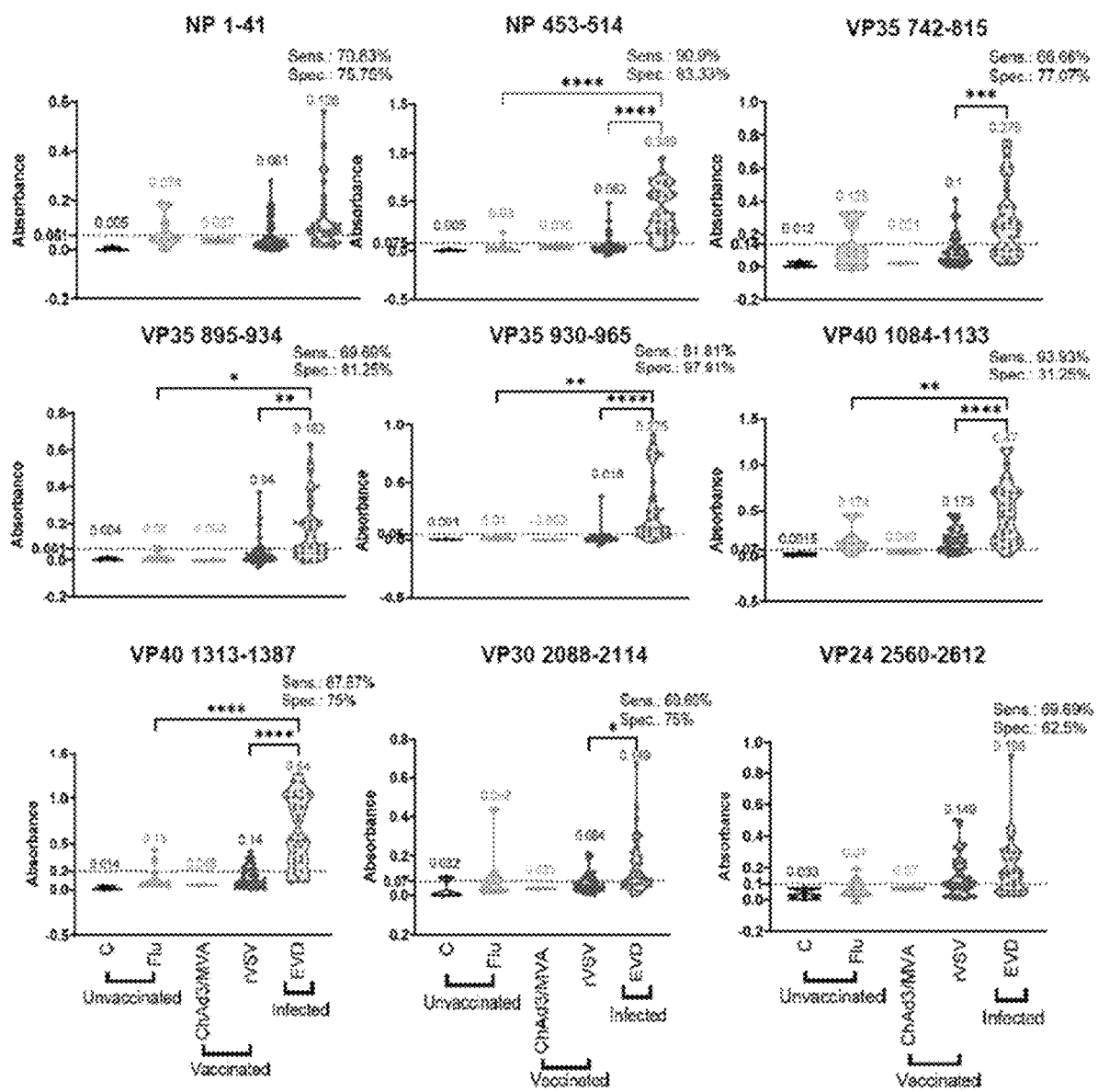
FIG. 31. Reactivity of human serum samples to individual peptides in ELISA. Serum IgG absorbance values at a 1:100 serum dilution were determined for each sample group. Control (C, N=3), H1N1-infected (Flu, N=10), ChAd3/MVA-vaccinated (ChAd3/MVA, N=2), rVSV-ZEBOV vaccinated (rVSV, N=33) and EBOV-infected sera (EVD, N=33) were plotted based on the reactivity to each peptide. Sensitivity and specificity were calculated for each peptide as a percentage based on a calculated cut-off value for each peptide, indicated as a dotted line. Mean values for each group are indicated.

Absorbance values at a serum dilution of 1:100 were plotted for each of the 9 peptides (FIG. 31). Percent sensitivity and specificity (true seropositive and true seronegative, respectively) values were calculated for each peptide by determining a suitable cut-off value for each peptide. Most peptides demonstrated sensitivity and specificity values above 60%, with the exception of VP40 (1084-1133) whose specificity value was 31%. Individual peptides derived from NP, VP35, VP40, VP30 and VP24 showed IgG binding with a highest sensitivity of 94% (VP40 1084-1133) and a highest specificity of 98% (VP35 930-965). Except for the non-specific reactivity of rVSV-ZEBOV-vaccinated samples to a few peptides, minimal binding of IgG antibodies was observed against these selected peptides with control serum samples, ChAd3/MVA vaccinated samples or H1N1-infected samples in ELISA. Serum samples from EBOV survivors showed a statistically significant higher reactivity to NP 453-514 (p<0.0001), VP35 (p<0.001), VP40 (p<0.0001) and VP30 (p<0.05) peptides compared with VSV-ZEBOV-vaccinated samples (FIG. 31).

Figure 32:
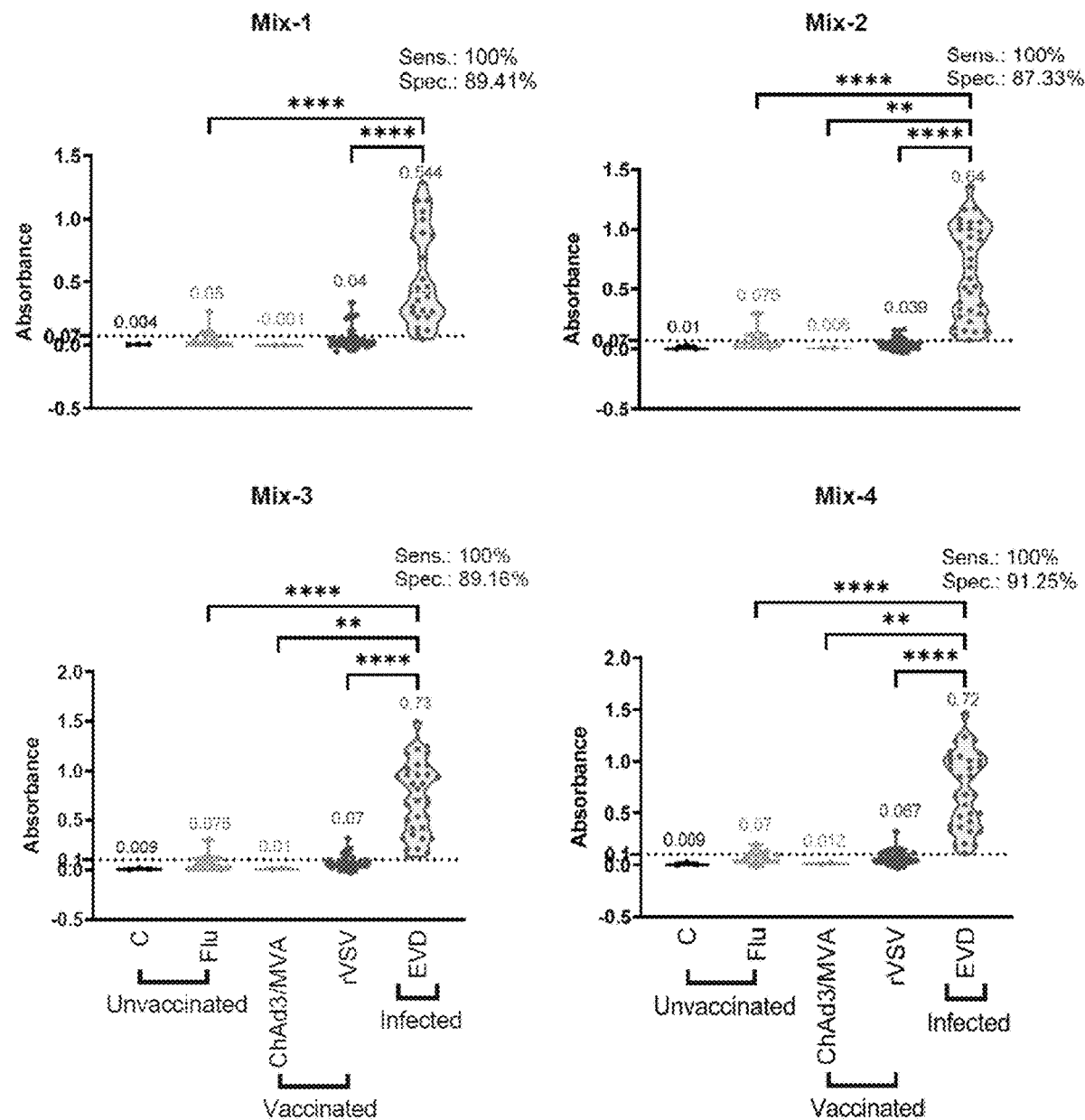
FIG. 32. Immune response of human serum samples to combinatorial mixtures of peptides. Serum IgG absorbance values at a 1:100 serum dilution were determined for each sample group. Control (C, N=3), H1N1-infected (Flu, N=10), ChAd3/MVA-vaccinated (ChAd3/MVA, N=2), rVSV-ZEBOV vaccinated (rVSV, N=33) and EBOV-infected sera (EVD, N=33) were plotted based on the reactivity to different mixtures of peptides. The peptide mixtures tested were VP35 930-965+VP40 1313-1387 (Mix-1); VP35 930-965+VP40 1313-1387+VP30 2088-2114 (Mix-2); VP35 930-965+VP40 1084-1133+VP40 1313-1387+VP24 2560-2612 (Mix-3); and VP35 930-965+VP40 1084-1133+VP40 1313-1387+VP30 2088-2114+VP24 2560-2612 (Mix-4). Sensitivity and specificity were calculated for each peptide as a percentage based on a calculated cut-off value for each peptide, indicated as a dotted line. Mean values for each group are indicated.
Figure 34:
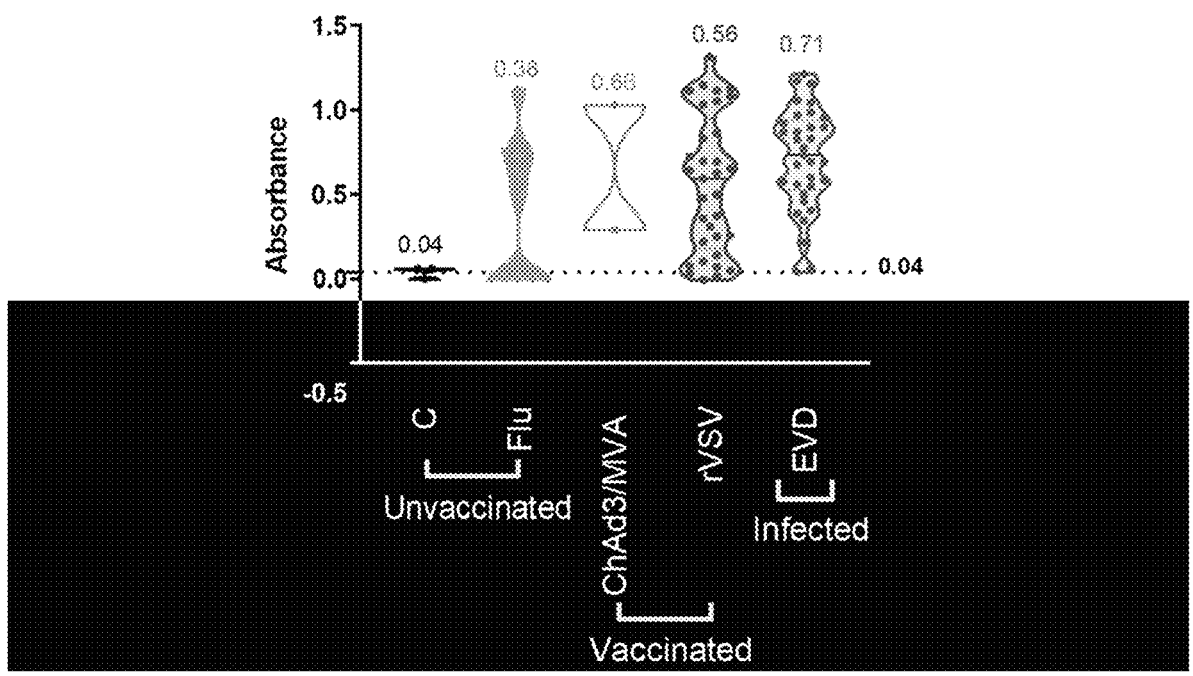
FIG. 34. ELISA reactivity to GP protein. Serum IgG absorbance values at a 1:100 serum dilution were determined for each sample group. Control (C), H1N1-infected (Flu), ChAd3/MVA-vaccinated (ChAd3/MVA), rVSV-ZEBOV-vaccinated (rRSV) and EBOV-infected (EVD) sera were plotted based on the reactivity to EBOV GP protein. Mean values for each group are indicated.

To enhance the sensitivity and specificity of the serodiagnostic assay, following individual peptide analysis, combinations of the individual peptides were tested with same panel of samples. Serum/plasma samples from EBOV survivors showed a significantly (p<0.0001) high reactivity to all mixtures of peptides tested (Mix 1-4) compared to rVSV-ZEBOV-vaccinated samples and H1N1-infected samples, which showed negligible non-specific reactivity below the determined cut-off value. While the sensitivity of the assay was above 65% for all individual peptides (FIG. 31) tested with the EBOV infected serum samples, sensitivity of 100% was seen in the case of mixtures of peptides (FIG. 32). Furthermore, Mix-1 and Mix-2 containing the VP35, VP40 and VP30 peptides were sufficient to detect all EBOV infected samples (100% sensitivity) with >80% specificity and achieving statistical significance when compared to vaccinated (p<0.01) or control samples (p<0.0001). This can possibly be due to the cumulative recognition of specific multiple epitopes on various EBOV proteins by the IgG antibodies in the EBOV-infected serum samples contributing to the greater sensitivity for detection of true EBOV infections. The EBOV GP exhibited a 100% reactivity with the ChAd3/MVA-vaccinated and rVSV-ZEBOV-vaccinated samples as well as EBOV-infected samples as expected, while four H1N1-infected samples showed a non-specific reactivity to the GP (FIG. 34).

Figure 33A:
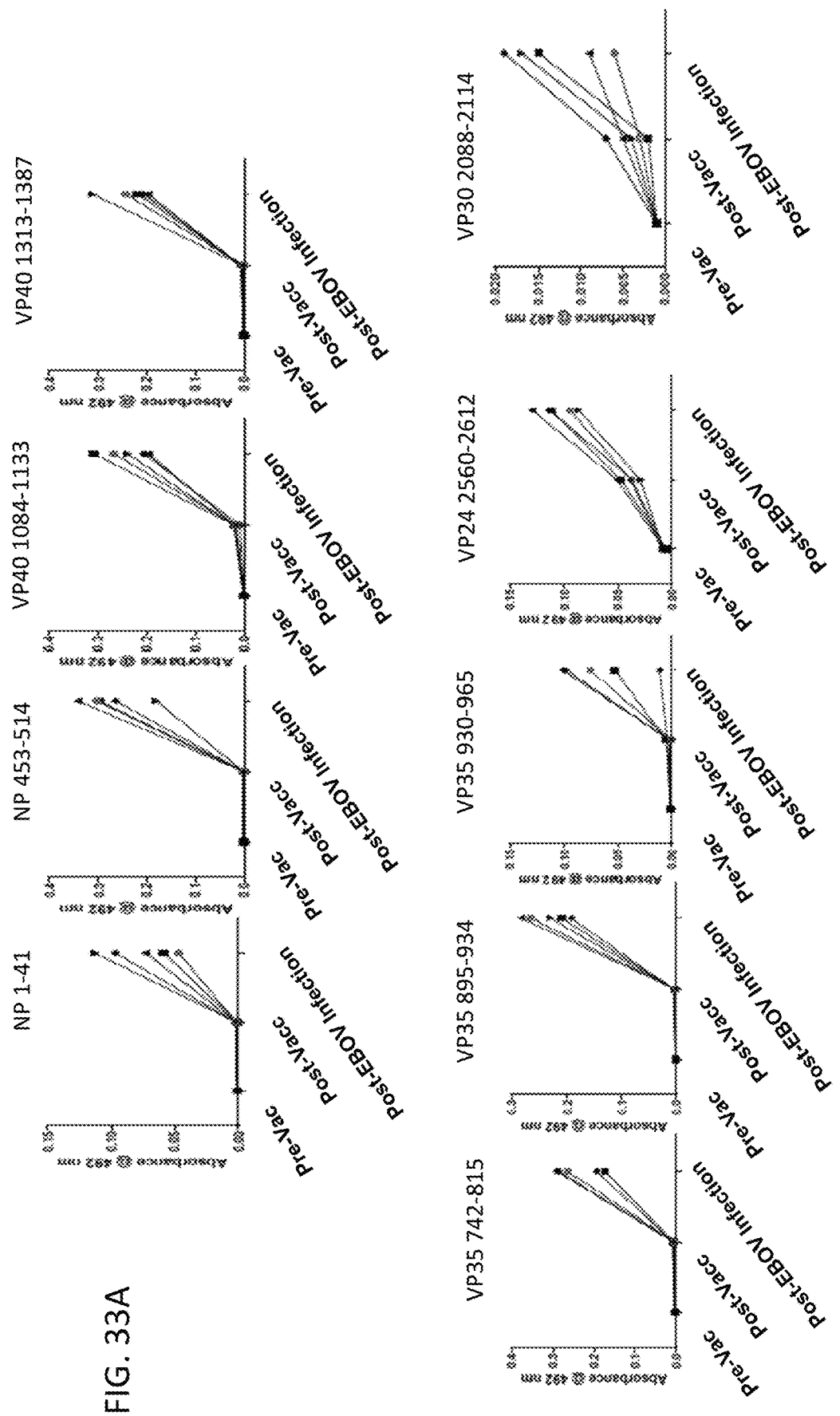
FIGS. 33A-33B. Immune response of vaccinated and EBOV-infected NHP serum samples to individual and combinations of peptides in ELISA. Serum IgG absorbance values at a 1:100 serum dilution were determined for each NHPs sample. Pre-vaccinated (pre-vacc), post-rVSV-ZEBOV vaccinated NHP sera (post-vacc), and post-EBOV infection NHP convalescent sera (post-EBOV infection) were plotted for each individual peptide (FIG. 33A) and mixtures of peptides (FIG. 33B), including VP35 930-965+VP40 1313-1387+VP30 2088-2114 (Mix-2); VP35 930-965+VP40 1084-1133+VP40 1313-1387+VP24 2560-2612 (Mix-3); and VP35 930-965+VP40 1084-1133+VP40 1313-1387+VP30 2088-2114+VP24 2560-2612 (Mix-4).
Figure 33B:
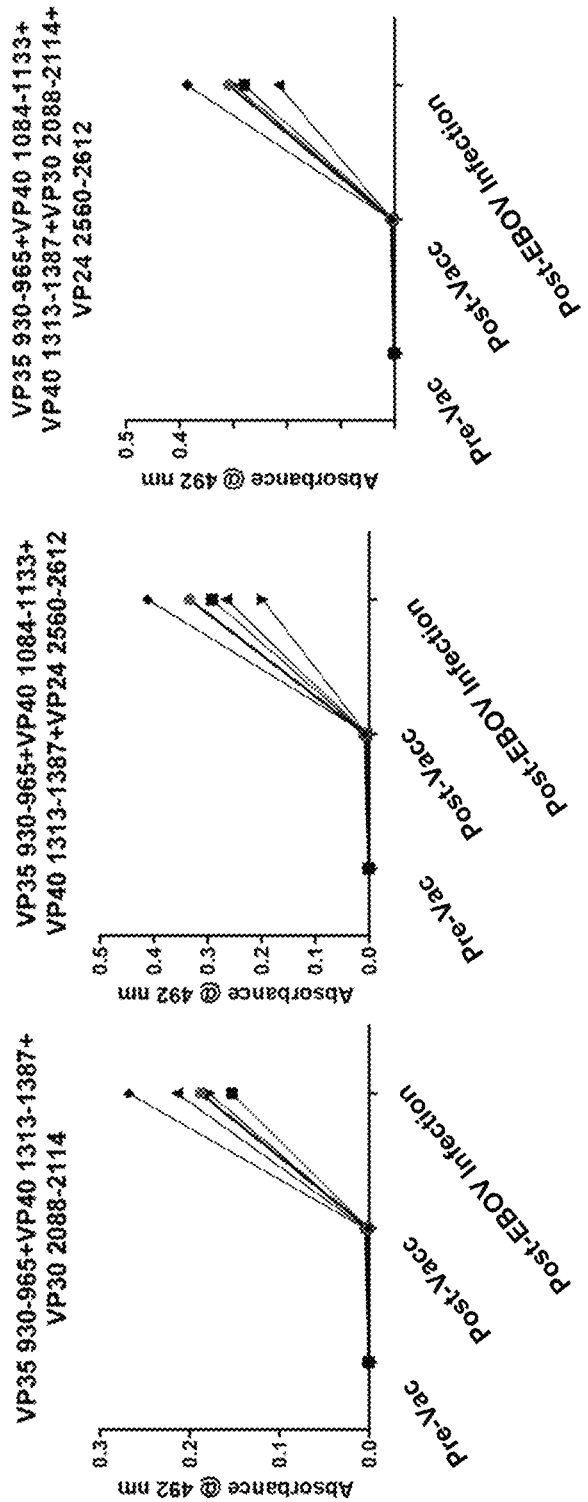

To further evaluate the true serodiagnosis of EBOV infection following vaccination, serum reactivity of 5 NHPs prior to vaccination, 1-month after two doses of rVSV-ZEBOV vaccination and convalescent samples collected approximately 9 to 12-months after EBOV challenge were evaluated. While a higher absorbance value was observed in the case of the convalescent samples against all peptides, the vaccinated samples showed a varied reactivity pattern to the peptides tested (FIG. 33A). Negligible reactivity of the vaccinated samples was observed with all peptides tested except for weak reactivity of VP24 2560-2612 and VP30 2088-2114 peptides. However, peptide combination Mix-2, -3 and Mix-4 peptides demonstrated highly sensitive and specific reactivity only to post-EBOV infection samples, but not with post-rVSV-ZEBOV vaccinated samples (FIG. 33B). The IgG reactivity of the EBOV-infected convalescent serum samples to peptide mixture derived from various EBOV proteins remained high, showing an EBOV infection-specific additive reactivity with a mixture of peptides rather than the individual peptides.

Taken together, these data show an EBOV-infection mounts an IgG response that recognizes a wide variety of EBOV epitopes other than GP, that can serve as potential serodiagnostic targets. The ChAd3/MVA and rVSV-ZEBOV-vaccinated serum samples did not show reactivity to these peptides while the samples from EBOV survivors showed a statistically significant high reactivity to various individual peptides. The sensitivity and specificity of this ELISA was further improved by testing various combinations of VP35, VP40 and VP30 derived peptides as a mixture, where the EBOV-infected samples showed a statistically significant higher response compared with all controls and ChAd3/MVA and rVSV-ZEBOV-vaccinated samples. Additional data demonstrates that the peptides disclosed herein can be used in combination with full-length VP35, VP40 and/or NP to improve serodiagnosis. Thus, these results show that these peptide mixtures of Ebola virus excluding GP can be used as effective serodiagnostic tools and aid in differentiating host immune response in a natural EBOV infection vs. VISP induced by rVSV-ZEBOV or Ad/MVA vaccination, thereby eliminating false positives and diagnosing the breakthrough EBOV infections in the face of large scale vaccinations. In contrast to some non-specific reactivity observed with EBOV-GP in the case of a few H1N1-infected samples, individual peptides or mixtures of peptides identified by GFPDL as targets showed a higher specificity in the case of EBOV-infected samples compared to either vaccinated or unrelated control samples. Hence this allows for the potential use of these peptides and peptide mixtures as serodiagnostic targets for detection of natural EBOV-infection in a population of vaccinated and non-vaccinated individuals using a simple ELISA-based approach that can be quickly done with minimal infrastructure in the case of an outbreak.

It will be apparent that the precise details of the methods or compositions described may be varied or modified without departing from the spirit of the described embodiments. We claim all such modifications and variations that fall within the scope and spirit of the claims below.

SEQUENCE LISTING

```
<160> NUMBER OF SEQ ID NOS: 124

<210> SEQ ID NO 1
<211> LENGTH: 21
<212> TYPE: PRT
<213> ORGANISM: Ebola virus

<400> SEQUENCE: 1

Met Asp Ser Arg Pro Gln Lys Val Trp Met Thr Pro Ser Leu Thr Glu
1               5                   10                  15

Ser Asp Met Asp Tyr
            20

<210> SEQ ID NO 2
<211> LENGTH: 41
<212> TYPE: PRT
<213> ORGANISM: Ebola virus

<400> SEQUENCE: 2

Met Asp Ser Arg Pro Gln Lys Val Trp Met Thr Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile
        35                  40

<210> SEQ ID NO 3
<211> LENGTH: 62
<212> TYPE: PRT
<213> ORGANISM: Ebola virus

<400> SEQUENCE: 3

Thr Ile Pro Asp Val Val Val Asp Pro Asp Asp Gly Gly Tyr Gly Glu
1               5                   10                  15

Tyr Gln Ser Tyr Ser Glu Asn Gly Met Ser Ala Pro Asp Asp Leu Val
            20                  25                  30

Leu Phe Asp Leu Asp Glu Asp Asp Glu Asp Thr Lys Pro Val Pro Asn
        35                  40                  45

Arg Ser Thr Lys Gly Gly Gln Gln Lys Asn Ser Gln Lys Gly
    50                  55                  60

<210> SEQ ID NO 4
<211> LENGTH: 74
<212> TYPE: PRT
<213> ORGANISM: Ebola virus

<400> SEQUENCE: 4

Met Thr Thr Arg Thr Lys Gly Arg Gly His Thr Val Ala Thr Thr Gln
1               5                   10                  15
```

Asn Asp Arg Met Pro Gly Pro Glu Leu Ser Gly Trp Ile Ser Glu Gln
            20                  25                  30

Leu Met Thr Gly Arg Ile Pro Val Asn Asp Ile Phe Cys Asp Ile Glu
            35                  40                  45

Asn Asn Pro Gly Leu Cys Tyr Ala Ser Gln Met Gln Gln Thr Lys Pro
50                  55                  60

Asn Pro Lys Met Arg Asn Ser Gln Thr Gln
65                  70

<210> SEQ ID NO 5
<211> LENGTH: 40
<212> TYPE: PRT
<213> ORGANISM: Ebola virus

<400> SEQUENCE: 5

Ala Thr Ala Ala Ala Thr Glu Ala Tyr Trp Ala Glu His Gly Gln Pro
1               5                   10                  15

Pro Pro Gly Pro Ser Leu Tyr Glu Gly Ser Ala Ile Arg Gly Lys Ile
            20                  25                  30

Glu Ser Arg Asp Glu Thr Val Pro
            35                  40

<210> SEQ ID NO 6
<211> LENGTH: 36
<212> TYPE: PRT
<213> ORGANISM: Ebola virus

<400> SEQUENCE: 6

Asp Glu Thr Val Pro Gln Ser Val Arg Glu Ala Phe Asn Asn Leu Asp
1               5                   10                  15

Ser Thr Thr Ser Leu Thr Glu Glu Asn Phe Gly Lys Pro Asp Ile Ser
            20                  25                  30

Ala Lys Asp Leu
            35

<210> SEQ ID NO 7
<211> LENGTH: 33
<212> TYPE: PRT
<213> ORGANISM: Ebola virus

<400> SEQUENCE: 7

Met Arg Arg Val Ile Leu Pro Thr Ala Pro Pro Glu Tyr Met Glu Ala
1               5                   10                  15

Ile Tyr Pro Ala Arg Ser Asn Ser Thr Ile Ala Arg Gly Gly Asn Ser
            20                  25                  30

Asn

<210> SEQ ID NO 8
<211> LENGTH: 50
<212> TYPE: PRT
<213> ORGANISM: Ebola virus

<400> SEQUENCE: 8

Met Arg Arg Val Ile Leu Pro Thr Ala Pro Pro Glu Tyr Met Glu Ala
1               5                   10                  15

Ile Tyr Pro Ala Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
            35                  40                  45

Asn Pro
    50

<210> SEQ ID NO 9
<211> LENGTH: 75
<212> TYPE: PRT
<213> ORGANISM: Ebola virus

<400> SEQUENCE: 9

Asp Leu Thr Ser Pro Glu Lys Ile Gln Ala Ile Met Thr Ser Leu Gln
1               5                   10                  15

Asp Phe Lys Ile Val Pro Ile Asp Pro Thr Lys Asn Ile Met Gly Ile
            20                  25                  30

Glu Val Pro Glu Thr Leu Val His Lys Leu Thr Gly Lys Lys Val Thr
        35                  40                  45

Ser Lys Asn Gly Gln Pro Ile Ile Pro Val Leu Leu Pro Lys Tyr Ile
    50                  55                  60

Gly Leu Asp Pro Val Ala Pro Gly Asp Leu Thr
65                  70                  75

<210> SEQ ID NO 10
<211> LENGTH: 47
<212> TYPE: PRT
<213> ORGANISM: Ebola virus

<400> SEQUENCE: 10

Lys Ile Val Pro Ile Asp Pro Thr Lys Asn Ile Met Gly Ile Glu Val
1               5                   10                  15

Pro Glu Thr Leu Val His Lys Leu Thr Gly Lys Lys Val Thr Ser Lys
            20                  25                  30

Asn Gly Gln Pro Ile Ile Pro Val Leu Leu Pro Lys Tyr Ile Gly
        35                  40                  45

<210> SEQ ID NO 11
<211> LENGTH: 47
<212> TYPE: PRT
<213> ORGANISM: Ebola virus

<400> SEQUENCE: 11

Lys Lys Gly Asn Ser Ala Asp Leu Thr Ser Pro Glu Lys Ile Gln Ala
1               5                   10                  15

Ile Met Thr Ser Leu Gln Asp Phe Lys Ile Val Pro Ile Asp Pro Thr
            20                  25                  30

Lys Asn Ile Met Gly Ile Glu Val Pro Glu Thr Leu Val His Lys
        35                  40                  45

<210> SEQ ID NO 12
<211> LENGTH: 27
<212> TYPE: PRT
<213> ORGANISM: Ebola virus

<400> SEQUENCE: 12

Met Glu Ala Ser Tyr Glu Arg Gly Arg Pro Arg Ala Ala Arg Gln His
1               5                   10                  15

Ser Arg Asp Gly His Asp His His Val Arg Ala
            20                  25

<210> SEQ ID NO 13
<211> LENGTH: 55
<212> TYPE: PRT
<213> ORGANISM: Ebola virus

<400> SEQUENCE: 13

Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Ser Arg
            20                  25                  30

Glu Asn Tyr Arg Gly Glu Tyr Arg Gln Ser Arg Ser Ala Ser Gln Val
        35                  40                  45

Arg Val Pro Thr Val Phe His
    50                  55

<210> SEQ ID NO 14
<211> LENGTH: 53
<212> TYPE: PRT
<213> ORGANISM: Ebola virus

<400> SEQUENCE: 14

Thr Gln Asn His Thr Ile Ile Ile Thr Arg Thr Asn Met Gly Phe Leu
1               5                   10                  15

Val Glu Leu Gln Glu Pro Asp Lys Ser Ala Met Asn Arg Lys Lys Pro
            20                  25                  30

Gly Pro Ala Lys Phe Ser Leu Leu His Glu Ser Thr Leu Lys Ala Phe
        35                  40                  45

Thr Gln Gly Ser Ser
    50

<210> SEQ ID NO 15
<211> LENGTH: 739
<212> TYPE: PRT
<213> ORGANISM: Ebola virus

<400> SEQUENCE: 15

Met Asp Ser Arg Pro Gln Lys Val Trp Met Thr Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Cys Asp
            100                 105                 110

Gly Val Lys Arg Leu Glu Glu Leu Pro Ala Val Ser Ser Gly Arg
        115                 120                 125

Asn Ile Lys Arg Thr Leu Ala Ala Met Pro Glu Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

```
Ser Val Gly His Met Met Val Ile Phe Arg Leu Met Arg Thr Asn Phe
            195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
        355                 360                 365

Asp Asp Gln Glu Lys Lys Ile Leu Met Asn Phe His Gln Lys Lys Asn
    370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
                405                 410                 415

Thr Ser Gly His Tyr Asp Asp Asp Asp Ile Pro Phe Pro Gly Pro
            420                 425                 430

Ile Asn Asp Asp Asp Asn Pro Gly His Gln Asp Asp Pro Thr Asp
        435                 440                 445

Ser Gln Asp Thr Thr Ile Pro Asp Val Val Val Asp Pro Asp Asp Gly
    450                 455                 460

Gly Tyr Gly Glu Tyr Gln Ser Tyr Ser Glu Asn Gly Met Ser Ala Pro
465                 470                 475                 480

Asp Asp Leu Val Leu Phe Asp Leu Asp Glu Asp Glu Asp Thr Lys
                485                 490                 495

Pro Val Pro Asn Arg Ser Thr Lys Gly Gly Gln Gln Lys Asn Ser Gln
            500                 505                 510

Lys Gly Gln His Thr Glu Gly Arg Gln Thr Gln Ser Thr Pro Thr Gln
        515                 520                 525

Asn Val Thr Gly Pro Arg Arg Thr Ile His His Ala Ser Ala Pro Leu
    530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Leu Glu Ser Asp Asp Glu Glu Gln
            580                 585                 590

Asp Arg Asp Gly Thr Ser Asn Arg Thr Pro Thr Val Ala Pro Pro Ala
        595                 600                 605

Pro Val Tyr Arg Asp His Ser Glu Lys Lys Glu Leu Pro Gln Asp Glu
```

```
            610                 615                 620
Gln Gln Asp Gln Asp His Ile Gln Glu Ala Arg Asn Gln Asp Ser Asp
625                 630                 635                 640

Asn Thr Gln Pro Glu His Ser Phe Glu Glu Met Tyr Arg His Ile Leu
                645                 650                 655

Arg Ser Gln Gly Pro Phe Asp Ala Val Leu Tyr Tyr His Met Met Lys
                660                 665                 670

Asp Glu Pro Val Val Phe Ser Thr Ser Asp Gly Lys Glu Tyr Thr Tyr
                675                 680                 685

Pro Asp Ser Leu Glu Glu Glu Tyr Pro Pro Trp Leu Thr Glu Lys Glu
                690                 695                 700

Ala Met Asn Asp Glu Asn Arg Phe Val Thr Leu Asp Gly Gln Gln Phe
705                 710                 715                 720

Tyr Trp Pro Val Met Asn His Arg Asn Lys Phe Met Ala Ile Leu Gln
                725                 730                 735

His His Gln

<210> SEQ ID NO 16
<211> LENGTH: 340
<212> TYPE: PRT
<213> ORGANISM: Ebola virus

<400> SEQUENCE: 16

Met Thr Thr Arg Thr Lys Gly Arg Gly His Thr Val Ala Thr Thr Gln
1               5                   10                  15

Asn Asp Arg Met Pro Gly Pro Glu Leu Ser Gly Trp Ile Ser Glu Gln
                20                  25                  30

Leu Met Thr Gly Arg Ile Pro Val Asn Asp Ile Phe Cys Asp Ile Glu
                35                  40                  45

Asn Asn Pro Gly Leu Cys Tyr Ala Ser Gln Met Gln Gln Thr Lys Pro
            50                  55                  60

Asn Pro Lys Met Arg Asn Ser Gln Thr Gln Thr Asp Pro Ile Cys Asn
65              70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
                100                 105                 110

Ser Leu Glu Asn Gly Leu Lys Pro Val Tyr Asp Met Ala Lys Thr Ile
                115                 120                 125

Ser Ser Leu Asn Arg Val Cys Ala Glu Met Val Ala Lys Tyr Asp Leu
                130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
                180                 185                 190

Pro Gln Ser Val Arg Glu Ala Phe Asn Asn Leu Asp Ser Thr Thr Ser
                195                 200                 205

Leu Thr Glu Glu Asn Phe Gly Lys Pro Asp Ile Ser Ala Lys Asp Leu
                210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
```

-continued

```
                    245                 250                 255
Asp Ile Ile His Ala Glu Phe Gln Ala Ser Leu Ala Glu Gly Asp Ser
                260                 265                 270

Pro Gln Cys Ala Leu Ile Gln Ile Thr Lys Arg Val Pro Ile Phe Gln
            275                 280                 285

Asp Ala Ala Pro Pro Val Ile His Ile Arg Ser Arg Gly Asp Ile Pro
        290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 17
<211> LENGTH: 326
<212> TYPE: PRT
<213> ORGANISM: Ebola virus

<400> SEQUENCE: 17

Met Arg Arg Val Ile Leu Pro Thr Ala Pro Pro Glu Tyr Met Glu Ala
1               5                   10                  15

Ile Tyr Pro Ala Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270
```

-continued

```
Gly Lys Lys Val Thr Ser Lys Asn Gly Gln Pro Ile Pro Val Leu
            275                 280                 285

Leu Pro Lys Tyr Ile Gly Leu Asp Pro Val Ala Pro Gly Asp Leu Thr
290                 295                 300

Met Val Ile Thr Gln Asp Cys Asp Thr Cys His Ser Pro Ala Ser Leu
305                 310                 315                 320

Pro Ala Val Val Glu Lys
                325

<210> SEQ ID NO 18
<211> LENGTH: 674
<212> TYPE: PRT
<213> ORGANISM: Ebola virus

<400> SEQUENCE: 18

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320
```

Gln Ser Pro Ala Arg Thr Ser Ser Asp Pro Glu Thr Asn Thr Thr Asn
            325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
            355                 360                 365

Ala Thr Ile Ser Thr Ser Pro Gln Pro Pro Thr Thr Lys Thr Gly Pro
            370                 375                 380

Asp Asn Ser Thr His Asn Thr Pro Val Tyr Lys Leu Asp Ile Ser Glu
385                 390                 395                 400

Ala Thr Gln Val Gly Gln His Arg Arg Ala Asp Asn Asp Ser Thr
            405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
            435                 440                 445

Thr Thr Ser Pro Gln Asn Tyr Ser Glu Thr Ala Gly Asn Asn Asn Thr
            450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
            530                 535                 540

Glu Gly Leu Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Arg Ile Cys Lys Phe
            660                 665                 670

Val Phe

<210> SEQ ID NO 19
<211> LENGTH: 288
<212> TYPE: PRT
<213> ORGANISM: Ebola virus

<400> SEQUENCE: 19

Met Glu Ala Ser Tyr Glu Arg Gly Arg Pro Arg Ala Ala Arg Gln His
1               5                   10                  15

```
Ser Arg Asp Gly His Asp His Val Arg Ala Arg Ser Ser Ser Arg
            20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
 50                  55                  60

Pro Pro Ala Pro Lys Asp Ile Cys Pro Thr Leu Lys Lys Gly Phe Leu
 65                  70                  75                  80

Cys Asp Ser Ser Phe Cys Lys Lys Asp His Gln Leu Glu Ser Leu Thr
                 85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
            115                 120                 125

Pro Thr Ala Asp Asp Phe Gln Gln Glu Glu Gly Pro Lys Ile Thr Leu
130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
            195                 200                 205

Glu Val Tyr Gln Arg Leu His Ser Asp Lys Gly Gly Ser Phe Glu Ala
            210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
            275                 280                 285

<210> SEQ ID NO 20
<211> LENGTH: 251
<212> TYPE: PRT
<213> ORGANISM: Ebola virus

<400> SEQUENCE: 20

Met Ala Lys Ala Thr Gly Arg Tyr Asn Leu Ile Ser Pro Lys Lys Asp
 1               5                  10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
            35                  40                  45

Val Thr His Lys Gly Met Ala Leu Leu His Arg Leu Lys Thr Asn Asp
 50                  55                  60

Phe Ala Pro Ala Trp Ser Met Thr Arg Asn Leu Phe Pro His Leu Phe
 65                  70                  75                  80

Gln Asn Pro Asn Ser Thr Ile Glu Ser Pro Leu Trp Ala Leu Arg Val
                 85                  90                  95

Ile Leu Ala Ala Gly Ile Gln Asp Gln Leu Ile Asp Gln Ser Leu Ile
```

```
                100                 105                 110
Glu Pro Leu Ala Gly Ala Leu Gly Leu Ile Ser Asp Trp Leu Leu Thr
                115                 120                 125

Thr Asn Thr Asn His Phe Asn Met Arg Thr Gln Arg Val Lys Glu Gln
            130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Thr Arg
                180                 185                 190

Thr Asn Met Gly Phe Leu Val Glu Leu Gln Glu Pro Asp Lys Ser Ala
            195                 200                 205

Met Asn Arg Lys Lys Pro Gly Pro Ala Lys Phe Ser Leu Leu His Glu
                210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250

<210> SEQ ID NO 21
<211> LENGTH: 2234
<212> TYPE: PRT
<213> ORGANISM: Ebola virus
<220> FEATURE:
<221> NAME/KEY: misc_feature
<222> LOCATION: (2213)..(2213)
<223> OTHER INFORMATION: Xaa can be any naturally occurring amino acid
<220> FEATURE:
<221> NAME/KEY: misc_feature
<222> LOCATION: (2228)..(2228)
<223> OTHER INFORMATION: Xaa can be any naturally occurring amino acid

<400> SEQUENCE: 21

Met Ala Thr Gln His Thr Gln Tyr Pro Asp Ala Arg Leu Ser Ser Pro
1               5                   10                  15

Ile Val Leu Asp Gln Cys Asp Leu Val Thr Arg Ala Cys Gly Leu Tyr
                20                  25                  30

Ser Ser Tyr Ser Leu Asn Pro Gln Leu Arg Asn Cys Lys Leu Pro Lys
            35                  40                  45

His Ile Tyr Arg Leu Lys Tyr Asp Val Thr Val Thr Lys Phe Leu Ser
        50                  55                  60

Asp Val Pro Val Ala Thr Leu Pro Ile Asp Phe Ile Val Pro Val Leu
65                  70                  75                  80

Leu Lys Ala Leu Ser Gly Asn Gly Phe Cys Pro Val Glu Pro Arg Cys
                85                  90                  95

Gln Gln Phe Leu Asp Glu Ile Ile Lys Tyr Thr Met Gln Asp Ala Leu
                100                 105                 110

Phe Leu Lys Tyr Tyr Leu Lys Asn Val Gly Ala Gln Glu Asp Cys Val
                115                 120                 125

Asp Glu His Phe Gln Glu Lys Ile Leu Ser Ser Ile Gln Gly Asn Glu
            130                 135                 140

Phe Leu His Gln Met Phe Phe Trp Tyr Asp Leu Ala Ile Leu Thr Arg
145                 150                 155                 160

Arg Gly Arg Leu Asn Arg Gly Asn Ser Arg Ser Thr Trp Phe Val His
                165                 170                 175

Asp Asp Leu Ile Asp Ile Leu Gly Tyr Gly Asp Tyr Val Phe Trp Lys
```

```
            180                 185                 190
Ile Pro Ile Ser Met Leu Pro Leu Asn Thr Gln Gly Ile Pro His Ala
            195                 200                 205
Ala Met Asp Trp Tyr Gln Ala Ser Val Phe Lys Glu Ala Val Gln Gly
            210                 215                 220
His Thr His Ile Val Ser Val Ser Thr Ala Asp Val Leu Ile Met Cys
225                 230                 235                 240
Lys Asp Leu Ile Thr Cys Arg Phe Asn Thr Thr Leu Ile Ser Lys Ile
                245                 250                 255
Ala Glu Ile Glu Asp Pro Val Cys Ser Asp Tyr Pro Asn Phe Lys Ile
            260                 265                 270
Val Ser Met Leu Tyr Gln Ser Gly Asp Tyr Leu Leu Ser Ile Leu Gly
            275                 280                 285
Ser Asp Gly Tyr Lys Ile Ile Lys Phe Leu Glu Pro Leu Cys Leu Ala
            290                 295                 300
Lys Ile Gln Leu Cys Ser Lys Tyr Thr Glu Arg Lys Gly Arg Phe Leu
305                 310                 315                 320
Thr Gln Met His Leu Ala Val Asn His Thr Leu Glu Glu Ile Thr Glu
                325                 330                 335
Met Arg Ala Leu Lys Pro Ser Gln Ala Gln Lys Ile Arg Glu Phe His
            340                 345                 350
Arg Thr Leu Ile Arg Leu Glu Met Thr Pro Gln Gln Leu Cys Glu Leu
            355                 360                 365
Phe Ser Ile Gln Lys His Trp Gly His Pro Val Leu His Ser Glu Thr
            370                 375                 380
Ala Ile Gln Lys Val Lys Lys His Ala Thr Val Leu Lys Ala Leu Arg
385                 390                 395                 400
Pro Ile Val Ile Phe Glu Thr Tyr Cys Val Phe Lys Tyr Ser Ile Ala
                405                 410                 415
Lys His Tyr Phe Asp Ser Gln Gly Ser Trp Tyr Ser Val Thr Ser Asp
                420                 425                 430
Arg Asn Leu Thr Pro Gly Leu Asn Ser Tyr Ile Lys Arg Asn Gln Phe
            435                 440                 445
Pro Pro Leu Pro Met Ile Lys Glu Leu Leu Trp Glu Phe Tyr His Leu
            450                 455                 460
Asp His Pro Pro Leu Phe Ser Thr Lys Ile Ile Ser Asp Leu Ser Ile
465                 470                 475                 480
Phe Ile Lys Asp Arg Ala Thr Ala Val Glu Arg Thr Cys Trp Asp Ala
                485                 490                 495
Val Phe Glu Pro Asn Val Leu Gly Tyr Asn Pro Pro His Lys Phe Ser
            500                 505                 510
Thr Lys Arg Val Pro Glu Gln Phe Leu Glu Gln Glu Asn Phe Ser Ile
            515                 520                 525
Glu Asn Val Leu Ser Tyr Ala Gln Lys Leu Glu Tyr Leu Leu Pro Gln
            530                 535                 540
Tyr Arg Asn Phe Ser Phe Ser Leu Lys Glu Lys Glu Leu Asn Val Gly
545                 550                 555                 560
Arg Thr Phe Gly Lys Leu Pro Tyr Pro Thr Arg Asn Val Gln Thr Leu
                565                 570                 575
Cys Glu Ala Leu Leu Ala Asp Gly Leu Ala Lys Ala Phe Pro Ser Asn
                580                 585                 590
Met Met Val Val Thr Glu Arg Glu Gln Lys Glu Ser Leu Leu His Gln
            595                 600                 605
```

```
Ala Ser Trp His His Thr Ser Asp Asp Phe Gly Glu His Ala Thr Val
        610                 615                 620
Arg Gly Ser Ser Phe Val Thr Asp Leu Glu Lys Tyr Asn Leu Ala Phe
625                 630                 635                 640
Arg Tyr Glu Phe Thr Ala Pro Phe Ile Glu Tyr Cys Asn Arg Cys Tyr
                645                 650                 655
Gly Val Lys Asn Val Phe Asn Trp Met His Tyr Thr Ile Pro Gln Cys
                660                 665                 670
Tyr Met His Val Ser Asp Tyr Tyr Asn Pro Pro His Asn Leu Thr Leu
        675                 680                 685
Glu Asn Arg Asp Asn Pro Pro Glu Gly Pro Ser Ser Tyr Arg Gly His
690                 695                 700
Met Gly Gly Ile Glu Gly Leu Gln Gln Lys Leu Trp Thr Ser Ile Ser
705                 710                 715                 720
Cys Ala Gln Ile Ser Leu Val Glu Ile Lys Thr Gly Phe Lys Leu Arg
                725                 730                 735
Ser Ala Val Met Gly Asp Asn Gln Cys Ile Thr Val Leu Ser Val Phe
                740                 745                 750
Pro Leu Glu Thr Asp Ala Asp Glu Gln Glu Gln Ser Ala Glu Asp Asn
        755                 760                 765
Ala Ala Arg Val Ala Ala Ser Leu Ala Lys Val Thr Ser Ala Cys Gly
770                 775                 780
Ile Phe Leu Lys Pro Asp Glu Thr Phe Val His Ser Gly Phe Ile Tyr
785                 790                 795                 800
Phe Gly Lys Lys Gln Tyr Leu Asn Gly Val Gln Leu Pro Gln Ser Leu
                805                 810                 815
Lys Thr Ala Thr Arg Met Ala Pro Leu Ser Asp Ala Ile Phe Asp Asp
                820                 825                 830
Leu Gln Gly Thr Leu Ala Ser Ile Gly Thr Ala Phe Glu Arg Ser Ile
        835                 840                 845
Ser Glu Thr Arg His Ile Phe Pro Cys Arg Ile Thr Ala Ala Phe His
850                 855                 860
Thr Phe Phe Ser Val Arg Ile Leu Gln Tyr His His Leu Gly Phe Asn
865                 870                 875                 880
Lys Gly Phe Asp Leu Gly Gln Leu Thr Leu Gly Lys Pro Leu Asp Phe
                885                 890                 895
Gly Thr Ile Ser Leu Ala Leu Ala Val Pro Gln Val Leu Gly Gly Leu
                900                 905                 910
Ser Phe Leu Asn Pro Glu Lys Cys Phe Tyr Arg Asn Leu Gly Asp Pro
        915                 920                 925
Val Thr Ser Gly Leu Phe Gln Leu Lys Thr Tyr Leu Arg Met Ile Glu
930                 935                 940
Met Asp Asp Leu Phe Leu Pro Leu Ile Ala Lys Asn Pro Gly Asn Cys
945                 950                 955                 960
Thr Ala Ile Asp Phe Val Leu Asn Pro Ser Gly Leu Asn Val Pro Gly
                965                 970                 975
Ser Gln Asp Leu Thr Ser Phe Leu Arg Gln Ile Val Arg Arg Thr Ile
        980                 985                 990
Thr Leu Ser Ala Lys Asn Lys Leu  Ile Asn Thr Leu Phe  His Ala Ser
            995                 1000                1005
Ala Asp  Phe Glu Asp Glu Met  Val Cys Lys Trp Leu  Leu Ser Ser
    1010                1015                1020
```

```
Thr Pro Val Met Ser Arg Phe Ala Ala Asp Ile Phe Ser Arg Thr
1025                1030                1035

Pro Ser Gly Lys Arg Leu Gln Ile Leu Gly Tyr Leu Glu Gly Thr
1040                1045                1050

Arg Thr Leu Leu Ala Ser Lys Ile Ile Asn Asn Asn Thr Glu Thr
1055                1060                1065

Pro Val Leu Asp Arg Leu Arg Lys Ile Thr Leu Gln Arg Trp Ser
1070                1075                1080

Leu Trp Phe Ser Tyr Leu Asp His Cys Asp Asn Ile Leu Ala Glu
1085                1090                1095

Ala Leu Thr Gln Ile Thr Cys Thr Val Asp Leu Ala Gln Ile Leu
1100                1105                1110

Arg Glu Tyr Ser Trp Ala His Ile Leu Glu Gly Arg Pro Leu Ile
1115                1120                1125

Gly Ala Thr Leu Pro Cys Met Ile Glu Gln Phe Lys Val Phe Trp
1130                1135                1140

Leu Lys Pro Tyr Glu Gln Cys Pro Gln Cys Ser Asn Ala Lys Gln
1145                1150                1155

Pro Gly Gly Lys Pro Phe Val Ser Val Ala Val Lys Lys His Ile
1160                1165                1170

Val Ser Ala Trp Pro Asn Ala Ser Arg Ile Ser Trp Thr Ile Gly
1175                1180                1185

Asp Gly Ile Pro Tyr Ile Gly Ser Arg Thr Glu Asp Lys Ile Gly
1190                1195                1200

Gln Pro Ala Ile Lys Pro Lys Cys Pro Ser Ala Ala Leu Arg Glu
1205                1210                1215

Ala Ile Glu Leu Ala Ser Arg Leu Thr Trp Val Thr Gln Gly Ser
1220                1225                1230

Ser Asn Ser Asp Leu Leu Ile Lys Pro Phe Leu Glu Ala Arg Val
1235                1240                1245

Asn Leu Ser Val Gln Glu Ile Leu Gln Met Thr Pro Ser His Tyr
1250                1255                1260

Ser Gly Asn Ile Val His Arg Tyr Asn Asp Gln Tyr Ser Pro His
1265                1270                1275

Ser Phe Met Ala Asn Arg Met Ser Asn Ser Ala Thr Arg Leu Ile
1280                1285                1290

Val Ser Thr Asn Thr Leu Gly Glu Phe Ser Gly Gly Gly Gln Ser
1295                1300                1305

Ala Arg Asp Ser Asn Ile Ile Phe Gln Asn Val Ile Asn Tyr Ala
1310                1315                1320

Val Ala Leu Phe Asp Ile Lys Phe Arg Asn Thr Glu Ala Thr Asp
1325                1330                1335

Ile Gln Tyr Asn Arg Ala His Leu His Leu Thr Lys Cys Cys Thr
1340                1345                1350

Arg Glu Val Pro Ala Gln Tyr Leu Thr Tyr Thr Ser Thr Leu Asp
1355                1360                1365

Leu Asp Leu Thr Arg Tyr Arg Glu Asn Glu Leu Ile Tyr Asp Ser
1370                1375                1380

Asn Pro Leu Lys Gly Gly Leu Asn Cys Asn Ile Ser Phe Asp Asn
1385                1390                1395

Pro Phe Phe Gln Gly Lys Arg Leu Asn Ile Ile Glu Asp Asp Leu
1400                1405                1410

Ile Arg Leu Pro His Leu Ser Gly Trp Glu Leu Ala Lys Thr Ile
```

```
                1415                1420                1425
Met Gln Ser Ile Ile Ser Asp Ser Asn Asn Ser Ser Thr Asp Pro
                1430                1435                1440
Ile Ser Ser Gly Glu Thr Arg Ser Phe Thr Thr His Phe Leu Thr
                1445                1450                1455
Tyr Pro Lys Ile Gly Leu Leu Tyr Ser Phe Gly Ala Phe Val Ser
                1460                1465                1470
Tyr Tyr Leu Gly Asn Thr Ile Leu Arg Thr Lys Lys Leu Thr Leu
                1475                1480                1485
Asp Asn Phe Leu Tyr Tyr Leu Thr Thr Gln Ile His Asn Leu Pro
                1490                1495                1500
His Arg Ser Leu Arg Ile Leu Lys Pro Thr Phe Lys His Ala Ser
                1505                1510                1515
Val Met Ser Arg Leu Met Ser Ile Asp Pro His Phe Ser Ile Tyr
                1520                1525                1530
Ile Gly Gly Ala Ala Gly Asp Arg Gly Leu Ser Asp Ala Ala Arg
                1535                1540                1545
Leu Phe Leu Arg Thr Ser Ile Ser Ser Phe Leu Thr Phe Val Lys
                1550                1555                1560
Glu Trp Ile Ile Asn Arg Gly Thr Ile Val Pro Leu Trp Ile Val
                1565                1570                1575
Tyr Pro Leu Glu Gly Gln Asn Pro Thr Pro Val Asn Asn Phe Leu
                1580                1585                1590
Tyr Gln Ile Val Glu Leu Leu Val His Asp Ser Ser Arg Gln Gln
                1595                1600                1605
Ala Phe Lys Thr Thr Ile Ser Asp His Val His Pro His Asp Asn
                1610                1615                1620
Leu Val Tyr Thr Cys Lys Ser Thr Ala Ser Asn Phe Phe His Ala
                1625                1630                1635
Ser Leu Ala Tyr Trp Arg Ser Arg His Arg Asn Ser Asn Arg Lys
                1640                1645                1650
Tyr Leu Ala Arg Asp Ser Ser Thr Gly Ser Ser Thr Asn Asn Ser
                1655                1660                1665
Asp Gly His Ile Glu Arg Ser Gln Glu Gln Thr Thr Arg Asp Pro
                1670                1675                1680
His Asp Gly Thr Glu Arg Asn Leu Val Leu Gln Met Ser His Glu
                1685                1690                1695
Ile Lys Arg Thr Thr Ile Pro Gln Glu Asn Thr His Gln Gly Pro
                1700                1705                1710
Ser Phe Gln Ser Phe Leu Ser Asp Ser Ala Cys Gly Thr Ala Asn
                1715                1720                1725
Pro Lys Leu Asn Phe Asp Arg Ser Arg His Asn Val Lys Phe Gln
                1730                1735                1740
Asp His Asn Ser Ala Ser Lys Arg Glu Gly His Gln Ile Ile Ser
                1745                1750                1755
His Arg Leu Val Leu Pro Phe Phe Thr Leu Ser Gln Gly Thr Arg
                1760                1765                1770
Gln Leu Thr Ser Ser Asn Glu Ser Gln Thr Gln Asp Glu Ile Ser
                1775                1780                1785
Lys Tyr Leu Arg Gln Leu Arg Ser Val Ile Asp Thr Thr Val Tyr
                1790                1795                1800
Cys Arg Phe Thr Gly Ile Val Ser Ser Met His Tyr Lys Leu Asp
                1805                1810                1815
```

```
Glu Val Leu Trp Glu Ile Glu Ser Phe Lys Ser Ala Val Thr Leu
    1820            1825                1830

Ala Glu Gly Glu Gly Ala Gly Ala Leu Leu Ile Gln Lys Tyr
    1835            1840                1845

Gln Val Lys Thr Leu Phe Phe Asn Thr Leu Ala Thr Glu Ser Ser
    1850            1855                1860

Ile Glu Ser Glu Ile Val Ser Gly Met Thr Thr Pro Arg Met Leu
    1865            1870                1875

Leu Pro Val Met Ser Lys Phe His Asn Asp Gln Ile Glu Ile Ile
    1880            1885                1890

Leu Asn Asn Ser Ala Ser Gln Ile Thr Asp Ile Thr Asn Pro Thr
    1895            1900                1905

Trp Phe Lys Asp Gln Arg Ala Arg Leu Pro Lys Gln Val Glu Val
    1910            1915                1920

Ile Thr Met Asp Ala Glu Thr Thr Glu Asn Ile Asn Arg Ser Lys
    1925            1930                1935

Leu Tyr Glu Ala Val Tyr Lys Leu Ile Leu His His Ile Asp Pro
    1940            1945                1950

Ser Val Leu Lys Ala Val Val Leu Lys Val Phe Leu Ser Asp Thr
    1955            1960                1965

Glu Gly Met Leu Trp Leu Asn Asp Asn Leu Ala Pro Phe Phe Ala
    1970            1975                1980

Thr Gly Tyr Leu Ile Lys Pro Ile Thr Ser Ser Ala Arg Ser Ser
    1985            1990                1995

Glu Trp Tyr Leu Cys Leu Thr Asn Phe Leu Ser Thr Thr Arg Lys
    2000            2005                2010

Met Pro His Gln Asn His Leu Ser Cys Lys Gln Val Ile Leu Thr
    2015            2020                2025

Ala Leu Gln Leu Gln Ile Gln Arg Ser Pro Tyr Trp Leu Ser His
    2030            2035                2040

Leu Thr Gln Tyr Ala Asp Cys Glu Leu His Leu Ser Tyr Ile Arg
    2045            2050                2055

Leu Gly Phe Pro Ser Leu Glu Lys Val Leu Tyr His Arg Tyr Asn
    2060            2065                2070

Leu Val Asp Ser Lys Arg Gly Pro Leu Val Ser Ile Thr Gln His
    2075            2080                2085

Leu Ala His Leu Arg Ala Glu Ile Arg Glu Leu Thr Asn Asp Tyr
    2090            2095                2100

Asn Gln Gln Arg Gln Ser Arg Thr Gln Thr Tyr His Phe Ile Arg
    2105            2110                2115

Thr Ala Lys Gly Arg Ile Thr Lys Leu Val Asn Asp Tyr Leu Lys
    2120            2125                2130

Phe Phe Leu Ile Val Gln Ala Leu Lys His Asn Gly Thr Trp Gln
    2135            2140                2145

Ala Glu Phe Lys Lys Leu Pro Glu Leu Ile Ser Val Cys Asn Arg
    2150            2155                2160

Phe Tyr His Ile Arg Asp Cys Asn Cys Glu Glu Arg Phe Leu Val
    2165            2170                2175

Gln Thr Leu Tyr Leu His Arg Met Gln Asp Ser Glu Val Lys Leu
    2180            2185                2190

Ile Glu Arg Leu Thr Gly Leu Leu Ser Leu Phe Pro Asp Gly Leu
    2195            2200                2205
```

```
Tyr Arg Phe Asp Xaa Ile Thr Val His Ser Ile Leu Ile Leu Ala
    2210            2215                2220

Lys Val Gly Tyr Xaa His Thr Asp Tyr Lys Lys
    2225            2230
```

<210> SEQ ID NO 22
<211> LENGTH: 101
<212> TYPE: PRT
<213> ORGANISM: Ebola virus

<400> SEQUENCE: 22

```
Met Asp Ser Arg Pro Gln Lys Val Trp Met Thr Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly
            100
```

<210> SEQ ID NO 23
<211> LENGTH: 140
<212> TYPE: PRT
<213> ORGANISM: Ebola virus

<400> SEQUENCE: 23

```
Met Asp Ser Arg Pro Gln Lys Val Trp Met Thr Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Cys Asp
            100                 105                 110

Gly Val Lys Arg Leu Glu Glu Leu Leu Pro Ala Val Ser Ser Gly Arg
        115                 120                 125

Asn Ile Lys Arg Thr Leu Ala Ala Met Pro Glu Glu
        130                 135                 140
```

<210> SEQ ID NO 24
<211> LENGTH: 196
<212> TYPE: PRT
<213> ORGANISM: Ebola virus

<400> SEQUENCE: 24

```
Met Asp Ser Arg Pro Gln Lys Val Trp Met Thr Pro Ser Leu Thr Glu
```

```
1               5                   10                  15
Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
            50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Cys Asp
                100                 105                 110

Gly Val Lys Arg Leu Glu Glu Leu Leu Pro Ala Val Ser Ser Gly Arg
                115                 120                 125

Asn Ile Lys Arg Thr Leu Ala Ala Met Pro Glu Glu Glu Thr Thr Glu
                130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
                180                 185                 190

Ser Val Gly His
        195

<210> SEQ ID NO 25
<211> LENGTH: 79
<212> TYPE: PRT
<213> ORGANISM: Ebola virus

<400> SEQUENCE: 25

Ala Asp Ser Phe Leu Leu Met Leu Cys Leu His His Ala Tyr Gln Gly
1               5                   10                  15

Asp Tyr Lys Leu Phe Leu Glu Ser Gly Ala Val Lys Tyr Leu Glu Gly
            20                  25                  30

His Gly Phe Arg Phe Glu Val Lys Lys Cys Asp Gly Val Lys Arg Leu
            35                  40                  45

Glu Glu Leu Leu Pro Ala Val Ser Ser Gly Arg Asn Ile Lys Arg Thr
        50                  55                  60

Leu Ala Ala Met Pro Glu Glu Glu Thr Thr Glu Ala Asn Ala Gly
65                  70                  75

<210> SEQ ID NO 26
<211> LENGTH: 255
<212> TYPE: PRT
<213> ORGANISM: Ebola virus

<400> SEQUENCE: 26

Tyr Gln Gly Asp Tyr Lys Leu Phe Leu Glu Ser Gly Ala Val Lys Tyr
1               5                   10                  15

Leu Glu Gly His Gly Phe Arg Phe Glu Val Lys Lys Cys Asp Gly Val
            20                  25                  30

Lys Arg Leu Glu Glu Leu Leu Pro Ala Val Ser Ser Gly Arg Asn Ile
            35                  40                  45

Lys Arg Thr Leu Ala Ala Met Pro Glu Glu Glu Thr Thr Glu Ala Asn
```

```
                 50                  55                  60
Ala Gly Gln Phe Leu Ser Phe Ala Ser Leu Phe Leu Pro Lys Leu Val
 65                  70                  75                  80

Val Gly Glu Lys Ala Cys Leu Glu Lys Val Gln Arg Gln Ile Gln Val
                 85                  90                  95

His Ala Glu Gln Gly Leu Ile Gln Tyr Pro Thr Ala Trp Gln Ser Val
                100                 105                 110

Gly His Met Met Val Ile Phe Arg Leu Met Arg Thr Asn Phe Leu Ile
                115                 120                 125

Lys Phe Leu Leu Ile His Gln Gly Met His Met Val Ala Gly His Asp
                130                 135                 140

Ala Asn Asp Ala Val Ile Ser Asn Ser Val Ala Gln Ala Arg Phe Ser
145                 150                 155                 160

Gly Leu Leu Ile Val Lys Thr Val Leu Asp His Ile Leu Gln Lys Thr
                165                 170                 175

Glu Arg Gly Val Arg Leu His Pro Leu Ala Arg Thr Ala Lys Val Lys
                180                 185                 190

Asn Glu Val Asn Ser Phe Lys Ala Ala Leu Ser Ser Leu Ala Lys His
                195                 200                 205

Gly Glu Tyr Ala Pro Phe Ala Arg Leu Leu Asn Leu Ser Gly Val Asn
                210                 215                 220

Asn Leu Glu His Gly Leu Phe Pro Gln Leu Ser Ala Ile Ala Leu Gly
225                 230                 235                 240

Val Ala Thr Ala His Gly Ser Thr Leu Ala Gly Val Asn Val Gly
                245                 250                 255

<210> SEQ ID NO 27
<211> LENGTH: 37
<212> TYPE: PRT
<213> ORGANISM: Ebola virus

<400> SEQUENCE: 27

Asp Gly Val Lys Arg Leu Glu Glu Leu Leu Pro Ala Val Ser Ser Gly
 1               5                  10                  15

Arg Asn Ile Lys Arg Thr Leu Ala Ala Met Pro Glu Glu Glu Thr Thr
                20                  25                  30

Glu Ala Asn Ala Gly
         35

<210> SEQ ID NO 28
<211> LENGTH: 65
<212> TYPE: PRT
<213> ORGANISM: Ebola virus

<400> SEQUENCE: 28

Leu His Pro Leu Ala Arg Thr Ala Lys Val Lys Asn Glu Val Asn Ser
 1               5                  10                  15

Phe Lys Ala Ala Leu Ser Ser Leu Ala Lys His Gly Glu Tyr Ala Pro
                20                  25                  30

Phe Ala Arg Leu Leu Asn Leu Ser Gly Val Asn Asn Leu Glu His Gly
         35                  40                  45

Leu Phe Pro Gln Leu Ser Ala Ile Ala Leu Gly Val Ala Thr Ala His
         50                  55                  60

Gly
 65
```

```
<210> SEQ ID NO 29
<211> LENGTH: 80
<212> TYPE: PRT
<213> ORGANISM: Ebola virus

<400> SEQUENCE: 29
```

Asn Asn Leu Glu His Gly Leu Phe Pro Gln Leu Ser Ala Ile Ala Leu
1               5                   10                  15

Gly Val Ala Thr Ala His Gly Ser Thr Leu Ala Gly Val Asn Val Gly
                20                  25                  30

Glu Gln Tyr Gln Gln Leu Arg Glu Ala Ala Thr Glu Ala Glu Lys Gln
            35                  40                  45

Leu Gln Gln Tyr Ala Glu Ser Arg Glu Leu Asp His Leu Gly Leu Asp
        50                  55                  60

Asp Gln Glu Lys Lys Ile Leu Met Asn Phe His Gln Lys Lys Asn Glu
65                  70                  75                  80

```
<210> SEQ ID NO 30
<211> LENGTH: 175
<212> TYPE: PRT
<213> ORGANISM: Ebola virus

<400> SEQUENCE: 30
```

Thr Glu Ala Glu Lys Gln Leu Gln Gln Tyr Ala Glu Ser Arg Glu Leu
1               5                   10                  15

Asp His Leu Gly Leu Asp Asp Gln Glu Lys Lys Ile Leu Met Asn Phe
                20                  25                  30

His Gln Lys Lys Asn Glu Ile Ser Phe Gln Gln Thr Asn Ala Met Val
            35                  40                  45

Thr Leu Arg Lys Glu Arg Leu Ala Lys Leu Thr Glu Ala Ile Thr Ala
        50                  55                  60

Ala Ser Leu Pro Lys Thr Ser Gly His Tyr Asp Asp Asp Asp Asp Ile
65                  70                  75                  80

Pro Phe Pro Gly Pro Ile Asn Asp Asp Asp Asn Pro Gly His Gln Asp
                85                  90                  95

Asp Asp Pro Thr Asp Ser Gln Asp Thr Thr Ile Pro Asp Val Val Val
            100                 105                 110

Asp Pro Asp Asp Gly Gly Tyr Gly Glu Tyr Gln Ser Tyr Ser Glu Asn
        115                 120                 125

Gly Met Ser Ala Pro Asp Asp Leu Val Leu Phe Asp Leu Asp Glu Asp
    130                 135                 140

Asp Glu Asp Thr Lys Pro Val Pro Asn Arg Ser Thr Lys Gly Gly Gln
145                 150                 155                 160

Gln Lys Asn Ser Gln Lys Gly Gln His Thr Glu Gly Arg Gln Thr
                165                 170                 175

```
<210> SEQ ID NO 31
<211> LENGTH: 54
<212> TYPE: PRT
<213> ORGANISM: Ebola virus

<400> SEQUENCE: 31
```

Gly His Gln Asp Asp Asp Pro Thr Asp Ser Gln Asp Thr Thr Ile Pro
1               5                   10                  15

Asp Val Val Val Asp Pro Asp Asp Gly Gly Tyr Gly Glu Tyr Gln Ser
                20                  25                  30

Tyr Ser Glu Asn Gly Met Ser Ala Pro Asp Asp Leu Val Leu Phe Asp
            35                  40                  45

Leu Asp Glu Asp Asp Glu
    50

<210> SEQ ID NO 32
<211> LENGTH: 101
<212> TYPE: PRT
<213> ORGANISM: Ebola virus

<400> SEQUENCE: 32

Thr Thr Ile Pro Asp Val Val Asp Pro Asp Gly Gly Tyr Gly
1               5                   10                  15

Glu Tyr Gln Ser Tyr Ser Glu Asn Gly Met Ser Ala Pro Asp Asp Leu
                20                  25                  30

Val Leu Phe Asp Leu Asp Glu Asp Glu Asp Thr Lys Pro Val Pro
            35                  40                  45

Asn Arg Ser Thr Lys Gly Gly Gln Gln Lys Asn Ser Gln Lys Gly Gln
        50                  55                  60

His Thr Glu Gly Arg Gln Thr Gln Ser Thr Pro Thr Gln Asn Val Thr
65                  70                  75                  80

Gly Pro Arg Arg Thr Ile His His Ala Ser Ala Pro Leu Thr Asp Asn
                85                  90                  95

Asp Arg Arg Asn Glu
            100

<210> SEQ ID NO 33
<211> LENGTH: 198
<212> TYPE: PRT
<213> ORGANISM: Ebola virus

<400> SEQUENCE: 33

Thr Ile Pro Asp Val Val Val Asp Pro Asp Gly Gly Tyr Gly Glu
1               5                   10                  15

Tyr Gln Ser Tyr Ser Glu Asn Gly Met Ser Ala Pro Asp Asp Leu Val
                20                  25                  30

Leu Phe Asp Leu Asp Glu Asp Glu Asp Thr Lys Pro Val Pro Asn
            35                  40                  45

Arg Ser Thr Lys Gly Gly Gln Gln Lys Asn Ser Gln Lys Gly Gln His
        50                  55                  60

Thr Glu Gly Arg Gln Thr Gln Ser Thr Pro Thr Gln Asn Val Thr Gly
65                  70                  75                  80

Pro Arg Arg Thr Ile His His Ala Ser Ala Pro Leu Thr Asp Asn Asp
                85                  90                  95

Arg Arg Asn Glu Pro Ser Gly Ser Thr Ser Pro Arg Met Leu Thr Pro
                100                 105                 110

Ile Asn Glu Glu Ala Asp Pro Leu Asp Asp Ala Asp Glu Thr Ser
            115                 120                 125

Ser Leu Pro Pro Leu Glu Ser Asp Asp Glu Glu Gln Asp Arg Asp Gly
        130                 135                 140

Thr Ser Asn Arg Thr Pro Thr Val Ala Pro Pro Ala Pro Val Tyr Arg
145                 150                 155                 160

Asp His Ser Glu Lys Lys Glu Leu Pro Gln Glu Gln Gln Asp Gln
                165                 170                 175

Asp His Ile Gln Glu Ala Arg Asn Gln Asp Ser Asp Asn Thr Gln Pro
            180                 185                 190

Glu His Ser Phe Glu Glu
        195

<210> SEQ ID NO 34
<211> LENGTH: 60
<212> TYPE: PRT
<213> ORGANISM: Ebola virus

<400> SEQUENCE: 34

Asp Pro Asp Asp Gly Gly Tyr Gly Glu Tyr Gln Ser Tyr Ser Glu Asn
1               5                   10                  15

Gly Met Ser Ala Pro Asp Asp Leu Val Leu Phe Asp Leu Asp Glu Asp
            20                  25                  30

Asp Glu Asp Thr Lys Pro Val Pro Asn Arg Ser Thr Lys Gly Gly Gln
        35                  40                  45

Gln Lys Asn Ser Gln Lys Gly Gln His Thr Glu Gly
    50                  55                  60

<210> SEQ ID NO 35
<211> LENGTH: 78
<212> TYPE: PRT
<213> ORGANISM: Ebola virus

<400> SEQUENCE: 35

Thr Ile His His Ala Ser Ala Pro Leu Thr Asp Asn Asp Arg Arg Asn
1               5                   10                  15

Glu Pro Ser Gly Ser Thr Ser Pro Arg Met Leu Thr Pro Ile Asn Glu
            20                  25                  30

Glu Ala Asp Pro Leu Asp Asp Ala Asp Asp Glu Thr Ser Ser Leu Pro
        35                  40                  45

Pro Leu Glu Ser Asp Asp Glu Glu Gln Asp Arg Asp Gly Thr Ser Asn
    50                  55                  60

Arg Thr Pro Thr Val Ala Pro Pro Ala Pro Val Tyr Arg Asp
65                  70                  75

<210> SEQ ID NO 36
<211> LENGTH: 121
<212> TYPE: PRT
<213> ORGANISM: Ebola virus

<400> SEQUENCE: 36

Ala Asp Pro Leu Asp Asp Ala Asp Asp Glu Thr Ser Ser Leu Pro Pro
1               5                   10                  15

Leu Glu Ser Asp Asp Glu Glu Gln Asp Arg Asp Gly Thr Ser Asn Arg
            20                  25                  30

Thr Pro Thr Val Ala Pro Pro Ala Pro Val Tyr Arg Asp His Ser Glu
        35                  40                  45

Lys Lys Glu Leu Pro Gln Asp Glu Gln Gln Asp Gln Asp His Ile Gln
    50                  55                  60

Glu Ala Arg Asn Gln Asp Ser Asp Asn Thr Gln Pro Glu His Ser Phe
65                  70                  75                  80

Glu Glu Met Tyr Arg His Ile Leu Arg Ser Gln Gly Pro Phe Asp Ala
                85                  90                  95

Val Leu Tyr Tyr His Met Met Lys Asp Glu Pro Val Val Phe Ser Thr
            100                 105                 110

Ser Asp Gly Lys Glu Tyr Thr Tyr Pro
        115                 120

<210> SEQ ID NO 37
<211> LENGTH: 91

```
<212> TYPE: PRT
<213> ORGANISM: Ebola virus

<400> SEQUENCE: 37

Asp Asn Thr Gln Pro Glu His Ser Phe Glu Met Tyr Arg His Ile
1               5                   10                  15

Leu Arg Ser Gln Gly Pro Phe Asp Ala Val Leu Tyr Tyr His Met Met
                20                  25                  30

Lys Asp Glu Pro Val Val Phe Ser Thr Ser Asp Gly Lys Glu Tyr Thr
            35                  40                  45

Tyr Pro Asp Ser Leu Glu Glu Glu Tyr Pro Pro Trp Leu Thr Glu Lys
        50                  55                  60

Glu Ala Met Asn Asp Glu Asn Arg Phe Val Thr Leu Asp Gly Gln Gln
65                  70                  75                  80

Phe Tyr Trp Pro Val Met Asn His Arg Asn Lys
                85                  90

<210> SEQ ID NO 38
<211> LENGTH: 28
<212> TYPE: PRT
<213> ORGANISM: Ebola virus

<400> SEQUENCE: 38

Met Thr Thr Arg Thr Lys Gly Arg Gly His Thr Val Ala Thr Thr Gln
1               5                   10                  15

Asn Asp Arg Met Pro Gly Pro Glu Leu Ser Gly Trp
                20                  25

<210> SEQ ID NO 39
<211> LENGTH: 129
<212> TYPE: PRT
<213> ORGANISM: Ebola virus

<400> SEQUENCE: 39

Met Thr Thr Arg Thr Lys Gly Arg Gly His Thr Val Ala Thr Thr Gln
1               5                   10                  15

Asn Asp Arg Met Pro Gly Pro Glu Leu Ser Gly Trp Ile Ser Glu Gln
                20                  25                  30

Leu Met Thr Gly Arg Ile Pro Val Asn Asp Ile Phe Cys Asp Ile Glu
            35                  40                  45

Asn Asn Pro Gly Leu Cys Tyr Ala Ser Gln Met Gln Gln Thr Lys Pro
        50                  55                  60

Asn Pro Lys Met Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

Ser

<210> SEQ ID NO 40
<211> LENGTH: 76
<212> TYPE: PRT
<213> ORGANISM: Ebola virus

<400> SEQUENCE: 40
```

Gly Arg Ile Pro Val Asn Asp Ile Phe Cys Asp Ile Glu Asn Asn Pro
1               5                   10                  15

Gly Leu Cys Tyr Ala Ser Gln Met Gln Gln Thr Lys Pro Asn Pro Lys
            20                  25                  30

Met Arg Asn Ser Gln Thr Gln Thr Asp Pro Ile Cys Asn His Ser Phe
            35                  40                  45

Glu Glu Val Val Gln Thr Leu Ala Ser Leu Ala Thr Val Val Gln Gln
50                  55                  60

Gln Thr Ile Ala Ser Glu Ser Leu Glu Gln Arg Ile
65                  70                  75

<210> SEQ ID NO 41
<211> LENGTH: 102
<212> TYPE: PRT
<213> ORGANISM: Ebola virus

<400> SEQUENCE: 41

Val Gln Gln Gln Thr Ile Ala Ser Glu Ser Leu Glu Gln Arg Ile Thr
1               5                   10                  15

Ser Leu Glu Asn Gly Leu Lys Pro Val Tyr Asp Met Ala Lys Thr Ile
            20                  25                  30

Ser Ser Leu Asn Arg Val Cys Ala Glu Met Val Ala Lys Tyr Asp Leu
            35                  40                  45

Leu Val Met Thr Thr Gly Arg Ala Thr Ala Thr Ala Ala Ala Thr Glu
50                  55                  60

Ala Tyr Trp Ala Glu His Gly Gln Pro Pro Pro Gly Pro Ser Leu Tyr
65                  70                  75                  80

Glu Glu Ser Ala Ile Arg Gly Lys Ile Glu Ser Arg Asp Glu Thr Val
            85                  90                  95

Pro Gln Ser Val Arg Glu
            100

<210> SEQ ID NO 42
<211> LENGTH: 180
<212> TYPE: PRT
<213> ORGANISM: Ebola virus

<400> SEQUENCE: 42

Glu Asn Gly Leu Lys Pro Val Tyr Asp Met Ala Lys Thr Ile Ser Ser
1               5                   10                  15

Leu Asn Arg Val Cys Ala Glu Met Val Ala Lys Tyr Asp Leu Leu Val
            20                  25                  30

Met Thr Thr Gly Arg Ala Thr Ala Thr Ala Ala Ala Thr Glu Ala Tyr
            35                  40                  45

Trp Ala Glu His Gly Gln Pro Pro Pro Gly Pro Ser Leu Tyr Glu Glu
50                  55                  60

Ser Ala Ile Arg Gly Lys Ile Glu Ser Arg Asp Glu Thr Val Pro Gln
65                  70                  75                  80

Ser Val Arg Glu Ala Phe Asn Asn Leu Asp Ser Thr Thr Ser Leu Thr
            85                  90                  95

Glu Glu Asn Phe Gly Lys Pro Asp Ile Ser Ala Lys Asp Leu Arg Asn
            100                 105                 110

Ile Met Tyr Asp His Leu Pro Gly Phe Gly Thr Ala Phe His Gln Leu
            115                 120                 125

Val Gln Val Ile Cys Lys Leu Gly Lys Asp Ser Asn Ser Leu Asp Ile
            130                 135                 140

Ile His Ala Glu Phe Gln Ala Ser Leu Ala Glu Gly Asp Ser Pro Gln
145                 150                 155                 160

Cys Ala Leu Ile Gln Ile Thr Lys Arg Val Pro Ile Phe Gln Asp Ala
            165                 170                 175

Ala Pro Pro Val
            180

<210> SEQ ID NO 43
<211> LENGTH: 108
<212> TYPE: PRT
<213> ORGANISM: Ebola virus

<400> SEQUENCE: 43

Val Cys Ala Glu Met Val Ala Lys Tyr Asp Leu Leu Val Met Thr Thr
1               5                   10                  15

Gly Arg Ala Thr Ala Thr Ala Ala Thr Glu Ala Tyr Trp Ala Glu
            20                  25                  30

His Gly Gln Pro Pro Gly Pro Ser Leu Tyr Glu Glu Ser Ala Ile
        35                  40                  45

Arg Gly Lys Ile Glu Ser Arg Asp Glu Thr Val Pro Gln Ser Val Arg
50                  55                  60

Glu Ala Phe Asn Asn Leu Asp Ser Thr Thr Ser Leu Thr Glu Glu Asn
65                  70                  75                  80

Phe Gly Lys Pro Asp Ile Ser Ala Lys Asp Leu Arg Asn Ile Met Tyr
                85                  90                  95

Asp His Leu Pro Gly Phe Gly Thr Ala Phe His Gln
            100                 105

<210> SEQ ID NO 44
<211> LENGTH: 44
<212> TYPE: PRT
<213> ORGANISM: Ebola virus

<400> SEQUENCE: 44

Ala Thr Ala Ala Ala Thr Glu Ala Tyr Trp Ala Glu His Gly Gln Pro
1               5                   10                  15

Pro Pro Gly Pro Ser Leu Tyr Glu Glu Ser Ala Ile Arg Gly Lys Ile
            20                  25                  30

Glu Ser Arg Asp Glu Thr Val Pro Gln Ser Val Arg
            35                  40

<210> SEQ ID NO 45
<211> LENGTH: 82
<212> TYPE: PRT
<213> ORGANISM: Ebola virus

<400> SEQUENCE: 45

Thr Ala Phe His Gln Leu Val Gln Val Ile Cys Lys Leu Gly Lys Asp
1               5                   10                  15

Ser Asn Ser Leu Asp Ile Ile His Ala Glu Phe Gln Ala Ser Leu Ala
            20                  25                  30

Glu Gly Asp Ser Pro Gln Cys Ala Leu Ile Gln Ile Thr Lys Arg Val
        35                  40                  45

Pro Ile Phe Gln Asp Ala Ala Pro Val Ile His Ile Arg Ser Arg
50                  55                  60

Gly Asp Ile Pro Arg Ala Cys Gln Lys Ser Leu Arg Pro Val Pro Pro
65                  70                  75                  80

Ser Pro

<210> SEQ ID NO 46
<211> LENGTH: 81
<212> TYPE: PRT
<213> ORGANISM: Ebola virus

<400> SEQUENCE: 46

Met Arg Arg Val Ile Leu Pro Thr Ala Pro Pro Glu Tyr Met Glu Ala
1               5                   10                  15

Ile Tyr Pro Ala Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val

<210> SEQ ID NO 47
<211> LENGTH: 183
<212> TYPE: PRT
<213> ORGANISM: Ebola virus

<400> SEQUENCE: 47

Met Arg Arg Val Ile Leu Pro Thr Ala Pro Pro Glu Tyr Met Glu Ala
1               5                   10                  15

Ile Tyr Pro Ala Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr
            180

<210> SEQ ID NO 48
<211> LENGTH: 41
<212> TYPE: PRT
<213> ORGANISM: Ebola virus

<400> SEQUENCE: 48

Asn Thr Gly Phe Leu Thr Pro Glu Ser Val Asn Gly Asp Thr Pro Ser

```
1               5                   10                  15
Asn Pro Leu Arg Pro Ile Ala Asp Asp Thr Ile Asp His Ala Ser His
                20                  25                  30

Thr Pro Gly Ser Val Ser Ser Ala Phe
            35                  40
```

<210> SEQ ID NO 49
<211> LENGTH: 121
<212> TYPE: PRT
<213> ORGANISM: Ebola virus

<400> SEQUENCE: 49

```
Pro Glu Ser Val Asn Gly Asp Thr Pro Ser Asn Pro Leu Arg Pro Ile
1               5                   10                  15

Ala Asp Asp Thr Ile Asp His Ala Ser His Thr Pro Gly Ser Val Ser
                20                  25                  30

Ser Ala Phe Ile Leu Glu Ala Met Val Asn Val Ile Ser Gly Pro Lys
            35                  40                  45

Val Leu Met Lys Gln Ile Pro Ile Trp Leu Pro Leu Gly Val Ala Asp
        50                  55                  60

Gln Lys Thr Tyr Ser Phe Asp Ser Thr Thr Ala Ala Ile Met Leu Ala
65                  70                  75                  80

Ser Tyr Thr Ile Thr His Phe Gly Lys Ala Thr Asn Pro Leu Val Arg
                85                  90                  95

Val Asn Arg Leu Gly Pro Gly Ile Pro Asp His Pro Leu Arg Leu Leu
            100                 105                 110

Arg Ile Gly Asn Gln Ala Phe Leu Gln
            115                 120
```

<210> SEQ ID NO 50
<211> LENGTH: 251
<212> TYPE: PRT
<213> ORGANISM: Ebola virus

<400> SEQUENCE: 50

```
Pro Glu Ser Val Asn Gly Asp Thr Pro Ser Asn Pro Leu Arg Pro Ile
1               5                   10                  15

Ala Asp Asp Thr Ile Asp His Ala Ser His Thr Pro Gly Ser Val Ser
                20                  25                  30

Ser Ala Phe Ile Leu Glu Ala Met Val Asn Val Ile Ser Gly Pro Lys
            35                  40                  45

Val Leu Met Lys Gln Ile Pro Ile Trp Leu Pro Leu Gly Val Ala Asp
        50                  55                  60

Gln Lys Thr Tyr Ser Phe Asp Ser Thr Thr Ala Ala Ile Met Leu Ala
65                  70                  75                  80

Ser Tyr Thr Ile Thr His Phe Gly Lys Ala Thr Asn Pro Leu Val Arg
                85                  90                  95

Val Asn Arg Leu Gly Pro Gly Ile Pro Asp His Pro Leu Arg Leu Leu
            100                 105                 110

Arg Ile Gly Asn Gln Ala Phe Leu Gln Glu Phe Val Leu Pro Pro Val
            115                 120                 125

Gln Leu Pro Gln Tyr Phe Thr Phe Asp Leu Thr Ala Leu Lys Leu Ile
        130                 135                 140

Thr Gln Pro Leu Pro Ala Ala Thr Trp Thr Asp Asp Thr Pro Thr Gly
145                 150                 155                 160

Ser Asn Gly Ala Leu Arg Pro Gly Ile Ser Phe His Pro Lys Leu Arg
```

```
                        165                 170                 175

Pro Ile Leu Leu Pro Asn Lys Ser Gly Lys Lys Gly Asn Ser Ala Asp
                180                 185                 190

Leu Thr Ser Pro Glu Lys Ile Gln Ala Ile Met Thr Ser Leu Gln Asp
            195                 200                 205

Phe Lys Ile Val Pro Ile Asp Pro Thr Lys Asn Ile Met Gly Ile Glu
        210                 215                 220

Val Pro Glu Thr Leu Val His Lys Leu Thr Gly Lys Lys Val Thr Ser
225                 230                 235                 240

Lys Asn Gly Gln Pro Ile Ile Pro Val Leu Leu
                245                 250

<210> SEQ ID NO 51
<211> LENGTH: 123
<212> TYPE: PRT
<213> ORGANISM: Ebola virus

<400> SEQUENCE: 51

Ser Ala Phe Ile Leu Glu Ala Met Val Asn Val Ile Ser Gly Pro Lys
1               5                   10                  15

Val Leu Met Lys Gln Ile Pro Ile Trp Leu Pro Leu Gly Val Ala Asp
            20                  25                  30

Gln Lys Thr Tyr Ser Phe Asp Ser Thr Thr Ala Ala Ile Met Leu Ala
        35                  40                  45

Ser Tyr Thr Ile Thr His Phe Gly Lys Ala Thr Asn Pro Leu Val Arg
    50                  55                  60

Val Asn Arg Leu Gly Pro Gly Ile Pro Asp His Pro Leu Arg Leu Leu
65                  70                  75                  80

Arg Ile Gly Asn Gln Ala Phe Leu Gln Glu Phe Val Leu Pro Pro Val
                85                  90                  95

Gln Leu Pro Gln Tyr Phe Thr Phe Asp Leu Thr Ala Leu Lys Leu Ile
            100                 105                 110

Thr Gln Pro Leu Pro Ala Ala Thr Trp Thr Asp
        115                 120

<210> SEQ ID NO 52
<211> LENGTH: 53
<212> TYPE: PRT
<213> ORGANISM: Ebola virus

<400> SEQUENCE: 52

Tyr Ser Phe Asp Ser Thr Thr Ala Ala Ile Met Leu Ala Ser Tyr Thr
1               5                   10                  15

Ile Thr His Phe Gly Lys Ala Thr Asn Pro Leu Val Arg Val Asn Arg
            20                  25                  30

Leu Gly Pro Gly Ile Pro Asp His Pro Leu Arg Leu Leu Arg Ile Gly
        35                  40                  45

Asn Gln Ala Phe Leu
    50

<210> SEQ ID NO 53
<211> LENGTH: 26
<212> TYPE: PRT
<213> ORGANISM: Ebola virus

<400> SEQUENCE: 53

Tyr Thr Ile Thr His Phe Gly Lys Ala Thr Asn Pro Leu Val Arg Val
1               5                   10                  15
```

```
Asn Arg Leu Gly Pro Gly Ile Pro Asp His
            20                  25
```

<210> SEQ ID NO 54
<211> LENGTH: 106
<212> TYPE: PRT
<213> ORGANISM: Ebola virus

<400> SEQUENCE: 54

```
Tyr Thr Ile Thr His Phe Gly Lys Ala Thr Asn Pro Leu Val Arg Val
1               5                   10                  15

Asn Arg Leu Gly Pro Gly Ile Pro Asp His Pro Leu Arg Leu Leu Arg
            20                  25                  30

Ile Gly Asn Gln Ala Phe Leu Gln Glu Phe Val Leu Pro Pro Val Gln
        35                  40                  45

Leu Pro Gln Tyr Phe Thr Phe Asp Leu Thr Ala Leu Lys Leu Ile Thr
    50                  55                  60

Gln Pro Leu Pro Ala Ala Thr Trp Thr Asp Asp Thr Pro Thr Gly Ser
65                  70                  75                  80

Asn Gly Ala Leu Arg Pro Gly Ile Ser Phe His Pro Lys Leu Arg Pro
                85                  90                  95

Ile Leu Leu Pro Asn Lys Ser Gly Lys Lys
            100                 105
```

<210> SEQ ID NO 55
<211> LENGTH: 74
<212> TYPE: PRT
<213> ORGANISM: Ebola virus

<400> SEQUENCE: 55

```
Gly Asn Gln Ala Phe Leu Gln Glu Phe Val Leu Pro Pro Val Gln Leu
1               5                   10                  15

Pro Gln Tyr Phe Thr Phe Asp Leu Thr Ala Leu Lys Leu Ile Thr Gln
            20                  25                  30

Pro Leu Pro Ala Ala Thr Trp Thr Asp Asp Thr Pro Thr Gly Ser Asn
        35                  40                  45

Gly Ala Leu Arg Pro Gly Ile Ser Phe His Pro Lys Leu Arg Pro Ile
    50                  55                  60

Leu Leu Pro Asn Lys Ser Gly Lys Lys Gly
65                  70
```

<210> SEQ ID NO 56
<211> LENGTH: 120
<212> TYPE: PRT
<213> ORGANISM: Ebola virus

<400> SEQUENCE: 56

```
Gln Pro Leu Pro Ala Ala Thr Trp Thr Asp Asp Thr Pro Thr Gly Ser
1               5                   10                  15

Asn Gly Ala Leu Arg Pro Gly Ile Ser Phe His Pro Lys Leu Arg Pro
            20                  25                  30

Ile Leu Leu Pro Asn Lys Ser Gly Lys Lys Gly Asn Ser Ala Asp Leu
        35                  40                  45

Thr Ser Pro Glu Lys Ile Gln Ala Ile Met Thr Ser Leu Gln Asp Phe
    50                  55                  60

Lys Ile Val Pro Ile Asp Pro Thr Lys Asn Ile Met Gly Ile Glu Val
65                  70                  75                  80
```

```
Pro Glu Thr Leu Val His Lys Leu Thr Gly Lys Lys Val Thr Ser Lys
                85                  90                  95

Asn Gly Gln Pro Ile Ile Pro Val Leu Leu Pro Lys Tyr Ile Gly Leu
            100                 105                 110

Asp Pro Val Ala Pro Gly Asp Leu
        115                 120

<210> SEQ ID NO 57
<211> LENGTH: 57
<212> TYPE: PRT
<213> ORGANISM: Ebola virus

<400> SEQUENCE: 57

Trp Thr Asp Asp Thr Pro Thr Gly Ser Asn Gly Ala Leu Arg Pro Gly
1               5                   10                  15

Ile Ser Phe His Pro Lys Leu Arg Pro Ile Leu Leu Pro Asn Lys Ser
                20                  25                  30

Gly Lys Lys Gly Asn Ser Ala Asp Leu Thr Ser Pro Glu Lys Ile Gln
            35                  40                  45

Ala Ile Met Thr Ser Leu Gln Asp Phe
        50                  55

<210> SEQ ID NO 58
<211> LENGTH: 45
<212> TYPE: PRT
<213> ORGANISM: Ebola virus

<400> SEQUENCE: 58

Gln Pro Ile Ile Pro Val Leu Leu Pro Lys Tyr Ile Gly Leu Asp Pro
1               5                   10                  15

Val Ala Pro Gly Asp Leu Thr Met Val Ile Thr Gln Asp Cys Asp Thr
                20                  25                  30

Cys His Ser Pro Ala Ser Leu Pro Ala Val Val Glu Lys
            35                  40                  45

<210> SEQ ID NO 59
<211> LENGTH: 16
<212> TYPE: PRT
<213> ORGANISM: Ebola virus

<400> SEQUENCE: 59

Met Gly Val Thr Gly Ile Leu Gln Leu Pro Arg Asp Arg Phe Lys Arg
1               5                   10                  15

<210> SEQ ID NO 60
<211> LENGTH: 36
<212> TYPE: PRT
<213> ORGANISM: Ebola virus

<400> SEQUENCE: 60

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly
        35

<210> SEQ ID NO 61
<211> LENGTH: 76
<212> TYPE: PRT
<213> ORGANISM: Ebola virus
```

<400> SEQUENCE: 61

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
                35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala
65                  70                  75

<210> SEQ ID NO 62
<211> LENGTH: 242
<212> TYPE: PRT
<213> ORGANISM: Ebola virus

<400> SEQUENCE: 62

Ser Ile Pro Leu Gly Val Ile His Asn Ser Thr Leu Gln Val Ser Asp
1               5                   10                  15

Val Asp Lys Leu Val Cys Arg Asp Lys Leu Ser Ser Thr Asn Gln Leu
            20                  25                  30

Arg Ser Val Gly Leu Asn Leu Glu Gly Asn Gly Val Ala Thr Asp Val
                35                  40                  45

Pro Ser Ala Thr Lys Arg Trp Gly Phe Arg Ser Gly Val Pro Pro Lys
    50                  55                  60

Val Val Asn Tyr Glu Ala Gly Glu Trp Ala Glu Asn Cys Tyr Asn Leu
65                  70                  75                  80

Glu Ile Lys Lys Pro Asp Gly Ser Glu Cys Leu Pro Ala Ala Pro Asp
                85                  90                  95

Gly Ile Arg Gly Phe Pro Arg Cys Arg Tyr Val His Lys Val Ser Gly
            100                 105                 110

Thr Gly Pro Cys Ala Gly Asp Phe Ala Phe His Lys Glu Gly Ala Phe
        115                 120                 125

Phe Leu Tyr Asp Arg Leu Ala Ser Thr Val Ile Tyr Arg Gly Thr Thr
130                 135                 140

Phe Ala Glu Gly Val Val Ala Phe Leu Ile Leu Pro Gln Ala Lys Lys
145                 150                 155                 160

Asp Phe Phe Ser Ser His Pro Leu Arg Glu Pro Val Asn Ala Thr Glu
                165                 170                 175

Asp Pro Ser Ser Gly Tyr Tyr Ser Thr Thr Ile Arg Tyr Gln Ala Thr
            180                 185                 190

Gly Phe Gly Thr Asn Glu Thr Glu Tyr Leu Phe Glu Val Asp Asn Leu
        195                 200                 205

Thr Tyr Val Gln Leu Glu Ser Arg Phe Thr Pro Gln Phe Leu Leu Gln
210                 215                 220

Leu Asn Glu Thr Ile Tyr Ala Ser Gly Lys Arg Ser Asn Thr Thr Gly
225                 230                 235                 240

Lys Leu

<210> SEQ ID NO 63
<211> LENGTH: 138
<212> TYPE: PRT
<213> ORGANISM: Ebola virus

<400> SEQUENCE: 63

```
Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Ala Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile
    130                 135
```

<210> SEQ ID NO 64
<211> LENGTH: 44
<212> TYPE: PRT
<213> ORGANISM: Ebola virus

<400> SEQUENCE: 64

```
Asn Gln Leu Arg Ser Val Gly Leu Asn Leu Glu Gly Asn Gly Val Ala
1               5                   10                  15

Thr Asp Val Pro Ser Ala Thr Lys Arg Trp Gly Phe Arg Ser Gly Val
            20                  25                  30

Pro Pro Lys Val Val Asn Tyr Glu Ala Gly Glu Trp
        35                  40
```

<210> SEQ ID NO 65
<211> LENGTH: 90
<212> TYPE: PRT
<213> ORGANISM: Ebola virus

<400> SEQUENCE: 65

```
Thr Asp Val Pro Ser Ala Thr Lys Arg Trp Gly Phe Arg Ser Gly Val
1               5                   10                  15

Pro Pro Lys Val Val Asn Tyr Glu Ala Gly Glu Trp Ala Glu Asn Cys
            20                  25                  30

Tyr Asn Leu Glu Ile Lys Lys Pro Asp Gly Ser Glu Cys Leu Pro Ala
        35                  40                  45

Ala Pro Asp Gly Ile Arg Gly Phe Pro Arg Cys Arg Tyr Val His Lys
    50                  55                  60

Val Ser Gly Thr Gly Pro Cys Ala Gly Asp Phe Ala Phe His Lys Glu
65                  70                  75                  80

Gly Ala Phe Phe Leu Tyr Asp Arg Leu Ala
                85                  90
```

<210> SEQ ID NO 66
<211> LENGTH: 186
<212> TYPE: PRT
<213> ORGANISM: Ebola virus

<400> SEQUENCE: 66

```
Glu Ile Lys Lys Pro Asp Gly Ser Glu Cys Leu Pro Ala Ala Pro Asp
1               5                   10                  15

Gly Ile Arg Gly Phe Pro Arg Cys Arg Tyr Val His Lys Val Ser Gly
                20                  25                  30

Thr Gly Pro Cys Ala Gly Asp Phe Ala Phe His Lys Glu Gly Ala Phe
            35                  40                  45

Phe Leu Tyr Asp Arg Leu Ala Ser Thr Val Ile Tyr Arg Gly Thr Thr
50                  55                  60

Phe Ala Glu Gly Val Val Ala Phe Leu Ile Leu Pro Gln Ala Lys Lys
65                  70                  75                  80

Asp Phe Phe Ser Ser His Pro Leu Arg Glu Pro Val Asn Ala Thr Glu
                85                  90                  95

Asp Pro Ser Ser Gly Tyr Tyr Ser Thr Thr Ile Arg Tyr Gln Ala Thr
                100                 105                 110

Gly Phe Gly Thr Asn Glu Thr Glu Tyr Leu Phe Glu Val Asp Asn Leu
            115                 120                 125

Thr Tyr Val Gln Leu Glu Ser Arg Phe Thr Pro Gln Phe Leu Leu Gln
        130                 135                 140

Leu Asn Glu Thr Ile Tyr Ala Ser Gly Lys Arg Ser Asn Thr Thr Gly
145                 150                 155                 160

Lys Leu Ile Trp Lys Val Asn Pro Glu Ile Asp Thr Thr Ile Gly Glu
                165                 170                 175

Trp Ala Phe Trp Glu Thr Lys Lys Asn Leu
                180                 185

<210> SEQ ID NO 67
<211> LENGTH: 69
<212> TYPE: PRT
<213> ORGANISM: Ebola virus

<400> SEQUENCE: 67

Ala Phe His Lys Glu Gly Ala Phe Phe Leu Tyr Asp Arg Leu Ala Ser
1               5                   10                  15

Thr Val Ile Tyr Arg Gly Thr Thr Phe Ala Glu Gly Val Val Ala Phe
                20                  25                  30

Leu Ile Leu Pro Gln Ala Lys Lys Asp Phe Phe Ser Ser His Pro Leu
            35                  40                  45

Arg Glu Pro Val Asn Ala Thr Glu Asp Pro Ser Ser Gly Tyr Tyr Ser
        50                  55                  60

Thr Thr Ile Arg Tyr
65

<210> SEQ ID NO 68
<211> LENGTH: 32
<212> TYPE: PRT
<213> ORGANISM: Ebola virus

<400> SEQUENCE: 68

Ser Ser His Pro Leu Arg Glu Pro Val Asn Ala Thr Glu Asp Pro Ser
1               5                   10                  15

Ser Gly Tyr Tyr Ser Thr Thr Ile Arg Tyr Gln Ala Thr Gly Phe Gly
                20                  25                  30

<210> SEQ ID NO 69
<211> LENGTH: 160
<212> TYPE: PRT
<213> ORGANISM: Ebola virus
```

<400> SEQUENCE: 69

Ala Thr Glu Asp Pro Ser Ser Gly Tyr Tyr Ser Thr Thr Ile Arg Tyr
1               5                   10                  15

Gln Ala Thr Gly Phe Gly Thr Asn Glu Thr Glu Tyr Leu Phe Glu Val
            20                  25                  30

Asp Asn Leu Thr Tyr Val Gln Leu Glu Ser Arg Phe Thr Pro Gln Phe
        35                  40                  45

Leu Leu Gln Leu Asn Glu Thr Ile Tyr Ala Ser Gly Lys Arg Ser Asn
    50                  55                  60

Thr Thr Gly Lys Leu Ile Trp Lys Val Asn Pro Glu Ile Asp Thr Thr
65                  70                  75                  80

Ile Gly Glu Trp Ala Phe Trp Glu Thr Lys Lys Asn Leu Thr Arg Lys
                85                  90                  95

Ile Arg Ser Glu Glu Leu Ser Phe Thr Ala Val Ser Asn Gly Pro Lys
            100                 105                 110

Asn Ile Ser Gly Gln Ser Pro Ala Arg Thr Ser Ser Asp Pro Glu Thr
        115                 120                 125

Asn Thr Thr Asn Glu Asp His Lys Ile Met Ala Ser Glu Asn Ser Ser
    130                 135                 140

Ala Met Val Gln Val His Ser Gln Gly Arg Lys Ala Ala Val Ser His
145                 150                 155                 160

<210> SEQ ID NO 70
<211> LENGTH: 60
<212> TYPE: PRT
<213> ORGANISM: Ebola virus

<400> SEQUENCE: 70

Tyr Leu Phe Glu Val Asp Asn Leu Thr Tyr Val Gln Leu Glu Ser Arg
1               5                   10                  15

Phe Thr Pro Gln Phe Leu Leu Gln Leu Asn Glu Thr Ile Tyr Ala Ser
            20                  25                  30

Gly Lys Arg Ser Asn Thr Thr Gly Lys Leu Ile Trp Lys Val Asn Pro
        35                  40                  45

Glu Ile Asp Thr Thr Ile Gly Glu Trp Ala Phe Trp
    50                  55                  60

<210> SEQ ID NO 71
<211> LENGTH: 168
<212> TYPE: PRT
<213> ORGANISM: Ebola virus

<400> SEQUENCE: 71

Ser Asn Thr Thr Gly Lys Leu Ile Trp Lys Val Asn Pro Glu Ile Asp
1               5                   10                  15

Thr Thr Ile Gly Glu Trp Ala Phe Trp Glu Thr Lys Lys Asn Leu Thr
            20                  25                  30

Arg Lys Ile Arg Ser Glu Glu Leu Ser Phe Thr Ala Val Ser Asn Gly
        35                  40                  45

Pro Lys Asn Ile Ser Gly Gln Ser Pro Ala Arg Thr Ser Ser Asp Pro
    50                  55                  60

Glu Thr Asn Thr Thr Asn Glu Asp His Lys Ile Met Ala Ser Glu Asn
65                  70                  75                  80

Ser Ser Ala Met Val Gln Val His Ser Gln Gly Arg Lys Ala Ala Val
                85                  90                  95

```
Ser His Leu Thr Thr Leu Ala Thr Ile Ser Thr Ser Pro Gln Pro Pro
            100                 105                 110

Thr Thr Lys Thr Gly Pro Asp Asn Ser Thr His Asn Thr Pro Val Tyr
        115                 120                 125

Lys Leu Asp Ile Ser Glu Ala Thr Gln Val Gly Gln His His Arg Arg
    130                 135                 140

Ala Asp Asn Asp Ser Thr Ala Ser Asp Thr Pro Pro Ala Thr Thr Ala
145                 150                 155                 160

Ala Gly Pro Leu Lys Ala Glu Asn
                165

<210> SEQ ID NO 72
<211> LENGTH: 24
<212> TYPE: PRT
<213> ORGANISM: Ebola virus

<400> SEQUENCE: 72

Asp Thr Thr Ile Gly Glu Trp Ala Phe Trp Glu Thr Lys Lys Asn Leu
1               5                   10                  15

Thr Arg Lys Ile Arg Ser Glu Glu
            20

<210> SEQ ID NO 73
<211> LENGTH: 79
<212> TYPE: PRT
<213> ORGANISM: Ebola virus

<400> SEQUENCE: 73

Gly Glu Trp Ala Phe Trp Glu Thr Lys Lys Asn Leu Thr Arg Lys Ile
1               5                   10                  15

Arg Ser Glu Glu Leu Ser Phe Thr Ala Val Ser Asn Gly Pro Lys Asn
            20                  25                  30

Ile Ser Gly Gln Ser Pro Ala Arg Thr Ser Ser Asp Pro Glu Thr Asn
        35                  40                  45

Thr Thr Asn Glu Asp His Lys Ile Met Ala Ser Glu Asn Ser Ser Ala
    50                  55                  60

Met Val Gln Val His Ser Gln Gly Arg Lys Ala Ala Val Ser His
65                  70                  75

<210> SEQ ID NO 74
<211> LENGTH: 26
<212> TYPE: PRT
<213> ORGANISM: Ebola virus

<400> SEQUENCE: 74

Thr Ser Ser Asp Pro Glu Thr Asn Thr Thr Asn Glu Asp His Lys Ile
1               5                   10                  15

Met Ala Ser Glu Asn Ser Ser Ala Met Val
            20                  25

<210> SEQ ID NO 75
<211> LENGTH: 78
<212> TYPE: PRT
<213> ORGANISM: Ebola virus

<400> SEQUENCE: 75

Thr Ser Ser Asp Pro Glu Thr Asn Thr Thr Asn Glu Asp His Lys Ile
1               5                   10                  15

Met Ala Ser Glu Asn Ser Ser Ala Met Val Gln Val His Ser Gln Gly
            20                  25                  30
```

```
Arg Lys Ala Ala Val Ser His Leu Thr Thr Leu Ala Thr Ile Ser Thr
            35                  40                  45

Ser Pro Gln Pro Pro Thr Thr Lys Thr Gly Pro Asp Asn Ser Thr His
 50                  55                  60

Asn Thr Pro Val Tyr Lys Leu Asp Ile Ser Glu Ala Thr Gln
 65                  70                  75

<210> SEQ ID NO 76
<211> LENGTH: 177
<212> TYPE: PRT
<213> ORGANISM: Ebola virus

<400> SEQUENCE: 76

Ser Asp Pro Glu Thr Asn Thr Thr Asn Glu Asp His Lys Ile Met Ala
 1               5                  10                  15

Ser Glu Asn Ser Ser Ala Met Val Gln Val His Ser Gln Gly Arg Lys
            20                  25                  30

Ala Ala Val Ser His Leu Thr Thr Leu Ala Thr Ile Ser Thr Ser Pro
        35                  40                  45

Gln Pro Pro Thr Thr Lys Thr Gly Pro Asp Asn Ser Thr His Asn Thr
 50                  55                  60

Pro Val Tyr Lys Leu Asp Ile Ser Glu Ala Thr Gln Val Gly Gln His
 65                  70                  75                  80

His Arg Arg Ala Asp Asn Asp Ser Thr Ala Ser Asp Thr Pro Pro Ala
                85                  90                  95

Thr Thr Ala Ala Gly Pro Leu Lys Ala Glu Asn Thr Asn Thr Ser Lys
            100                 105                 110

Ser Ala Asp Ser Leu Asp Leu Ala Thr Thr Thr Ser Pro Gln Asn Tyr
        115                 120                 125

Ser Glu Thr Ala Gly Asn Asn Asn Thr His His Gln Asp Thr Gly Glu
    130                 135                 140

Glu Ser Ala Ser Ser Gly Lys Leu Gly Leu Ile Thr Asn Thr Ile Ala
145                 150                 155                 160

Gly Val Ala Gly Leu Ile Thr Gly Gly Arg Arg Thr Arg Arg Glu Val
                165                 170                 175

Ile

<210> SEQ ID NO 77
<211> LENGTH: 247
<212> TYPE: PRT
<213> ORGANISM: Ebola virus

<400> SEQUENCE: 77

Asn Glu Asp His Lys Ile Met Ala Ser Glu Asn Ser Ser Ala Met Val
 1               5                  10                  15

Gln Val His Ser Gln Gly Arg Lys Ala Ala Val Ser His Leu Thr Thr
            20                  25                  30

Leu Ala Thr Ile Ser Thr Ser Pro Gln Pro Pro Thr Thr Lys Thr Gly
        35                  40                  45

Pro Asp Asn Ser Thr His Asn Thr Pro Val Tyr Lys Leu Asp Ile Ser
    50                  55                  60

Glu Ala Thr Gln Val Gly Gln His His Arg Arg Ala Asp Asn Asp Ser
 65                  70                  75                  80

Thr Ala Ser Asp Thr Pro Pro Ala Thr Thr Ala Ala Gly Pro Leu Lys
                85                  90                  95
```

Ala Glu Asn Thr Asn Thr Ser Lys Ser Ala Asp Ser Leu Asp Leu Ala
            100                 105                 110

Thr Thr Thr Ser Pro Gln Asn Tyr Ser Glu Thr Ala Gly Asn Asn Asn
        115                 120                 125

Thr His His Gln Asp Thr Gly Glu Glu Ser Ala Ser Ser Gly Lys Leu
    130                 135                 140

Gly Leu Ile Thr Asn Thr Ile Ala Gly Val Ala Gly Leu Ile Thr Gly
145                 150                 155                 160

Gly Arg Arg Thr Arg Arg Glu Val Ile Val Asn Ala Gln Pro Lys Cys
                165                 170                 175

Asn Pro Asn Leu His Tyr Trp Thr Thr Gln Asp Glu Gly Ala Ala Ile
            180                 185                 190

Gly Leu Ala Trp Ile Pro Tyr Phe Gly Pro Ala Ala Glu Gly Ile Tyr
        195                 200                 205

Thr Glu Gly Leu Met His Asn Gln Asn Gly Leu Ile Cys Gly Leu Arg
    210                 215                 220

Gln Leu Ala Asn Glu Thr Thr Gln Ala Leu Gln Leu Phe Leu Arg Ala
225                 230                 235                 240

Thr Thr Glu Leu Arg Thr Phe
                245

<210> SEQ ID NO 78
<211> LENGTH: 26
<212> TYPE: PRT
<213> ORGANISM: Ebola virus

<400> SEQUENCE: 78

Ala Ser Glu Asn Ser Ser Ala Met Val Gln Val His Ser Gln Gly Arg
1               5                   10                  15

Lys Ala Ala Val Ser His Leu Thr Thr Leu
                20                  25

<210> SEQ ID NO 79
<211> LENGTH: 75
<212> TYPE: PRT
<213> ORGANISM: Ebola virus

<400> SEQUENCE: 79

Leu Ala Thr Ile Ser Thr Ser Pro Gln Pro Pro Thr Thr Lys Thr Gly
1               5                   10                  15

Pro Asp Asn Ser Thr His Asn Thr Pro Val Tyr Lys Leu Asp Ile Ser
                20                  25                  30

Glu Ala Thr Gln Val Gly Gln His His Arg Arg Ala Asp Asn Asp Ser
            35                  40                  45

Thr Ala Ser Asp Thr Pro Pro Ala Thr Ala Ala Gly Pro Leu Lys
        50                  55                  60

Ala Glu Asn Thr Asn Thr Ser Lys Ser Ala Asp
65                  70                  75

<210> SEQ ID NO 80
<211> LENGTH: 112
<212> TYPE: PRT
<213> ORGANISM: Ebola virus

<400> SEQUENCE: 80

Thr Lys Thr Gly Pro Asp Asn Ser Thr His Asn Thr Pro Val Tyr Lys
1               5                   10                  15

Leu Asp Ile Ser Glu Ala Thr Gln Val Gly Gln His His Arg Arg Ala

```
                20                  25                  30
Asp Asn Asp Ser Thr Ala Ser Asp Thr Pro Pro Ala Thr Ala Ala
            35                  40                  45

Gly Pro Leu Lys Ala Glu Asn Thr Asn Thr Ser Lys Ser Ala Asp Ser
 50                  55                  60

Leu Asp Leu Ala Thr Thr Thr Ser Pro Gln Asn Tyr Ser Glu Thr Ala
 65                  70                  75                  80

Gly Asn Asn Asn Thr His His Gln Asp Thr Gly Glu Glu Ser Ala Ser
                85                  90                  95

Ser Gly Lys Leu Gly Leu Ile Thr Asn Thr Ile Ala Gly Val Ala Gly
            100                 105                 110
```

<210> SEQ ID NO 81
<211> LENGTH: 99
<212> TYPE: PRT
<213> ORGANISM: Ebola virus

<400> SEQUENCE: 81

```
Lys Leu Asp Ile Ser Glu Ala Thr Gln Val Gly Gln His His Arg Arg
 1               5                  10                  15

Ala Asp Asn Asp Ser Thr Ala Ser Asp Thr Pro Pro Ala Thr Thr Ala
                20                  25                  30

Ala Gly Pro Leu Lys Ala Glu Asn Thr Asn Thr Ser Lys Ser Ala Asp
            35                  40                  45

Ser Leu Asp Leu Ala Thr Thr Thr Ser Pro Gln Asn Tyr Ser Glu Thr
 50                  55                  60

Ala Gly Asn Asn Asn Thr His His Gln Asp Thr Gly Glu Glu Ser Ala
 65                  70                  75                  80

Ser Ser Gly Lys Leu Gly Leu Ile Thr Asn Thr Ile Ala Gly Val Ala
                85                  90                  95

Gly Leu Ile
```

<210> SEQ ID NO 82
<211> LENGTH: 73
<212> TYPE: PRT
<213> ORGANISM: Ebola virus

<400> SEQUENCE: 82

```
Asp Thr Pro Pro Ala Thr Thr Ala Ala Gly Pro Leu Lys Ala Glu Asn
 1               5                  10                  15

Thr Asn Thr Ser Lys Ser Ala Asp Ser Leu Asp Leu Ala Thr Thr Thr
                20                  25                  30

Ser Pro Gln Asn Tyr Ser Glu Thr Ala Gly Asn Asn Asn Thr His His
            35                  40                  45

Gln Asp Thr Gly Glu Glu Ser Ala Ser Ser Gly Lys Leu Gly Leu Ile
 50                  55                  60

Thr Asn Thr Ile Ala Gly Val Ala Gly
 65                  70
```

<210> SEQ ID NO 83
<211> LENGTH: 24
<212> TYPE: PRT
<213> ORGANISM: Ebola virus

<400> SEQUENCE: 83

```
Thr Thr Ala Ala Gly Pro Leu Lys Ala Glu Asn Thr Asn Thr Ser Lys
 1               5                  10                  15
```

Ser Ala Asp Ser Leu Asp Leu Ala
            20

<210> SEQ ID NO 84
<211> LENGTH: 238
<212> TYPE: PRT
<213> ORGANISM: Ebola virus

<400> SEQUENCE: 84

Leu Lys Ala Glu Asn Thr Asn Thr Ser Lys Ser Ala Asp Ser Leu Asp
1               5                   10                  15

Leu Ala Thr Thr Thr Ser Pro Gln Asn Tyr Ser Glu Thr Ala Gly Asn
            20                  25                  30

Asn Asn Thr His His Gln Asp Thr Gly Glu Glu Ser Ala Ser Ser Gly
        35                  40                  45

Lys Leu Gly Leu Ile Thr Asn Thr Ile Ala Gly Val Ala Gly Leu Ile
    50                  55                  60

Thr Gly Gly Arg Arg Thr Arg Arg Glu Val Ile Val Asn Ala Gln Pro
65                  70                  75                  80

Lys Cys Asn Pro Asn Leu His Tyr Trp Thr Thr Gln Asp Glu Gly Ala
                85                  90                  95

Ala Ile Gly Leu Ala Trp Ile Pro Tyr Phe Gly Pro Ala Ala Glu Gly
            100                 105                 110

Ile Tyr Thr Glu Gly Leu Met His Asn Gln Asn Gly Leu Ile Cys Gly
        115                 120                 125

Leu Arg Gln Leu Ala Asn Glu Thr Thr Gln Ala Leu Gln Leu Phe Leu
    130                 135                 140

Arg Ala Thr Thr Glu Leu Arg Thr Phe Ser Ile Leu Asn Arg Lys Ala
145                 150                 155                 160

Ile Asp Phe Leu Leu Gln Arg Trp Gly Gly Thr Cys His Ile Leu Gly
                165                 170                 175

Pro Asp Cys Cys Ile Glu Pro His Asp Trp Thr Lys Asn Ile Thr Asp
            180                 185                 190

Lys Ile Asp Gln Ile Ile His Asp Phe Val Asp Lys Thr Leu Pro Asp
        195                 200                 205

Gln Gly Asp Asn Asp Asn Trp Trp Thr Gly Trp Arg Gln Trp Ile Pro
    210                 215                 220

Ala Gly Ile Gly Val Thr Gly Val Ile Ala Val Ile Ala
225                 230                 235

<210> SEQ ID NO 85
<211> LENGTH: 29
<212> TYPE: PRT
<213> ORGANISM: Ebola virus

<400> SEQUENCE: 85

Ser Glu Thr Ala Gly Asn Asn Asn Thr His His Gln Asp Thr Gly Glu
1               5                   10                  15

Glu Ser Ala Ser Ser Gly Lys Leu Gly Leu Ile Thr Asn
            20                  25

<210> SEQ ID NO 86
<211> LENGTH: 30
<212> TYPE: PRT
<213> ORGANISM: Ebola virus

<400> SEQUENCE: 86

Thr Gly Glu Glu Ser Ala Ser Ser Gly Lys Leu Gly Leu Ile Thr Asn

```
                  1               5                  10                 15
Thr Ile Ala Gly Val Ala Gly Leu Ile Thr Gly Gly Arg Arg
              20                  25                 30
```

<210> SEQ ID NO 87
<211> LENGTH: 28
<212> TYPE: PRT
<213> ORGANISM: Ebola virus

<400> SEQUENCE: 87

```
Thr Gln Asp Glu Gly Ala Ala Ile Gly Leu Ala Trp Ile Pro Tyr Phe
1               5                   10                  15

Gly Pro Ala Ala Glu Gly Ile Tyr Thr Glu Gly Leu
            20                  25
```

<210> SEQ ID NO 88
<211> LENGTH: 63
<212> TYPE: PRT
<213> ORGANISM: Ebola virus

<400> SEQUENCE: 88

```
Thr Gln Asp Glu Gly Ala Ala Ile Gly Leu Ala Trp Ile Pro Tyr Phe
1               5                   10                  15

Gly Pro Ala Ala Glu Gly Ile Tyr Thr Glu Gly Leu Met His Asn Gln
            20                  25                  30

Asn Gly Leu Ile Cys Gly Leu Arg Gln Leu Ala Asn Glu Thr Thr Gln
        35                  40                  45

Ala Leu Gln Leu Phe Leu Arg Ala Thr Thr Glu Leu Arg Thr Phe
    50                  55                  60
```

<210> SEQ ID NO 89
<211> LENGTH: 136
<212> TYPE: PRT
<213> ORGANISM: Ebola virus

<400> SEQUENCE: 89

```
Ile Pro Tyr Phe Gly Pro Ala Ala Glu Gly Ile Tyr Thr Glu Gly Leu
1               5                   10                  15

Met His Asn Gln Asn Gly Leu Ile Cys Gly Leu Arg Gln Leu Ala Asn
            20                  25                  30

Glu Thr Thr Gln Ala Leu Gln Leu Phe Leu Arg Ala Thr Thr Glu Leu
        35                  40                  45

Arg Thr Phe Ser Ile Leu Asn Arg Lys Ala Ile Asp Phe Leu Leu Gln
    50                  55                  60

Arg Trp Gly Gly Thr Cys His Ile Leu Gly Pro Asp Cys Cys Ile Glu
65                  70                  75                  80

Pro His Asp Trp Thr Lys Asn Ile Thr Asp Lys Ile Asp Gln Ile Ile
                85                  90                  95

His Asp Phe Val Asp Lys Thr Leu Pro Asp Gln Gly Asp Asn Asp Asn
            100                 105                 110

Trp Trp Thr Gly Trp Arg Gln Trp Ile Pro Ala Gly Ile Gly Val Thr
        115                 120                 125

Gly Val Ile Ile Ala Val Ile Ala
    130                 135
```

<210> SEQ ID NO 90
<211> LENGTH: 49
<212> TYPE: PRT
<213> ORGANISM: Ebola virus

<400> SEQUENCE: 90

Leu Gln Leu Phe Leu Arg Ala Thr Thr Glu Leu Arg Thr Phe Ser Ile
1               5                   10                  15

Leu Asn Arg Lys Ala Ile Asp Phe Leu Leu Gln Arg Trp Gly Gly Thr
            20                  25                  30

Cys His Ile Leu Gly Pro Asp Cys Cys Ile Glu Pro His Asp Trp Thr
        35                  40                  45

Lys

<210> SEQ ID NO 91
<211> LENGTH: 39
<212> TYPE: PRT
<213> ORGANISM: Ebola virus

<400> SEQUENCE: 91

Asp Cys Cys Ile Glu Pro His Asp Trp Thr Lys Asn Ile Thr Asp Lys
1               5                   10                  15

Ile Asp Gln Ile Ile His Asp Phe Val Asp Lys Thr Leu Pro Asp Gln
            20                  25                  30

Gly Asp Asn Asp Asn Trp Trp
        35

<210> SEQ ID NO 92
<211> LENGTH: 59
<212> TYPE: PRT
<213> ORGANISM: Ebola virus

<400> SEQUENCE: 92

Cys Ile Glu Pro His Asp Trp Thr Lys Asn Ile Thr Asp Lys Ile Asp
1               5                   10                  15

Gln Ile Ile His Asp Phe Val Asp Lys Thr Leu Pro Asp Gln Gly Asp
            20                  25                  30

Asn Asp Asn Trp Trp Thr Gly Trp Arg Gln Trp Ile Pro Ala Gly Ile
        35                  40                  45

Gly Val Thr Gly Val Ile Ile Ala Val Ile Ala
    50                  55

<210> SEQ ID NO 93
<211> LENGTH: 33
<212> TYPE: PRT
<213> ORGANISM: Ebola virus

<400> SEQUENCE: 93

Leu Pro Asp Gln Gly Asp Asn Asp Asn Trp Trp Thr Gly Trp Arg Gln
1               5                   10                  15

Trp Ile Pro Ala Gly Ile Gly Val Thr Gly Val Ile Ile Ala Val Ile
            20                  25                  30

Ala

<210> SEQ ID NO 94
<211> LENGTH: 155
<212> TYPE: PRT
<213> ORGANISM: Ebola virus

<400> SEQUENCE: 94

Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Ser Arg

```
                 20                  25                  30

Glu Asn Tyr Arg Gly Glu Tyr Arg Gln Ser Arg Ser Ala Ser Gln Val
             35                  40                  45

Arg Val Pro Thr Val Phe His Lys Lys Arg Val Glu Pro Leu Thr Val
 50                  55                  60

Pro Pro Ala Pro Lys Asp Ile Cys Pro Thr Leu Lys Lys Gly Phe Leu
 65                  70                  75                  80

Cys Asp Ser Ser Phe Cys Lys Lys Asp His Gln Leu Glu Ser Leu Thr
                 85                  90                  95

Asp Arg Glu Leu Leu Leu Ile Ala Arg Lys Thr Cys Gly Ser Val
             100                 105                 110

Glu Gln Gln Leu Asn Ile Thr Ala Pro Lys Asp Ser Arg Leu Ala Asn
             115                 120                 125

Pro Thr Ala Asp Asp Phe Gln Gln Glu Glu Gly Pro Lys Ile Thr Leu
         130                 135                 140

Leu Thr Leu Ile Lys Thr Ala Glu His Trp Ala
145                 150                 155

<210> SEQ ID NO 95
<211> LENGTH: 93
<212> TYPE: PRT
<213> ORGANISM: Ebola virus

<400> SEQUENCE: 95

Leu Lys Lys Gly Phe Leu Cys Asp Ser Ser Phe Cys Lys Lys Asp His
1               5                   10                  15

Gln Leu Glu Ser Leu Thr Asp Arg Glu Leu Leu Leu Ile Ala Arg
             20                  25                  30

Lys Thr Cys Gly Ser Val Glu Gln Gln Leu Asn Ile Thr Ala Pro Lys
             35                  40                  45

Asp Ser Arg Leu Ala Asn Pro Thr Ala Asp Asp Phe Gln Gln Glu Glu
         50                  55                  60

Gly Pro Lys Ile Thr Leu Leu Thr Leu Ile Lys Thr Ala Glu His Trp
65                  70                  75                  80

Ala Arg Gln Asp Ile Arg Thr Ile Glu Asp Ser Lys Leu
                 85                  90

<210> SEQ ID NO 96
<211> LENGTH: 73
<212> TYPE: PRT
<213> ORGANISM: Ebola virus

<400> SEQUENCE: 96

Ile Thr Ala Pro Lys Asp Ser Arg Leu Ala Asn Pro Thr Ala Asp Asp
1               5                   10                  15

Phe Gln Gln Glu Glu Gly Pro Lys Ile Thr Leu Leu Thr Leu Ile Lys
             20                  25                  30

Thr Ala Glu His Trp Ala Arg Gln Asp Ile Arg Thr Ile Glu Asp Ser
             35                  40                  45

Lys Leu Arg Ala Leu Leu Thr Leu Cys Ala Val Met Thr Arg Lys Phe
         50                  55                  60

Ser Lys Ser Gln Leu Ser Leu Leu Cys
65                  70

<210> SEQ ID NO 97
<211> LENGTH: 84
<212> TYPE: PRT
```

-continued

<213> ORGANISM: Ebola virus

<400> SEQUENCE: 97

Leu Ile Lys Thr Ala Glu His Trp Ala Arg Gln Asp Ile Arg Thr Ile
1               5                   10                  15

Glu Asp Ser Lys Leu Arg Ala Leu Leu Thr Leu Cys Ala Val Met Thr
            20                  25                  30

Arg Lys Phe Ser Lys Ser Gln Leu Ser Leu Leu Cys Glu Thr His Leu
        35                  40                  45

Arg Arg Glu Gly Leu Gly Gln Asp Gln Ala Glu Pro Val Leu Glu Val
    50                  55                  60

Tyr Gln Arg Leu His Ser Asp Lys Gly Gly Ser Phe Glu Ala Ala Leu
65                  70                  75                  80

Trp Gln Gln Trp

<210> SEQ ID NO 98
<211> LENGTH: 33
<212> TYPE: PRT
<213> ORGANISM: Ebola virus

<400> SEQUENCE: 98

Ala Val Val Val Ser Gly Leu Arg Thr Leu Val Pro Gln Ser Asp Asn
1               5                   10                  15

Glu Glu Ala Ser Thr Asn Pro Gly Thr Cys Ser Trp Ser Asp Glu Gly
            20                  25                  30

Thr

<210> SEQ ID NO 99
<211> LENGTH: 93
<212> TYPE: PRT
<213> ORGANISM: Ebola virus

<400> SEQUENCE: 99

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
        35                  40                  45

Val Thr His Lys Gly Met Ala Leu Leu His Arg Leu Lys Thr Asn Asp
    50                  55                  60

Phe Ala Pro Ala Trp Ser Met Thr Arg Asn Leu Phe Pro His Leu Phe
65                  70                  75                  80

Gln Asn Pro Asn Ser Thr Ile Glu Ser Pro Leu Trp Ala
                85                  90

<210> SEQ ID NO 100
<211> LENGTH: 212
<212> TYPE: PRT
<213> ORGANISM: Ebola virus

<400> SEQUENCE: 100

Met Ala Lys Ala Thr Gly Arg Tyr Asn Leu Ile Ser Pro Lys Lys Asp
1               5                   10                  15

Leu Glu Lys Gly Val Val Leu Ser Asp Leu Cys Asn Phe Leu Val Ser
            20                  25                  30

Gln Thr Ile Gln Gly Trp Lys Val Tyr Trp Ala Gly Ile Glu Phe Asp
        35                  40                  45

```
Val Thr His Lys Gly Met Ala Leu Leu His Arg Leu Lys Thr Asn Asp
 50                  55                  60

Phe Ala Pro Ala Trp Ser Met Thr Arg Asn Leu Phe Pro His Leu Phe
 65                  70                  75                  80

Gln Asn Pro Asn Ser Thr Ile Glu Ser Pro Leu Trp Ala Leu Arg Val
                 85                  90                  95

Ile Leu Ala Ala Gly Ile Gln Asp Gln Leu Ile Asp Gln Ser Leu Ile
                100                 105                 110

Glu Pro Leu Ala Gly Ala Leu Gly Leu Ile Ser Asp Trp Leu Leu Thr
            115                 120                 125

Thr Asn Thr Asn His Phe Asn Met Arg Thr Gln Arg Val Lys Glu Gln
        130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Thr Arg
            180                 185                 190

Thr Asn Met Gly Phe Leu Val Glu Leu Gln Glu Pro Asp Lys Ser Ala
            195                 200                 205

Met Asn Arg Lys
    210

<210> SEQ ID NO 101
<211> LENGTH: 76
<212> TYPE: PRT
<213> ORGANISM: Ebola virus

<400> SEQUENCE: 101

Thr His Lys Gly Met Ala Leu Leu His Arg Leu Lys Thr Asn Asp Phe
  1               5                  10                  15

Ala Pro Ala Trp Ser Met Thr Arg Asn Leu Phe Pro His Leu Phe Gln
                 20                  25                  30

Asn Pro Asn Ser Thr Ile Glu Ser Pro Leu Trp Ala Leu Arg Val Ile
             35                  40                  45

Leu Ala Ala Gly Ile Gln Asp Gln Leu Ile Asp Gln Ser Leu Ile Glu
 50                  55                  60

Pro Leu Ala Gly Ala Leu Gly Leu Ile Ser Asp Trp
 65                  70                  75

<210> SEQ ID NO 102
<211> LENGTH: 151
<212> TYPE: PRT
<213> ORGANISM: Ebola virus

<400> SEQUENCE: 102

Val Ile Leu Ala Ala Gly Ile Gln Asp Gln Leu Ile Asp Gln Ser Leu
  1               5                  10                  15

Ile Glu Pro Leu Ala Gly Ala Leu Gly Leu Ile Ser Asp Trp Leu Leu
                 20                  25                  30

Thr Thr Asn Thr Asn His Phe Asn Met Arg Thr Gln Arg Val Lys Glu
             35                  40                  45

Gln Leu Ser Leu Lys Met Leu Ser Leu Ile Arg Ser Asn Ile Leu Lys
 50                  55                  60

Phe Ile Asn Lys Leu Asp Ala Leu His Val Val Asn Tyr Asn Gly Leu
 65                  70                  75                  80
```

Leu Ser Ser Ile Glu Ile Gly Thr Gln Asn His Thr Ile Ile Ile Thr
                85                  90                  95

Arg Thr Asn Met Gly Phe Leu Val Glu Leu Gln Glu Pro Asp Lys Ser
            100                 105                 110

Ala Met Asn Arg Lys Pro Gly Pro Ala Lys Phe Ser Leu Leu His
        115                 120                 125

Glu Ser Thr Leu Lys Ala Phe Thr Gln Gly Ser Ser Thr Arg Met Gln
    130                 135                 140

Ser Leu Ile Leu Glu Phe Asn
145                 150

<210> SEQ ID NO 103
<211> LENGTH: 133
<212> TYPE: PRT
<213> ORGANISM: Ebola virus

<400> SEQUENCE: 103

Tyr Ser Leu Asn Pro Gln Leu Arg Asn Cys Lys Leu Pro Lys His Ile
1               5                   10                  15

Tyr Arg Leu Lys Tyr Asp Val Thr Val Thr Lys Phe Leu Ser Asp Val
            20                  25                  30

Pro Val Ala Thr Leu Pro Ile Asp Phe Ile Val Pro Val Leu Leu Lys
        35                  40                  45

Ala Leu Ser Gly Asn Gly Phe Cys Pro Val Glu Pro Arg Cys Gln Gln
    50                  55                  60

Phe Leu Asp Glu Ile Ile Lys Tyr Thr Met Gln Asp Ala Leu Phe Leu
65                  70                  75                  80

Lys Tyr Tyr Leu Lys Asn Val Gly Ala Gln Glu Asp Cys Val Asp Glu
                85                  90                  95

His Phe Gln Glu Lys Ile Leu Ser Ser Ile Gln Gly Asn Glu Phe Leu
            100                 105                 110

His Gln Met Phe Phe Trp Tyr Asp Leu Ala Ile Leu Thr Arg Arg Gly
        115                 120                 125

Arg Leu Asn Arg Gly
    130

<210> SEQ ID NO 104
<211> LENGTH: 76
<212> TYPE: PRT
<213> ORGANISM: Ebola virus

<400> SEQUENCE: 104

Thr Trp Phe Val His Asp Asp Leu Ile Asp Ile Leu Gly Tyr Gly Asp
1               5                   10                  15

Tyr Val Phe Trp Lys Ile Pro Ile Ser Met Leu Pro Leu Asn Thr Gln
            20                  25                  30

Gly Ile Pro His Ala Ala Met Asp Trp Tyr Gln Ala Ser Val Phe Lys
        35                  40                  45

Glu Ala Val Gln Gly His Thr His Ile Val Ser Val Ser Thr Ala Asp
    50                  55                  60

Val Leu Ile Met Cys Lys Asp Leu Ile Thr Cys Arg
65                  70                  75

<210> SEQ ID NO 105
<211> LENGTH: 59
<212> TYPE: PRT
<213> ORGANISM: Ebola virus

```
<400> SEQUENCE: 105

Pro Tyr Pro Thr Arg Asn Val Gln Thr Leu Cys Glu Ala Leu Leu Ala
1               5                   10                  15

Asp Gly Leu Ala Lys Ala Phe Pro Ser Asn Met Met Val Val Thr Glu
            20                  25                  30

Arg Glu Gln Lys Glu Ser Leu Leu His Gln Ala Ser Trp His His Thr
        35                  40                  45

Ser Asp Asp Phe Gly Glu His Ala Thr Val Arg
    50                  55

<210> SEQ ID NO 106
<211> LENGTH: 178
<212> TYPE: PRT
<213> ORGANISM: Ebola virus

<400> SEQUENCE: 106

Thr Leu Cys Glu Ala Leu Leu Ala Asp Gly Leu Ala Lys Ala Phe Pro
1               5                   10                  15

Ser Asn Met Met Val Val Thr Glu Arg Glu Gln Lys Glu Ser Leu Leu
            20                  25                  30

His Gln Ala Ser Trp His His Thr Ser Asp Asp Phe Gly Glu His Ala
        35                  40                  45

Thr Val Arg Gly Ser Ser Phe Val Thr Asp Leu Glu Lys Tyr Asn Leu
    50                  55                  60

Ala Phe Arg Tyr Glu Phe Thr Ala Pro Phe Ile Glu Tyr Cys Asn Arg
65                  70                  75                  80

Cys Tyr Gly Val Lys Asn Val Phe Asn Trp Met His Tyr Thr Ile Pro
                85                  90                  95

Gln Cys Tyr Met His Val Ser Asp Tyr Tyr Asn Pro Pro His Asn Leu
            100                 105                 110

Thr Leu Glu Asn Arg Asp Asn Pro Pro Glu Gly Pro Ser Ser Tyr Arg
        115                 120                 125

Gly His Met Gly Gly Ile Glu Gly Leu Gln Gln Lys Leu Trp Thr Ser
    130                 135                 140

Ile Ser Cys Ala Gln Ile Ser Leu Val Glu Ile Lys Thr Gly Phe Lys
145                 150                 155                 160

Leu Arg Ser Ala Val Met Gly Asp Asn Gln Cys Ile Thr Val Leu Ser
                165                 170                 175

Val Phe

<210> SEQ ID NO 107
<211> LENGTH: 144
<212> TYPE: PRT
<213> ORGANISM: Ebola virus

<400> SEQUENCE: 107

Tyr Met His Val Ser Asp Tyr Tyr Asn Pro His Asn Leu Thr Leu
1               5                   10                  15

Glu Asn Arg Asp Asn Pro Pro Glu Gly Pro Ser Ser Tyr Arg Gly His
            20                  25                  30

Met Gly Gly Ile Glu Gly Leu Gln Gln Lys Leu Trp Thr Ser Ile Ser
        35                  40                  45

Cys Ala Gln Ile Ser Leu Val Glu Ile Lys Thr Gly Phe Lys Leu Arg
    50                  55                  60

Ser Ala Val Met Gly Asp Asn Gln Cys Ile Thr Val Leu Ser Val Phe
```

```
              65                  70                  75                  80
Pro Leu Glu Thr Asp Ala Asp Glu Gln Glu Gln Ser Ala Glu Asp Asn
                85                  90                  95

Ala Ala Arg Val Ala Ala Ser Leu Ala Lys Val Thr Ser Ala Cys Gly
            100                 105                 110

Ile Phe Leu Lys Pro Asp Glu Thr Phe Val His Ser Gly Phe Ile Tyr
        115                 120                 125

Phe Gly Lys Lys Gln Tyr Leu Asn Gly Val Gln Leu Pro Gln Ser Leu
    130                 135                 140

<210> SEQ ID NO 108
<211> LENGTH: 131
<212> TYPE: PRT
<213> ORGANISM: Ebola virus

<400> SEQUENCE: 108

Ser Ala Cys Gly Ile Phe Leu Lys Pro Asp Glu Thr Phe Val His Ser
1               5                   10                  15

Gly Phe Ile Tyr Phe Gly Lys Lys Gln Tyr Leu Asn Gly Val Gln Leu
            20                  25                  30

Pro Gln Ser Leu Lys Thr Ala Thr Arg Met Ala Pro Leu Ser Asp Ala
        35                  40                  45

Ile Phe Asp Asp Leu Gln Gly Thr Leu Ala Ser Ile Gly Thr Ala Phe
    50                  55                  60

Glu Arg Ser Ile Ser Glu Thr Arg His Ile Phe Pro Cys Arg Ile Thr
65                  70                  75                  80

Ala Ala Phe His Thr Phe Phe Ser Val Arg Ile Leu Gln Tyr His His
                85                  90                  95

Leu Gly Phe Asn Lys Gly Phe Asp Leu Gly Gln Leu Thr Leu Gly Lys
            100                 105                 110

Pro Leu Asp Phe Gly Thr Ile Ser Leu Ala Leu Ala Val Pro Gln Val
        115                 120                 125

Leu Gly Gly
    130

<210> SEQ ID NO 109
<211> LENGTH: 183
<212> TYPE: PRT
<213> ORGANISM: Ebola virus

<400> SEQUENCE: 109

Thr Leu Gly Lys Pro Leu Asp Phe Gly Thr Ile Ser Leu Ala Leu Ala
1               5                   10                  15

Val Pro Gln Val Leu Gly Gly Leu Ser Phe Leu Asn Pro Glu Lys Cys
            20                  25                  30

Phe Tyr Arg Asn Leu Gly Asp Pro Val Thr Ser Gly Leu Phe Gln Leu
        35                  40                  45

Lys Thr Tyr Leu Arg Met Ile Glu Met Asp Asp Leu Phe Leu Pro Leu
    50                  55                  60

Ile Ala Lys Asn Pro Gly Asn Cys Thr Ala Ile Asp Phe Val Leu Asn
65                  70                  75                  80

Pro Ser Gly Leu Asn Val Pro Gly Ser Gln Asp Leu Thr Ser Phe Leu
                85                  90                  95

Arg Gln Ile Val Arg Arg Thr Ile Thr Leu Ser Ala Lys Asn Lys Leu
            100                 105                 110

Ile Asn Thr Leu Phe His Ala Ser Ala Asp Phe Glu Asp Glu Met Val
```

```
            115                 120                 125
Cys Lys Trp Leu Leu Ser Ser Thr Pro Val Met Ser Arg Phe Ala Ala
    130                 135                 140

Asp Ile Phe Ser Arg Thr Pro Ser Gly Lys Arg Leu Gln Ile Leu Gly
145                 150                 155                 160

Tyr Leu Glu Gly Thr Arg Thr Leu Leu Ala Ser Lys Ile Ile Asn Asn
                165                 170                 175

Asn Thr Glu Thr Pro Val Leu
            180

<210> SEQ ID NO 110
<211> LENGTH: 57
<212> TYPE: PRT
<213> ORGANISM: Ebola virus

<400> SEQUENCE: 110

Ser Gly Leu Phe Gln Leu Lys Thr Tyr Leu Arg Met Ile Glu Met Asp
1               5                   10                  15

Asp Leu Phe Leu Pro Leu Ile Ala Lys Asn Pro Gly Asn Cys Thr Ala
            20                  25                  30

Ile Asp Phe Val Leu Asn Pro Ser Gly Leu Asn Val Pro Gly Ser Gln
        35                  40                  45

Asp Leu Thr Ser Phe Leu Arg Gln Ile
    50                  55

<210> SEQ ID NO 111
<211> LENGTH: 59
<212> TYPE: PRT
<213> ORGANISM: Ebola virus

<400> SEQUENCE: 111

Thr Pro Val Met Ser Arg Phe Ala Ala Asp Ile Phe Ser Arg Thr Pro
1               5                   10                  15

Ser Gly Lys Arg Leu Gln Ile Leu Gly Tyr Leu Glu Gly Thr Arg Thr
            20                  25                  30

Leu Leu Ala Ser Lys Ile Ile Asn Asn Asn Thr Glu Thr Pro Val Leu
        35                  40                  45

Asp Arg Leu Arg Lys Ile Thr Leu Gln Arg Trp
    50                  55

<210> SEQ ID NO 112
<211> LENGTH: 92
<212> TYPE: PRT
<213> ORGANISM: Ebola virus

<400> SEQUENCE: 112

Cys Thr Val Asp Leu Ala Gln Ile Leu Arg Glu Tyr Ser Trp Ala His
1               5                   10                  15

Ile Leu Glu Gly Arg Pro Leu Ile Gly Ala Thr Leu Pro Cys Met Ile
            20                  25                  30

Glu Gln Phe Lys Val Phe Trp Leu Lys Pro Tyr Glu Gln Cys Pro Gln
        35                  40                  45

Cys Ser Asn Ala Lys Gln Pro Gly Gly Lys Pro Phe Val Ser Val Ala
    50                  55                  60

Val Lys Lys His Ile Val Ser Ala Trp Pro Asn Ala Ser Arg Ile Ser
65                  70                  75                  80

Trp Thr Ile Gly Asp Gly Ile Pro Tyr Ile Gly Ser
            85                  90
```

<210> SEQ ID NO 113
<211> LENGTH: 42
<212> TYPE: PRT
<213> ORGANISM: Ebola virus

<400> SEQUENCE: 113

Trp Thr Ile Gly Asp Gly Ile Pro Tyr Ile Gly Ser Arg Thr Glu Asp
1               5                   10                  15

Lys Ile Gly Gln Pro Ala Ile Lys Pro Lys Cys Pro Ser Ala Ala Leu
            20                  25                  30

Arg Glu Ala Ile Glu Leu Ala Ser Arg Leu
        35                  40

<210> SEQ ID NO 114
<211> LENGTH: 176
<212> TYPE: PRT
<213> ORGANISM: Ebola virus

<400> SEQUENCE: 114

Gly Asp Gly Ile Pro Tyr Ile Gly Ser Arg Thr Glu Asp Lys Ile Gly
1               5                   10                  15

Gln Pro Ala Ile Lys Pro Lys Cys Pro Ser Ala Ala Leu Arg Glu Ala
            20                  25                  30

Ile Glu Leu Ala Ser Arg Leu Thr Trp Val Thr Gln Gly Ser Ser Asn
        35                  40                  45

Ser Asp Leu Leu Ile Lys Pro Phe Leu Glu Ala Arg Val Asn Leu Ser
    50                  55                  60

Val Gln Glu Ile Leu Gln Met Thr Pro Ser His Tyr Ser Gly Asn Ile
65                  70                  75                  80

Val His Arg Tyr Asn Asp Gln Tyr Ser Pro His Ser Phe Met Ala Asn
                85                  90                  95

Arg Met Ser Asn Ser Ala Thr Arg Leu Ile Val Ser Thr Asn Thr Leu
            100                 105                 110

Gly Glu Phe Ser Gly Gly Gly Gln Ser Ala Arg Asp Ser Asn Ile Ile
        115                 120                 125

Phe Gln Asn Val Ile Asn Tyr Ala Val Ala Leu Phe Asp Ile Lys Phe
    130                 135                 140

Arg Asn Thr Glu Ala Thr Asp Ile Gln Tyr Asn Arg Ala His Leu His
145                 150                 155                 160

Leu Thr Lys Cys Cys Thr Arg Glu Val Pro Ala Gln Tyr Leu Thr Tyr
                165                 170                 175

<210> SEQ ID NO 115
<211> LENGTH: 75
<212> TYPE: PRT
<213> ORGANISM: Ebola virus

<400> SEQUENCE: 115

Cys Thr Arg Glu Val Pro Ala Gln Tyr Leu Thr Tyr Thr Ser Thr Leu
1               5                   10                  15

Asp Leu Asp Leu Thr Arg Tyr Arg Glu Asn Glu Leu Ile Tyr Asp Ser
            20                  25                  30

Asn Pro Leu Lys Gly Gly Leu Asn Cys Asn Ile Ser Phe Asp Asn Pro
        35                  40                  45

Phe Phe Gln Gly Lys Arg Leu Asn Ile Ile Glu Asp Asp Leu Ile Arg
    50                  55                  60

```
Leu Pro His Leu Ser Gly Trp Glu Leu Ala Lys
 65                  70                  75
```

<210> SEQ ID NO 116
<211> LENGTH: 43
<212> TYPE: PRT
<213> ORGANISM: Ebola virus

<400> SEQUENCE: 116

```
Leu Lys Pro Thr Phe Lys His Ala Ser Val Met Ser Arg Leu Met Ser
 1               5                  10                  15

Ile Asp Pro His Phe Ser Ile Tyr Ile Gly Gly Ala Ala Gly Asp Arg
                20                  25                  30

Gly Leu Ser Asp Ala Ala Arg Leu Phe Leu Arg
                35                  40
```

<210> SEQ ID NO 117
<211> LENGTH: 77
<212> TYPE: PRT
<213> ORGANISM: Ebola virus

<400> SEQUENCE: 117

```
Thr Gly Ser Ser Thr Asn Asn Ser Asp Gly His Ile Glu Arg Ser Gln
 1               5                  10                  15

Glu Gln Thr Thr Arg Asp Pro His Asp Gly Thr Glu Arg Asn Leu Val
                20                  25                  30

Leu Gln Met Ser His Glu Ile Lys Arg Thr Thr Ile Pro Gln Glu Asn
                35                  40                  45

Thr His Gln Gly Pro Ser Phe Gln Ser Phe Leu Ser Asp Ser Ala Cys
            50                  55                  60

Gly Thr Ala Asn Pro Lys Leu Asn Phe Asp Arg Ser Arg
 65                  70                  75
```

<210> SEQ ID NO 118
<211> LENGTH: 84
<212> TYPE: PRT
<213> ORGANISM: Ebola virus

<400> SEQUENCE: 118

```
Thr Ile Pro Gln Glu Asn Thr His Gln Gly Pro Ser Phe Gln Ser Phe
 1               5                  10                  15

Leu Ser Asp Ser Ala Cys Gly Thr Ala Asn Pro Lys Leu Asn Phe Asp
                20                  25                  30

Arg Ser Arg His Asn Val Lys Phe Gln Asp His Asn Ser Ala Ser Lys
                35                  40                  45

Arg Glu Gly His Gln Ile Ile Ser His Arg Leu Val Leu Pro Phe Phe
            50                  55                  60

Thr Leu Ser Gln Gly Thr Arg Gln Leu Thr Ser Ser Asn Glu Ser Gln
 65                  70                  75                  80

Thr Gln Asp Glu
```

<210> SEQ ID NO 119
<211> LENGTH: 70
<212> TYPE: PRT
<213> ORGANISM: Ebola virus

<400> SEQUENCE: 119

```
Ser Met His Tyr Lys Leu Asp Glu Val Leu Trp Glu Ile Glu Ser Phe
 1               5                  10                  15
```

```
Lys Ser Ala Val Thr Leu Ala Glu Gly Glu Gly Ala Gly Leu Leu
             20                  25                  30

Leu Ile Gln Lys Tyr Gln Val Lys Thr Leu Phe Phe Asn Thr Leu Ala
         35                  40                  45

Thr Glu Ser Ser Ile Glu Ser Glu Ile Val Ser Gly Met Thr Thr Pro
 50                  55                  60

Arg Met Leu Leu Pro Val
 65                  70

<210> SEQ ID NO 120
<211> LENGTH: 56
<212> TYPE: PRT
<213> ORGANISM: Ebola virus

<400> SEQUENCE: 120

Leu Pro Lys Gln Val Glu Val Ile Thr Met Asp Ala Glu Thr Thr Glu
 1               5                  10                  15

Asn Ile Asn Arg Ser Lys Leu Tyr Glu Ala Val Tyr Lys Leu Ile Leu
             20                  25                  30

His His Ile Asp Pro Ser Val Leu Lys Ala Val Val Leu Lys Val Phe
         35                  40                  45

Leu Ser Asp Thr Glu Gly Met Leu
 50                  55

<210> SEQ ID NO 121
<211> LENGTH: 676
<212> TYPE: PRT
<213> ORGANISM: Ebola virus

<400> SEQUENCE: 121

Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
             20                  25                  30

Ile Pro Leu Gly Val Ile His Asn Ser Thr Leu Gln Val Ser Asp Val
         35                  40                  45

Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
        130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
            195                 200                 205
```

```
Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
                340                 345                 350

Val His Ser Gln Gly Arg Glu Ala Ala Val Ser His Leu Thr Thr Leu
            355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
                420                 425                 430

Glu Asn Thr Asn Thr Ser Lys Ser Thr Asp Phe Leu Asp Pro Ala Thr
                435                 440                 445

Thr Thr Ser Pro Gln Asn His Ser Glu Thr Ala Gly Asn Asn Asn Thr
            450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Ile
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
```

```
                625                 630                 635                 640
Asn Asp Asn Trp Trp Thr Gly Trp Arg Gln Trp Ile Pro Ala Gly Ile
                    645                 650                 655
Gly Val Thr Gly Val Ile Ile Ala Val Ile Ala Leu Phe Cys Ile Cys
                660                 665                 670
Lys Phe Val Phe
        675

<210> SEQ ID NO 122
<211> LENGTH: 676
<212> TYPE: PRT
<213> ORGANISM: Ebola virus

<400> SEQUENCE: 122

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
                100                 105                 110

Ile Lys Lys Pro Asp Gly Ser Glu Cys Leu Pro Ala Ala Pro Asp Gly
            115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
                180                 185                 190

Phe Phe Ser Ser His Pro Leu Arg Glu Pro Val Asn Ala Thr Glu Asp
            195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
                260                 265                 270

Leu Ile Trp Lys Val Asn Pro Glu Ile Asp Thr Thr Ile Gly Glu Trp
            275                 280                 285

Ala Phe Trp Glu Thr Lys Lys Asn Leu Thr Arg Lys Ile Arg Ser Glu
                290                 295                 300

Glu Leu Ser Phe Thr Ala Val Ser Asn Arg Ala Lys Asn Ile Ser Gly
305                 310                 315                 320
```

```
Gln Ser Pro Ala Arg Thr Ser Asp Pro Gly Thr Asn Thr Thr Thr
            325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
            355                 360                 365

Ala Thr Ile Ser Thr Ser Pro Gln Pro Pro Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
            405                 410                 415

Ala Ser Asp Thr Pro Pro Ala Thr Thr Ala Ala Gly Pro Leu Lys Ala
            420                 425                 430

Glu Asn Thr Asn Thr Ser Lys Gly Thr Asp Leu Leu Asp Pro Ala Thr
            435                 440                 445

Thr Thr Ser Pro Gln Asn His Ser Glu Thr Ala Gly Asn Asn Asn Thr
450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
            485                 490                 495

Arg Arg Ala Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
            645                 650                 655

Gly Val Thr Gly Val Ile Ile Ala Val Ile Ala Leu Phe Cys Ile Cys
            660                 665                 670

Lys Phe Val Phe
            675

<210> SEQ ID NO 123
<211> LENGTH: 676
<212> TYPE: PRT
<213> ORGANISM: Bundibugyo virus

<400> SEQUENCE: 123

Met Val Thr Ser Gly Ile Leu Gln Leu Pro Arg Glu Arg Phe Arg Lys
1               5                   10                  15
```

```
Thr Ser Phe Phe Val Trp Val Ile Ile Leu Phe His Lys Val Phe Pro
             20                  25                  30

Ile Pro Leu Gly Val Val His Asn Asn Thr Leu Gln Val Ser Asp Ile
             35                  40                  45

Asp Lys Leu Val Cys Arg Asp Lys Leu Ser Ser Thr Ser Gln Leu Lys
50                   55                  60

Ser Val Gly Leu Asn Leu Glu Gly Asn Gly Val Ala Thr Asp Val Pro
65                       70                  75                  80

Thr Ala Thr Lys Arg Trp Gly Phe Arg Ala Gly Val Pro Lys Val
                 85                  90                  95

Val Asn Tyr Glu Ala Gly Glu Trp Ala Glu Asn Cys Tyr Asn Leu Asp
                100                 105                 110

Ile Lys Lys Ala Asp Gly Ser Glu Cys Leu Pro Glu Ala Pro Glu Gly
            115                 120                 125

Val Arg Gly Phe Pro Arg Cys Arg Tyr Val His Lys Val Ser Gly Thr
            130                 135                 140

Gly Pro Cys Pro Glu Gly Phe Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175

Ser Glu Gly Val Val Ala Phe Leu Ile Leu Pro Lys Thr Lys Lys Asp
                180                 185                 190

Phe Phe Gln Ser Pro Pro Leu His Glu Pro Ala Asn Met Thr Thr Asp
            195                 200                 205

Pro Ser Ser Tyr Tyr His Thr Val Thr Leu Asn Tyr Val Ala Asp Asn
210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
                260                 265                 270

Leu Ile Trp Lys Val Asn Pro Thr Val Asp Thr Gly Val Gly Glu Trp
                275                 280                 285

Ala Phe Trp Glu Asn Lys Lys Asn Phe Thr Lys Thr Leu Ser Ser Glu
290                 295                 300

Glu Leu Ser Val Ile Leu Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Lys Asp Pro Ala Ser Val Val Gln
            340                 345                 350

Val Arg Asp Leu Gln Arg Glu Asn Thr Val Pro Thr Ser Pro Leu Asn
            355                 360                 365

Thr Val Pro Thr Thr Leu Ile Pro Asp Thr Met Glu Glu Gln Thr Thr
            370                 375                 380

Ser His Tyr Glu Leu Pro Asn Ile Ser Gly Asn His Gln Glu Arg Asn
385                 390                 395                 400

Asn Thr Ala His Pro Glu Thr Leu Ala Asn Asn Pro Asp Asn Thr
                405                 410                 415

Thr Pro Ser Thr Pro Pro Gln Asp Gly Glu Arg Thr Ser Ser His Thr
            420                 425                 430
```

Thr Pro Ser Pro Arg Pro Val Pro Thr Ser Thr Ile His Pro Thr Thr
            435                 440                 445

Arg Glu Thr Gln Ile Pro Thr Thr Met Ile Thr Ser His Asp Thr Asp
450                 455                 460

Ser Asn Arg Pro Asn Pro Ile Asp Ile Ser Glu Ser Thr Glu Pro Gly
465                 470                 475                 480

Leu Leu Thr Asn Thr Ile Arg Gly Val Ala Asn Leu Leu Thr Gly Ser
            485                 490                 495

Arg Arg Thr Arg Arg Glu Ile Thr Leu Arg Thr Gln Ala Lys Cys Asn
                500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
            660                 665                 670

Lys Phe Leu Leu
            675

<210> SEQ ID NO 124
<211> LENGTH: 676
<212> TYPE: PRT
<213> ORGANISM: Sudan virus

<400> SEQUENCE: 124

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
                20                  25                  30

Met Pro Leu Gly Val Val Thr Asn Ser Thr Leu Glu Val Thr Glu Ile
            35                  40                  45

Asp Gln Leu Val Cys Lys Asp His Leu Ala Ser Thr Asp Gln Leu Lys
        50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Pro Asp Gly
        115                 120                 125

-continued

```
Val Arg Gly Phe Pro Arg Cys Arg Tyr Val His Lys Ala Gln Gly Thr
130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
                180                 185                 190

Phe Leu Gln Ser Pro Pro Ile Arg Glu Ala Val Asn Tyr Thr Glu Asn
            195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

Asn Asp Thr Ile His Leu His Gln Gln Leu Ser Asn Thr Thr Gly Arg
                260                 265                 270

Leu Ile Trp Thr Leu Asp Ala Asn Ile Asn Ala Asp Ile Gly Glu Trp
            275                 280                 285

Ala Phe Trp Glu Asn Lys Lys Asn Leu Ser Glu Gln Leu Arg Gly Glu
290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
                340                 345                 350

Leu His Ile Pro Glu Gly Glu Thr Thr Leu Pro Ser Gln Asn Ser Thr
            355                 360                 365

Glu Gly Arg Arg Val Gly Val Asn Thr Gln Glu Thr Ile Thr Glu Thr
            370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Pro Thr
                405                 410                 415

Thr Ala Pro Ser Pro Glu Ala Gln Thr Pro Thr Thr His Thr Ser Gly
            420                 425                 430

Pro Ser Val Met Ala Thr Glu Glu Pro Thr Thr Pro Pro Gly Ser Ser
            435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Thr Asn Thr Lys Ala Thr Gly Lys Cys Asn
                500                 505                 510

Pro Asn Leu His Tyr Trp Thr Ala Gln Glu Gln His Asn Ala Ala Gly
            515                 520                 525

Ile Ala Trp Ile Pro Tyr Phe Gly Pro Gly Ala Glu Gly Ile Tyr Thr
530                 535                 540
```

-continued

```
Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
                580                 585                 590

Leu Leu Arg Arg Trp Gly Gly Thr Cys Arg Ile Leu Gly Pro Asp Cys
            595                 600                 605

Cys Ile Glu Pro His Asp Trp Thr Lys Asn Ile Thr Asp Lys Ile Asn
            610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
                660                 665                 670

Lys Leu Leu Cys
            675
```

The invention claimed is:

1. A method of identifying a biological sample containing Filovirus-specific antibodies, comprising:
   contacting the biological sample with one or more peptides comprising the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14, wherein the one or more peptides are no more than 150 amino acids in length;
   detecting the presence or absence of an immune complex of Filovirus-specific antibodies from the biological sample with the one or more peptides; and
   wherein the presence of the immune complex identifies the biological sample as containing Filovirus-specific antibodies and the absence of the immune complex identifies the biological sample as not containing Filovirus-specific antibodies.

2. The method of claim 1, wherein the one or more peptides are no more than 100 amino acids in length.

3. The method of claim 1, wherein the one or more peptides consist of or consist essentially of the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14.

4. The method of claim 1, wherein the one or more peptides comprise at least two, at least three, at least four, or at least five peptides.

5. The method of claim 4, wherein the at least two, at least three, at least four or at least five peptides comprise the amino acid sequences selected from SEQ ID NO: 6, SEQ ID NO: 8, SEQ ID NO: 9, SEQ ID NO: 12 and SEQ ID NO: 14.

6. The method of claim 1, wherein the one or more peptides are biotinylated.

7. The method of claim 1, wherein the one or more peptides are linked to a solid support.

8. The method of claim 1, wherein the biological sample comprises a blood, plasma, urine, eye, serum, saliva, semen, breast milk, synovial fluid, or cerebrospinal fluid sample.

9. The method of claim 1, wherein the Filovirus is an Ebolavirus.

10. The method of claim 9, wherein the Ebolavirus is a Zaire ebolavirus (ZEBOV).

11. The method of claim 1, wherein the one or more peptides are no more than 75 amino acids in length.

12. The method of claim 1, wherein the one or more peptides consist of or consist essentially of:
   SEQ ID NO: 6, SEQ ID NO: 9 and SEQ ID NO: 12;
   SEQ ID NO: 6, SEQ ID NO: 8, SEQ ID NO: 9 and SEQ ID NO: 14; or
   SEQ ID NO: 6, SEQ ID NO: 8, SEQ ID NO: 9; SEQ ID NO: 12 and SEQ ID NO: 14.

13. A method, comprising:
   contacting a biological sample containing antibodies from a subject with one or more peptides comprising the amino acid sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14, wherein the one or more peptides are no more than 150 amino acids in length;
   detecting the presence of an immune complex of antibodies from the biological sample with the one or more peptides; and
   administering a therapeutically effective amount of an anti-viral agent to the subject.

14. The method of claim 13, wherein the one or more peptides are no more than 75 amino acids in length.

15. The method of claim 13, wherein the one or more peptides consist of or consist essentially of:
   SEQ ID NO: 6, SEQ ID NO: 9 and SEQ ID NO: 12;
   SEQ ID NO: 6, SEQ ID NO: 8, SEQ ID NO: 9 and SEQ ID NO: 14; or
   SEQ ID NO: 6, SEQ ID NO: 8, SEQ ID NO: 9; SEQ ID NO: 12 and SEQ ID NO: 14.

16. The method of claim 13, wherein the one or more peptides are no more than 100 amino acids in length.

17. The method of claim 13, wherein the antiviral agent is a monoclonal antibody.

18. The method of claim 17, wherein the monoclonal antibody specifically binds to an Ebolavirus glycoprotein (GP).

19. The method of claim 13, wherein the subject has a chronic Filovirus infection of immune privileged tissue.

20. The method of claim 19, wherein the subject has a chronic Filovirus infection of eye, testis, synovium, or meninges tissue.

21. The method of claim 13, wherein the subject does not have Filovirus disease or symptoms.

22. The method of claim 13, wherein the subject was previously immunized with a Filovirus vaccine.

23. The method of claim 22, wherein the Filovirus vaccine is an Ebolavirus vaccine.

24. The method of claim 13, wherein the subject is at risk of or is suspected of having a Filovirus infection.

25. The method of claim 13, wherein the anti-viral agent inhibits a Filovirus infection.

26. The method of claim 25, wherein the Filovirus infection is a Zaire ebolavirus (ZEBOV), Sudan virus (SUDV), Reston virus (RESTV), Taï Forest virus (TAFV), Marburg virus (MARV), or Bundibugyo virus (BDBV) infection.

* * * * *